US012692230B2

(12) United States Patent
Fett et al.

(10) Patent No.: US 12,692,230 B2
(45) Date of Patent: Jul. 28, 2026

(54) (1 H-INDOL-5-YL)ACRYLAMIDE DERIVATIVES AS INHIBITORS OF TEAD PROTEINS AND THE HIPPO-YAP1/TAZ SIGNALING CASCADE FOR THE TREATMENT OF CANCER

(71) Applicant: Sanofi, Paris (FR)

(72) Inventors: Eykmar Fett, Paris (FR); Olivier Venier, Paris (FR)

(73) Assignee: SANOFI, Paris (FR)

( * ) Notice: Subject to any disclaimer, the term of this patent is extended or adjusted under 35 U.S.C. 154(b) by 832 days.

(21) Appl. No.: 17/925,088

(22) PCT Filed: Apr. 6, 2021

(86) PCT No.: PCT/EP2021/058971
§ 371 (c)(1),
(2) Date: Nov. 14, 2022

(87) PCT Pub. No.: WO2021/204823
PCT Pub. Date: Oct. 14, 2021

(65) Prior Publication Data

US 2023/0140808 A1 May 4, 2023

(30) Foreign Application Priority Data

Apr. 7, 2020 (EP) .................................... 20315128
Oct. 22, 2020 (EP) .................................... 20315438

(51) Int. Cl.

| | |
|---|---|
| ***C07D 209/08*** | (2006.01) |
| ***A61P 35/00*** | (2006.01) |
| ***C07D 209/42*** | (2006.01) |
| ***C07D 401/04*** | (2006.01) |
| ***C07D 401/06*** | (2006.01) |
| ***C07D 403/06*** | (2006.01) |
| ***C07D 405/06*** | (2006.01) |
| ***C07D 417/06*** | (2006.01) |
| ***C07F 7/08*** | (2006.01) |

(52) U.S. Cl.
CPC ............ *C07D 209/08* (2013.01); *A61P 35/00* (2018.01); *C07D 209/42* (2013.01); *C07D 401/04* (2013.01); *C07D 401/06* (2013.01); *C07D 403/06* (2013.01); *C07D 405/06* (2013.01); *C07D 417/06* (2013.01); *C07F 7/0812* (2013.01)

(58) Field of Classification Search
CPC .. C07D 209/08; C07D 209/42; C07D 401/04; C07D 401/06; C07D 403/06; C07D 405/06; C07D 417/06; A61P 35/00; C07F 7/0812
See application file for complete search history.

(56) References Cited

U.S. PATENT DOCUMENTS

2014/0107106 A1* 4/2014 Sargent .................. A61P 31/04 546/281.1
2017/0044132 A1 2/2017 Tirayama et al.

FOREIGN PATENT DOCUMENTS

CN 105820104 A * 8/2016 ........... C07D 209/42
WO 2019232216 A1 12/2019

OTHER PUBLICATIONS

CAS Registry No. 2411245-65-1, which entered STN on Mar. 5, 2020 (Year: 2020).*
Han, Xiaohong et al., "Tracking longitudinal genetic changes of circulating tumor DNA (ctDNA) in advanced Lung adenocarcinoma treated with chemotherapy", J. Transl Med (2019) 17:339.
Holden, Jeffrey K. et al., "Targeting the Hippo Pathway and Cancer through the TEAD Family of Transcription Factors", Cancers, 2018, 10(3): 81.
Kurppa, Kari J. et al., "Treatment-induced tumor dormancy through YAP-mediated transcriptional reprogramming of the apoptotic pathway", Cancer Cell, Jan. 13, 2020, 37(1): 104-122.
Liu-Chittenden, Yi et al., "Genetic and pharmacological disruption of the TEAD-YAP complex suppresses the oncogenic activity of YAP", Genes & Development 26: 1300-1305, 2012.
Lu, Li et al., "Hippo signaling is a potent in vivo growth and tumor suppressor pathway in the mammalian liver", PNAS, Jan. 26, 2010; vol. 107, No. 4, 1437-1442.
Ma, Shenghong et al., "The Hippo Pathway: Biology and Pathophysiology", Annual Review of Biochemistry, 2019, vol. 88:577-604.
Nishio, Junko et al., "Requirement of full TCR repertoire for regulatory T cells to maintain intestinal homeostasis", PNAS, Oct. 13, 2015, vol. 112, No. 41, 12770-12775.
PCT International Preliminary Report on Patentability from PCT/EP2021/058971, mailed Oct. 6, 2022, 6 pages.
PCT International Search Report from PCT/EP2021/058971 mailed May 12, 2021, 3 pages.

(Continued)

*Primary Examiner* — Fereydoun G Sajjadi
*Assistant Examiner* — Anna Grace Kuckla
(74) *Attorney, Agent, or Firm* — McNeill PLLC

(57) ABSTRACT

The invention relates to indole compounds of formula (I) to their preparation and to their therapeutic use.

(I)

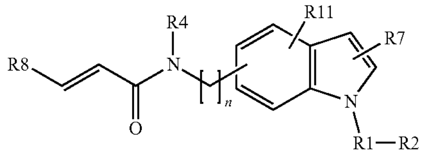

9 Claims, No Drawings

(56) References Cited

OTHER PUBLICATIONS

PCT Written Opinion of the International Search Authority from PCT/EP2021/058971 mailed May 12, 2021, 5 pages.
Reggiani, Francesca et al., "YAP and TAZ Are Not Identical Twins", Trends in Biochemical Sciences, vol. 46, Issue 2, p. 154-168, Feb. 2021.
Schroeder, Rebecca D. et al., "NF2/Merlin in hereditary neurofibromatosis 2 versus cancer: biologic mechanisms and clinical associations", Oncotarget, 2014, vol. 5, No. 1, 67-77.
Sekido, Yoshitaka, "Targeting the Hippo Pathway Is a New Potential Therapeutic Modality for Malignant Mesothelioma", Cancers 2018, 10, 90, 22 pages.
Totaro, Antonio et al., "YAP/TAZ upstream signals and downstream responses", Nat. Cell Biol. 2018; 20(8):888-899.
Yamauchi, Takayoshi et al., "Hippo Pathway in Mammalian Adaptive Immune System", Cells 2019, 8, 398: doi:10.3390/cells8050398.
Zanconato, Francesca et al., "YAP/TAZ at the roots of cancer", Cancer Cell 2016; 29(6): 783-803.
Zhang, Nailing et al., "The Merlin/NF2 tumor suppressor functions through the YAP oncoprotein to regulate tissue homeostasis in mammals", Dev. Cell. Jul. 20, 2010; 19(1): 27-38.

* cited by examiner

(1 H-INDOL-5-YL)ACRYLAMIDE DERIVATIVES AS INHIBITORS OF TEAD PROTEINS AND THE HIPPO-YAP1/TAZ SIGNALING CASCADE FOR THE TREATMENT OF CANCER

CROSS-REFERENCE TO RELATED APPLICATIONS

This application is a national phase entry pursuant to 35 U.S.C. § 371 of International Application No. PCT/EP2021/058971, filed Apr. 6, 2021, which claims the benefit of priority to EP Application Serial No. 20315438.0, filed Oct. 22, 2020, and EP Application Serial No. 20315128.7, filed Apr. 7, 2020.

The present invention relates to indole compounds, to their preparation and to their therapeutic use.

The compounds described herein are inhibitors of YAP1/TAZ-TEAD or TEAD-dependent gene transcription.

TEAD Proteins and the HIPPO-YAP1/TAZ Signaling Cascade

Transcriptional enhanced associate domain (TEAD) proteins are transcription factors comprised of four family members (TEAD1-4) that function in modulating gene expression in response to the HIPPO pathway. TEAD proteins preferentially associate with transcription co-activators yes associated protein 1 (YAP1) or transcriptional co-activator with PDZ-binding motif (TAZ, also known as VWVTR1). YAP1-TEAD or TAZ-TEAD bind to DNA and initiate the transcription of multiple different genes involved in cell proliferation, survival, mobility, stemness, and differentiation (reviewed in Holden and Cunningham, Cancer 2018). YAP1/TAZ-TEAD activity is tightly controlled by the HIPPO pathway. The HIPPO pathway was initially discovered in *Drosophila melanogaster* as a key regulator of tissue growth. It is an evolutionarily conserved signaling pathway regulating numerous biological processes, including cell growth and fate decision, organ size control, and regeneration. The core of the Hippo pathway in mammals consists of a cascade of kinases including MST1/2 and LATS1/2, their associated adaptor proteins SAV1 and MOB1, as well as upstream regulators, such as NF2, SCRIBBLE, CRUMBS, and multiple G protein-coupled receptors. The Hippo pathway is tightly regulated by both intrinsic and extrinsic signals, such as mechanical force, cell-cell contact, polarity, energy status, stress, as well as many diffusible hormonal factors (reviewed in Ma et al., Annual Rev of Biochem 2019). Upon activation of Hippo pathway kinases (i.e. Hippo "on" state), cytosolic YAP1 and TAZ proteins are phosphorylated and therefore, remain inactive through sequestration in the cytoplasm and/or degradation by the proteasomal machinery. Upon inactivation of the Hippo pathway kinases (i.e. Hippo "off" state), cytosolic YAP1 and TAZ are not anymore phosphorylated and hence free to translocate into the cell nucleus, where they associate with TEAD transcription factors to bind DNA and regulate gene expression. Decreasing levels of pYAP1NAP1 as well as increased expression of genes regulated by YAP1/TAZ-TEAD activity and increased promoter activity at TEAD-regulated genes are general indicators of YAP1 activation (reviewed in Totaro et al., Nature Cell Biol 2019).

The Hippo-YAP1/TAZ/TEAD Pathway and Human Cancer

In recent years, studies have demonstrated, that the deregulation of Hippo-YAP1/TAZ-TEAD activity is at the origin of tumor progression and resistance to therapy in a number of different cancer indications and contexts. In mice, systematic genetic studies have clearly shown that either knocking out HIPPO pathway components (which are YAP1 inhibitors) or overexpressing YAP1 activators such as YAP1, TAZ, TEAD lead to YAP1 activation and YAP1-TEAD-dependent tumor initiation and tumor progression (Zhang et al, Dev Cell 2010; Lu et al, PNAS 2010; Nishio et al, PNAS 2015; Liu-Chittenden et al, Genes and Dev 2012). In humans, genetic alterations in the pathway are most prevalent for NF2 (neurofibromin), an upstream regulator of the core Hippo pathway, that has been linked to a heritable cancer syndrome and that has been classified as a tumor suppressor gene. Hundreds of somatically acquired mutations have been reported in NF2, predominantly in meningiomas, mesotheliomas and peripheral nerve sheath tumors, but also in other cancer types. (reviewed in Schroeder et al., Oncotarget 2013). Genetic alterations beyond NF2 and directly present within the core Hippo pathway are less frequently observed in patients and found at high prevalence only in certain indications such as, e.g. malignant mesothelioma. Malignant mesothelioma is a highly lethal cancer of serosal membranes and almost exclusively associated with asbestos exposure. It is a therapeutic indication that shows prevalent alterations in the HIPPO signaling pathway as well as high YAP1 activation and high dependence on YAP1-TEAD activity (reviewed in Sekido et al., Cancers 2018). Increased YAP1 or YAP1-TEAD activity is not limited to genetic alterations in the HIPPO pathway and can also be the result of upregulation through multiple interconnected signals. Numerous pathways with critical role in tumorigenesis feed into the HIPPO-YAP1/TAZ/TEAD1 cascade, well described examples include the RTK-RAS-RAF-MEK-ERK, WNT, TGF-beta, and AMPK pathways (reviewed in Han et al., J Transl Med 2019). The number of tumor types that depend at least in part on YAP1-TEAD activation is hence tremendous and spans from breast, ovarian, uterine, and prostate cancers to lung, gastric, colorectal, bladder, pancreatic, and liver cancers, and further to sarcomas, esophageal, head and neck cancers, uveal melanoma, and glioma (reviewed in Zanconato et al., Cancer Cell 2016). Recent studies reveal an interplay between the HIPPO-YAP/TAZ/TEAD pathway and the human immune response (reviewed in Yamauchi and Moroishi, Cells 2019).

YAP1 activation has been observed in the context of resistance to therapy and is recognized as a main mechanism of resistance and survival to anti-cancer treatment. In esophageal carcinoma, YAP1 is a positive regulator of EGFR (Epidermal Growth Factor Receptor) and the induction of YAP1 is associated with resistance to 5-FU and docetaxel. In the context of targeted therapies, YAP1 in BRAF-mutant tumors, acts as a parallel survival input to promote resistance to RAF and MEK inhibitor therapy in melanoma. Similarly, activation of YAP1 is a mechanism of survival to EGFR and MEK inhibitor treatment in the context of EGFR mutant lung cancer and multiple studies have identified YAP1 activation as one of the main bypass mechanism to KRAS inhibition. In a hormone-dependent tumor context, TAZ inhibition was shown to restore sensitivity to tamoxifen in breast cancer. In prostate carcinoma cells, androgen deprivation therapy resistance was associated with increased YAP nuclear localization and activity (reviewed in Reggiani et al., 2020; Kurppa et al., Cancer Cell 2020).

Thus, the HIPPO-YAP/TAZ/TEAD pathway is a key player in cancer development and tumor maintenance and targeting this pathway is key for cancer treatment, both in a first line therapy setting as well as in the context of overcoming drug resistance with multiple cancer indications.

Therefore, there is a need for inhibitors of YAP1/TAZ-TEAD or TEAD-dependent gene transcription.

Disclosed herein are the compounds of the formula (I)

(I)

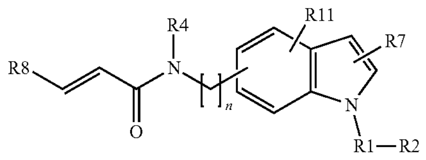

in which:

n is an integer chosen from 0 and 1

R1 is chosen from
- a single bond, and
- a (C1-C4) alkylene group,

R2 is chosen from:
- a (C1-C4) alkyl group or substituted with one or more fluorine atoms,
- a (C1-C3) alkoxy group substituted with one or more fluorine atoms,
- a phenyl group unsubstituted or substituted with one or more R3 groups,
- a (C4-C8) cycloalkyl group unsubstituted or substituted with one or more R5 groups,
- a (C4-C8) heterocyclyl group unsubstituted or substituted with one or more R6 groups, and
- a NR9R10 group, R3 is chosen from a
- a (C1-C4) alkyl group unsubstituted or substituted with one or more fluorine atoms,
- a cyclopropyl group,
- a halogen atom,
- a (C1-C3) alkoxy group unsubstituted or substituted with one or more fluorine atoms,
- a pentafluorosulfanyl group,
- a nitrile group,
- a (C1-C3) trialkylsilyl group,
- a (C1-C3) aklylsulfonyl group, and
- a phenyl group unsubstituted or substituted with a trifluoromethyl group, R4 is chosen from a hydrogen atom and a (C1-C4) alkyl group, R5 is chosen from a fluorine atom and a trifluoromethyl group, R6 is chosen from
- a phenyl group unsubstituted or substituted with one or more fluorine atoms or one or more CF3 groups,
- a (C1-C4) alkyl group substituted with one or more fluorine atoms, and
- a fluorine atom, R7 is chosen from
- a hydrogen atom,
- a nitrile group, and
- a (C1-C4) alkyl group unsubstituted or substituted with a (C1-C3) alkoxy group or a hydroxy group,
- a COO(C1-C4) alkyl group, and
- a CONH2 group, R8 is chosen from a hydrogen atom and a (C1-C4) alkyl group unsubstituted or substituted with a di(C1-C4) alkylamino group, R9 and R10 are identical or different and chosen from an (C1-C3) alkyl group unsubstituted or substituted with one or more fluorine atoms, R11 is chosen from a hydrogen atom, a fluorine atom and a chlorine atom or a pharmaceutically acceptable salt thereof.

The compounds of formula (I) may comprise one or more asymmetric carbon atoms. They may thus exist in the form of enantiomers or diastereoisomers and also mixtures thereof.

The compounds of formula (I) may be present as well under tautomer forms.

The compounds of formula (I) may exist in the form of bases or addition salts with acids or bases, in particular pharmaceutically acceptable salts.

Pharmaceutically acceptable salts of the compounds of formula (I) do form part of the invention.

As used herein, certain terms have the following definitions:
- a halogen atom: a fluorine, a chlorine, a bromine or an iodine atom;
- an alkyl group: a linear or branched saturated aliphatic group. Examples include the groups methyl, ethyl, propyl, isopropyl, etc;
- a cycloalkyl group: a cyclic alkyl group, including spiro groups. Examples include the groups cyclopropyl, cyclobutyl, cyclopentyl, cyclohexyl, spiro[2.3]hexanyl, etc.;
- an alkylene group: a saturated linear or branched divalent alkyl group. Examples include —CH2- (or methylene), ethylene, 1-methylethylene or propylene;
- an alkoxy group: a radical —O-alkyl in which the alkyl group is as defined above.

Examples of alkoxy group include methoxy, ethoxy, isopropoxy, etc.;
- a nitrile group: a group CN;
- a hydroxy group: a group OH;
- an aryl group: a cyclic aromatic group comprising between 5 and 10 carbon atoms.

Examples of an aryl group include phenyl group;
- a heterocyclyl group: a saturated or insaturated or cyclic group containing between 4 and 9 carbon atoms, and containing 1 or 2 heteroatoms, such as oxygen or nitrogen. Examples of heterocyclyl groups include pyrrolidine, piperazine, piperidine, tetrahydropyran, morpholine and diazepane groups;
- an amino group: a group —NH2;
- a dialkylamino group: an amino group substituted with two alkyl groups;
- a sulfonyl group: a substituted SO2 group; and
- a silyl group: a group containing a silicon atom. Example of silyl groups includes trimethylsilyl group.

In one aspect, the compounds of formula (I) comprise a first group of compounds of the following formula:

(I)

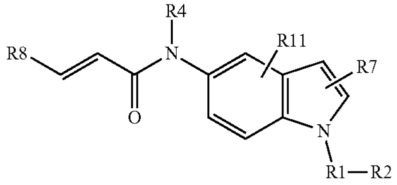

or a pharmaceutically acceptable salt thereof.

In another aspect, the compounds of formula (I) comprise a second group composed of the compounds in which R4 is a hydrogen atom.

In another aspect, the compounds of formula (I) comprise a third group composed of the compounds in which R7 is a hydrogen atom.

In another aspect, the compounds of formula (I) comprise a fourth group composed of the compounds in which R8 is a hydrogen atom.

In another aspect, the compounds of formula (I) comprise a fifth group composed of the compounds in which:

n is 0,

R1 is a single bond;

R2 is chosen from:

- a phenyl group unsubstituted or substituted with one or more R3 groups,
- a (C4-C8) cycloalkyl group unsubstituted or substituted with one or more R5 groups, and
- a (C4-C8) heterocyclyl group unsubstituted or substituted with one or more R6 groups.

Among the compounds of the fifth group, mention may be made of the compounds of formula (I) for which R11 is a hydrogen atom.

Among the compounds of the fifth group, mention may be also made of the compounds of formula (I) for which R2 is a phenyl group substituted with one or more R3 groups.

Among the compounds of the latter groups, mention may be made of the compounds of formula (I) for which R3 is a (C1-C4) alkyl group substituted with one or more fluorine atoms, in particular a trifluoromethyl group.

In another aspect, the compounds of formula (I) comprise a sixth group composed of the compounds for which R1 is chosen from a single bond and a methylene group.

In another aspect, the compounds of formula (I) comprise a seventh group composed of the compounds for which R2 is chosen from:

- a (C1-C4) alkyl group or substituted with three fluorine atoms,
- a (C1-C3) alkoxy group substituted with three fluorine atoms, in particular a trifluoroethoxy group,
- a phenyl group unsubstituted or substituted with one or more R3 groups,
- a (C4-C8) cycloalkyl group, in particular a cyclobutyl, a cyclopentyl, a cyclohexyl or a spiro[2.3]hexanyl, unsubstituted or substituted with one or more R5 groups,
- a (C4-C8) heterocyclyl group, in particular a tetrahydrofuranyl, a tetrahydropyranyl, a piperidinyl, a pyrrolidinyl or a pyridinyl group, unsubstituted or substituted with one or more R6 groups, and
- a NR9R10 group, In another aspect, the compounds of formula (I) comprise an eighth group composed of the compounds for which R3 is chosen from:

- a methyl group or a (C1-C4) trifluoroalkyl group, in particular a trifluoromethyl group,
- a cyclopropyl group,
- an iodine or a fluorine atom,
- a methoxy group or a trifluoromethoxy group,
- a pentafluorosulfanyl group,
- a nitrile group,
- a trimethylsilyl group,
- a methylsulfonyl group, and
- a phenyl group unsubstituted or substituted with a trifluoromethyl group, In another aspect, the compounds of formula (I) comprise a ninth group composed of the compounds for which R4 is chosen from a hydrogen atom and a methyl group.

Among the compounds of the latter groups, mention may be made of the compounds of formula (I) for which R4 is a hydrogen atom.

In another aspect, the compounds of formula (I) comprise a tenth group composed of the compounds for which R6 is chosen from:

- a phenyl group unsubstituted or substituted with three fluorine atoms or a trifluoromethyl group,
- a (C1-C4) alkyl group substituted with three fluorine atoms, in particular a trifluoromethyl or a trifluoroethyl group, and
- a fluorine atom.

In another aspect, the compounds of formula (I) comprise an eleventh group composed of the compounds for which R7 is chosen from a hydrogen atom, a nitrile atom or a methyl group.

In another aspect, the compounds of formula (I) comprise a twelfth group composed of the compounds for which R7 is located at position 3, according to IUPAC convention, of the central indole group.

In another aspect, the compounds of formula (I) comprise a thirteenth group composed of the compounds for which R8 is a hydrogen atom or a methyl group substituted with a dimethylamino group.

In another aspect, the compounds of formula (I) comprise a fourteenth group composed of the compounds for which R9 and R10 are chosen from a methyl group and a trifluoroethyl group.

In another aspect, the compounds of formula (I) comprise a fifteenth group composed of the compounds for which R11 is located at position 6 or 7, according to IUPAC convention, of the central indole group.

In another aspect, the compounds of formula (I) comprise a sixteenth group composed of the compounds for which:

- R11 is chosen from a fluorine atom and a chlorine atom,
- n is 0,
- R1 is a single bond or a (C1-C4) alkylene group, in particular a single bond or a methylene group
- R2 is a phenyl group unsubstituted or substituted with one or more R3 groups, and
- R3 is a (C1-C4) alkyl group unsubstituted or substituted with one or more fluorine atoms, in particular a CF3 group.

All these sub-groups taken alone or in combination are part of the description.

Among the compounds of formula (I) that are subjects matter of the invention, mention may be made in particular of the following compounds:

N-[1-[[3-(trifluoromethyl)phenyl]methyl]indol-5-yl]acrylamide

N-methyl-N-(1-(3-(trifluoromethyl)benzyl)-1H-indol-5-yl)acrylamide

N-(1-(5,5,5-trifluoropentyl)-1H-indol-5-yl)acrylamide

N-(1-(1-(3-(trifluoromethyl)phenyl)ethyl)-1H-indol-5-yl)acrylamide

N-(1-(3-(pentafluoro-λ6-sulfanyl)benzyl)-1H-indol-5-yl)acrylamide

N-(1-(4-(pentafluoro-λ6-sulfanyl)benzyl)-1H-indol-5-yl)acrylamide

N-(1-(4-(trifluoromethoxy)benzyl)-1H-indol-5-yl)acrylamide

N-(1-(3-(trifluoromethoxy)benzyl)-1H-indol-5-yl)acrylamide

N-(1-(3-iodobenzyl)-1H-indol-5-yl)acrylamide

N-(1-(2-fluoro-5-(trifluoromethyl)benzyl)-1H-indol-5-yl)acrylamide

N-(3-methyl-1-(3-(trifluoromethyl)benzyl)-1H-indol-5-yl) acrylamide
N-(1-(3-methoxybenzyl)-1H-indol-5-yl)acrylamide
N-(2-methyl-1-(3-(trifluorometheyObenzyl)-1H-indol-5-yl) acrylamide
N-(3-cyano-1-(3-(trifluoromethyl)benzyl)-1H-indol-5-yl) acrylamide
N-(1-(3-cyclopropylbenzyl)-1H-indol-5-yl)acrylamide
N-(2,3-dimethyl-1-(3-(trifluoromethyl)benzyl)-1H-indol-5-yl)acrylamide
N-(1-(3-methylbenzyl)-1H-indol-5-yl)acrylamide
N-(1-Benzyl-1H-indol-5-yl)-acrylamide
N-(1-(3-(trifluoromethyl)benzyl)-1H-indol-4-yl)acrylamide
(E)-4-(dimethylamino)-N-(1-(3-(trifluoromethyl)benzyl)-1H-indol-4-yl)but-2-enamide
N-(1-(3-(trifluoromethyObenzyl)-1H-indol-6-yl)acrylamide
N-(1-((4,4-difluorocyclohexyl)methyl)-1H-indol-5-yl)acrylamide
N-(1-((tetrahydro-2H-pyran-4-yl)methyl)-1H-indol-5-yl) acrylamide
N-(1-((4-(trifluoromethyl)cyclohexyl)methyl)-1H-indol-5-yl)acrylamide
N-(1-((1,1-difluorospiro[2.3]hexan-5-yl)methyl)-1H-indol-5-yl)acrylamide
N-(1-((3-fluorocyclopentyl)methyl)-1H-indol-5-yl)acrylamide
N-(1-(cyclohexylmethyl)-1H-indol-5-yl)acrylamide
N-(1-((3-(trifluoromethyl)cyclobutyl)methyl)-1H-indol-5-yl)acrylamide
N-(1-((3,3-difluorocyclopentyl)methyl)-1H-indol-5-yl) acrylamide
N-(1-([1,1'-biphenyl]-4-ylmethyl)-1H-indol-5-yl)acrylamide
N-(1-((3'-(trifluoromethyl)-[1,1'-biphenyl]-4-yl)methyl)-1H-indol-5-yl)acrylamide
N-(1-((4'-(trifluoromethyl)-[1,1'-biphenyl]-4-yl)methyl)-1H-indol-5-yl)acrylamide
N-(1-((trans)-4-(trifluoromethyl)cyclohexyl)-1H-indol-5-yl)acrylamide
N-(1-((cis)-4-(trifluoromethyl)cyclohexyl)-1H-indol-5-yl) acrylamide
N-(1-((1-(4-(trifluoromethyl)phenyl)piperidin-4-yl) methyl)-1H-indol-5-yl)acrylamide
N-(1-(2-(methyl(2,2,2-trifluoroethyl)amino)ethyl)-1H-indol-5-yl)acrylamide
N-(1-(2-(2,2,2-trifluoroethoxy)ethyl)-1H-indol-5-yl)acrylamide
N-(1-(1-(2,2,2-trifluoroethyl)piperidin-4-yl)-1H-indol-5-yl) acrylamide
N-(1-(4,4-difluorocyclohexyl)-1H-indol-5-yl)acrylamide
N-(1-(1-(4-(trifluoromethyl)phenyl)piperidin-4-yl)-1H-indol-5-yl)acrylamide
N-(1-(3-(3,3-difluoropyrrolidin-1-yl)propyl)-1H-indol-5-yl) acrylamide
N-(1-(4-(trimethylsilyl)benzyl)-1H-indol-5-yl)acrylamide
N-(1-(3-(trifluoromethyl)phenyl)-1H-indol-5-yl)acrylamide
N-(1-(4-(trifluoromethyl)phenyl)-1H-indol-5-yl)acrylamide
N-(1-(6-(trifluoromethyl)pyridin-3-yl)-1H-indol-5-yl)acrylamide
N-(1-(5-(trifluoromethyl)pyridin-2-yl)-1H-indol-5-yl)acrylamide
N-(1-(pyridin-3-yl)-1H-indol-5-yl)acrylamide
N-(1-(4-fluorophenyl)-1H-indol-5-yl)acrylamide
N-(1-(3,4-difluorophenyl)-1H-indol-5-yl)acrylamide
N-(1-(3-(methylsulfonyl)phenyl)-1H-indol-5-yl)acrylamide
N-(1-(4-cyanophenyl)-1H-indol-5-yl)acrylamide
N-(1-(3,5-difluorobenzyl)-1H-indol-5-yl)acrylamide
N-(1-(3,4-difluorobenzyl)-1H-indol-5-yl)acrylamide
N-(1-(3-cyanobenzyl)-1H-indol-5-yl)acrylamide
N-(1-((5-(trifluoromethyl)furan-2-yl)methyl)-1H-indol-5-yl)acrylamide
N-(1-(thiazol-4-ylmethyl)-1H-indol-5-yl)acrylamide
N-(1-((2-(trifluoromethyl)thiazol-4-yl)methyl)-1H-indol-5-yl)acrylamide
N-(1-(3-(trifluoromethyl)benzyl)-1H-indol-7-yl)acrylamide
N-(1-(3-(methylsulfonyl)benzyl)-1H-indol-5-yl)acrylamide
N-(3-(methoxymethyl)-1-(3-(trifluoromethyl)benzyl)-1H-indol-5-yl)acrylamide
methyl 5-acrylamido-1-(3-(trifluoromethyl)benzyl)-1H-indole-3-carboxylate
N-(1-(3-(trifluoromethyl)phenyl)-1H-indol-6-yl)acrylamide
N-(1-(4-(pentafluoro-λ6-sulfanyl)phenyl)-1H-indol-5-yl) acrylamide
N-(1-(4-(trifluoromethyl)phenyl)-1H-indol-6-yl)acrylamide
N-(1-(2-methyl-4-(trifluoromethyl)phenyl)-1H-indol-5-yl) acrylamide
N-(1-(3,5-difluorophenyl)-1H-indol-5-yl)acrylamide
N-(1-(5-fluoropyridin-3-yl)-1H-indol-5-yl)acrylamide
N-(1-(2-(trifluoromethyl)pyridin-4-yl)-1H-indol-5-yl)acrylamide
N-[3-methyl-1-[4-(trifluoromethyl)phenyl]indol-5-yl]acrylamide
N-[2-methyl-1-[4-(trifluoromethyl)phenyl]indol-5-yl]acrylamide
N-methyl-N-[2-methyl-1-[4-(trifluoromethyl)phenyl]indol-5-yl]acrylamide
N-(3-(methoxymethyl)-1-(4-(trifluoromethyl)phenyl)-1H-indol-5-yl)acrylamide
N-(6-fluoro-1-(4-(trifluoromethyl)phenyl)-1H-indol-5-yl) acrylamide
N-methyl-N-(1-(4-(trifluoromethyl)phenyl)-1H-indol-5-yl) acrylamide
(E)-N-(1-(4-(trifluoromethyl)phenyl)-1H-indol-5-yl)but-2-enamide
(E)-4-(dimethylamino)-N-(1-(4-(trifluoromethyl)phenyl)-1H-indol-5-yl)but-2-enamide
N-(6-chloro-1-(4-(trifluoromethyl)phenyl)-1H-indol-5-yl) acrylamide
N-(6-chloro-1-(3-(trifluoromethyl)benzyl)-1H-indol-5-yl) acrylamide
N-(7-chloro-1-(3-(trifluoromethyl)benzyl)-1H-indol-5-yl) acrylamide
N-(6-fluoro-1-(3-(trifluoromethyl)benzyl)-1H-indol-5-yl) acrylamide
N-(7-chloro-1-(4-(trifluoromethyl)phenyl)-1H-indol-5-yl) acrylamide
N-(3-(hydroxymethyl)-1-(4-(trifluoromethyl)phenyl)-1H-indol-5-yl)acrylamide
5-acrylamido-1-(3-(trifluoromethyl)benzyl)-1H-indole-3-carboxamide
5-acrylamido-1-(4-(trifluoromethyl)phenyl)-1H-indole-3-carboxamide
or a pharmaceutically acceptable salt thereof.

The compounds of formula (I) may be prepared according to the processes that follow. Unless otherwise mentioned, n and R1 to R10 are as defined previously.

In the following Schemes, the starting compounds and the reagents, when their preparation method is not described, are commercially available or described in the literature, or else may be prepared according to methods that are described therein or that are known to those skilled in the art.

SCHEME 1: Preparation of compounds of the formula (I)-General process

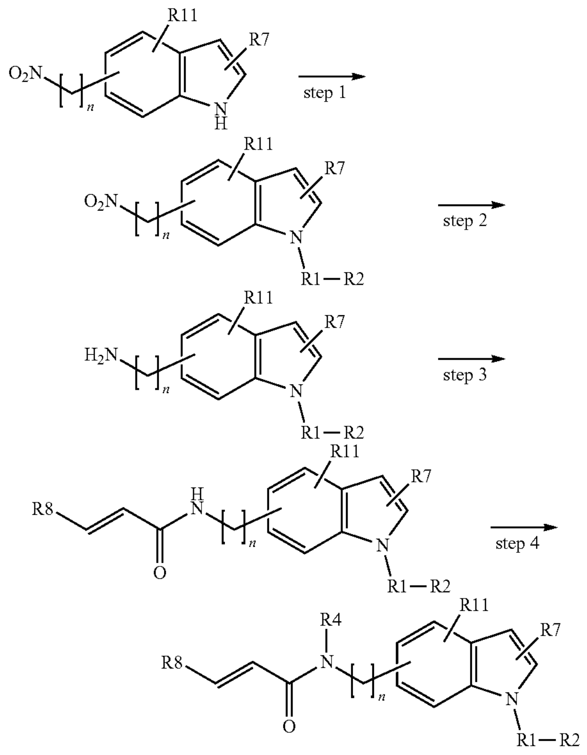

All compounds described hereinafter can be synthesized according to scheme 1.

Step 1 consists in an alkylation procedure of the indole nitrogen (by use the of corresponding alcools via Mitsunobu-reaction or the corresponding halogen-alkane derivatives, which themselves can be functionalized in further steps) except for R1=bond, where the corresponding iodo-aryl derivatives were used for a direct arylation.

Step 2 represents a reduction of the nitro-group followed in step 3 by an amide formation using the appropriate acryloyl chloride or acrylic acid derivatives.

The alkylation of the amide in step 4 is realized by the use of aliphatic halogenoalkane derivatives.

The examples that follow describe the preparation of certain compounds of formula (I). The examples are not limiting but serve merely to illustrate the present invention.

The following abbreviations and empirical formulae are used:

AcOEt ethylacetate
CMBP cyanomethylene-tributylphosphorane
DCM DCM
DEA diethylamine
DIEA diisopropyl ethylamine
DMEDA N,N'-dimethyl-1,2-ethanediamine
DMF N,N-dimethylformamide
DMSO dimethylsulfoxide
DPPF 1,1'-bis(diphenylphosphino)ferrocene]dichloropalladium(II)
EDCI (([3-(dimethylamino)propyl]imino)methylidene)(ethyl)amine hydrochloride
ESI Electrospray ionization
Et3N triethylamine
FA formic acid
HATU O-(7-azabenzotriazol-1-yl)-N,N,N',N'-tetramethyluronium hexafluoro-phosphate
John Phos ([1,1'-biphenyl]-2-yl)di-tert-butyl-phosphane
MeCN acetonitrile
MeOH methanol
PE petroleum ether
PDA photo diode array
PdCl2(PPh3)2 1,1'-bis(triphenylphosphine)-palladium(II) chloride
RT room temperature
SFC supercritical fluid chromatography
TLC thin layer chromatography
Tr Retention time
XantPhos (9,9-dimethyl-9H-xanthene-4,5-diyl)bis(diphenylphosphane)
° C. degree Celsius
ml milliliter(s)
mmol millimole(s)
min minute(s)
psi pounds per square inch
µm micrometer(s)
µmol micromole(s)
µl microliter(s)
h hour(s)

Some representative examples of the synthesis of the compounds of formula (I) are described in the following schemes.

SCHEME 2: Preparation of compounds of the formula (I)
Illustrative example of compounds of formula (I) for which R = (C1-C4) alkylene group

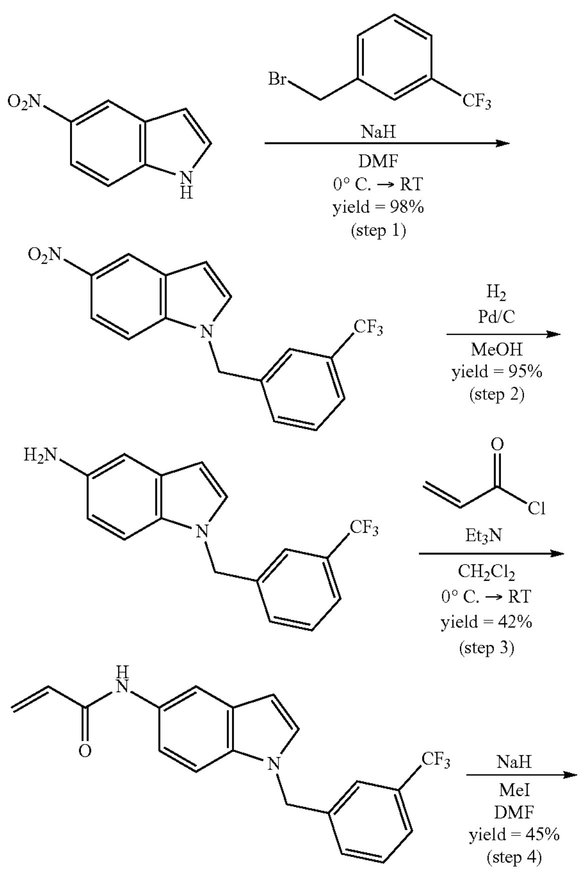

-continued

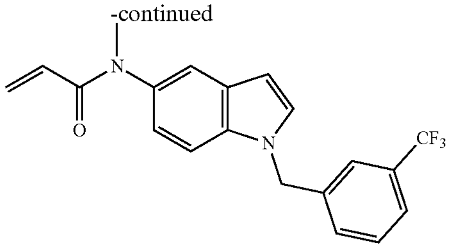

5-nitro-1-(3-(trifluoromethyl)benzyl)-1H-indole (step 1 of scheme 1)

To a solution of 5-nitroindole (500 mg, 3.02 mmol) in 5 ml DMF at 0° C. was added sodium hydride 60% in mineral oil (121 mg, 3.02 mmol) in several fractions, the mixture was allowed to rise at RT, stirred for 20 min at RT and cooled again to 0° C. before pouring drop by drop 3-(trifluoromethyl)benzyl bromide (737 mg, 3.02 mmol) solubilized in 2 ml of DMF. The solution was allowed to rise to RT and stirred for further 3 h at RT. The crude mixture was poured on ice and water, extracted with AcOEt, dried over $Na_2SO_4$, evaporated at reduced pressure to obtain 0.95 g of 5-nitro-1-(3-(trifluoromethyl)-benzyl)-1H-indole as a yellow solid, yield=98%.

1-(3-(trifluoromethyl)benzyl)-1H-indol-5-amine (Step 2 of Scheme 1)

5-nitro-1-(3-(trifluoromethyl)benzyl)-1H-indole (1 g, 3.12 mmol) obtained in the preceding step was solubilized in 30 ml of MeOH and 3 ml of AcOEt, Pd/C 10% (50% wet) (30 mg 160.0 μmol) was added and the mixture was hydrogenated in a Parr apparatus at RT under 30 psi hydrogen pressure for 3 h. After filtration and evaporation at reduced pressure 858 mg of a slightly brownish colored oil of were obtained and used without further purification in the next step, yield 95%.

Example 1 N-(1-(3-(trifluoromethyl)benzyl)-1H-indol-5-yl)acrylamide (Step 3 of Scheme 1)

1-(3-(trifluoromethyl)benzyl)-1H-indol-5-amine (150 mg, 517 μmol) obtained in the step described above were solubilized in DCM (2 ml) with $Et_3N$ (86 μl, 620 μmol), cooled down to 0° C. before adding acryloyl chloride (53 μl, 620 μmol). Stirring was continued for 2 h at RT. The reaction mixture was diluted with DCM, extracted with water, dried over $Na_2SO_4$, evaporated at reduced pressure and purified by column chromatography (silica gel, gradient heptane/AcOEt 100/0 to 50/50) to obtain 75 mg of N-(1-(3-(trifluoromethyl) benzyl)-1H-indol-5-yl)acrylamide as a white solid, yield 42%

Example 2 N-methyl-N-(1-(3-(trifluoromethyl)benzyl)-1H-indol-5-yl)acrylamide (Step 4 of Scheme 1)

N-(1-(3-(trifluoromethyl)benzyl)-1H-indol-5-yl)acrylamide (270 mg, 784 μmol) obtained in example 1 was solubilized in 2 ml DMF, cooled to 0° C. before adding sodium hydride 60% in mineral oil (31 mg, 784 μmol), the suspension was stirred 20 min at 0° C. before iodomethane (49 μl, 784 μmol) was added and the mixture was stirred 3 h at RT, poured into water, extracted with AcOEt, washed with water and an aqueous saturated solution of NaCl, dried over $Na_2SO_4$. After purification by reverse phase chromatography (C18, Water/$CH_3CN$, gradient 95/5 to 5/95) 130 mg of N-methyl-N-(1-(3-(trifluoromethyl)-benzyl)-1H-indol-5-yl) acrylamide were isolated as a colorless oil, yield 45%.

The following examples 3-29 (analogues of example 1) were synthesized using the same reaction sequence as in scheme 2, using the appropriate indoles, bromoalkyl and acrylic acid compounds as starting materials, which are known to those skilled in the art. Described hereinbelow are steps 3 of scheme 1.

Example 3 N-(1-(5,5,5-trifluoropentyl)-1H-indol-5-yl)acrylamide 1-(5,5,5-trifluoropentyl)-1H-indol-5-amine (200 mg, 780 μmol) were solubilized in DCM (5 ml) with $Et_3N$ (131 μl, 937 μmol), cooled down to 0° C. before adding acryloyl chloride (88 mg, 937 μmol). Stirring was continued for 1 h30 at RT. The reaction mixture was diluted with DCM, extracted with water, dried over $Na_2SO_4$, evaporated at reduced pressure and purified by column chromatography (silica gel, gradient heptane/AcOEt 100/0 to 70/30) then by reverse phase chromatography (C18, water/MeCN, gradient 95/5 to 5/95) to obtain 23 mg of N-(1-(5,5,5-trifluoropentyl)-1H-indol-5-yl)acrylamide as a brown oil, yield 10%.

Example 4 N-(1-(1-(3-(trifluoromethyl)phenyp-ethyl)-1H-indol-5-yl)acrylamide 1-(1-(3-(trifluoromethyl)phenyl)ethyl)-1H-indol-5-amine (200 mg, 657 μmol) were solubilized in DCM (5 ml) with $Et_3N$ (110 μl, 789 μmol), cooled down to 0° C. before adding acryloyl chloride (74 mg, 789 μmol). Stirring was continued for 3 h at RT. The reaction mixture was diluted with DCM, extracted with water, dried over $Na_2SO_4$, evaporated at reduced pressure and purified by column chromatography (silica gel, gradient heptane/AcOEt, 100/0 to 75/25) to obtain 66 mg of N-(1-(1-(3-(trifluoro-methyl)-phenyl) ethyl)-1H-indol-5-yl)acrylamide as a white solid after trituration in diethyl-ether, yield 28%.

Example 5 N-(1-(3-(pentafluoro-λ6-sulfanyl)benzyl)-1H-indol-5-yl)acrylamide 1-(3-(pentafluoro-λ6-sulfanyl)benzyl)-1H-indol-5-amine (200 mg, 574 μmol) were solubilized in DCM (5 ml) with $Et_3N$ (96 μl, 689 μmol), cooled down to 0° C. before adding acryloyl chloride (65 mg, 689 μmol). Stirring was continued for 3 h at RT. The reaction mixture was diluted with DCM, extracted with water, dried over $Na_2SO_4$, evaporated at reduced pressure and purified by column chromatography (silica gel, gradient heptane/AcOEt, 100/0 to 70/30) to obtain 80 mg of N-(1-(3-(pentafluoro-λ6-sulfanyl)benzyl)-1H-indol-5-yl)acrylamideas a white solid after trituration in diethylether, yield 34%.

Example 6 N-(1-(4-(pentafluoro-λ6-sulfanyl)benzyl)-1H-indol-5-yl)acrylamide 1-(4-(pentafluoro-λ6-sulfanyl)benzyl)-1H-indol-5-amine (200 mg, 574 μmol) were solubilized in DCM (5 ml) with $Et_3N$ (120 μl, 861 μmol), cooled down to 0° C. before adding acryloyl chloride (65 mg, 689 μmol). Stirring was continued for 1 h at RT. The reaction mixture was diluted with DCM, extracted with water, dried over $Na_2SO_4$, evaporated at reduced pressure and purified by column chromatography (silica gel, gradient heptane/AcOEt 100/0 to 50/50) to obtain 98 mg of N-(1-(4-(pentafluoro-λ6-sulfanyl)benzyl)-1H-indol-5-yl)acrylamideas a white solid after trituration in diethylether, yield 42%.

Example 7 N-(1-(4-(trifluoromethoxy)benzyl)-1H-indol-5-yl)acrylamide 1-(4-(trifluoromethoxy)benzyl)-1H-indol-5-amine (200 mg, 653 μmol) were solubilized in DCM (7 ml) with $Et_3N$ (192 μl, 1.31 mmol), cooled down to 0° C. before adding acryloyl chloride (66 μl, 784 μmol). Stirring was continued for 1 h at RT. The reaction mixture was diluted with DCM, extracted with water, dried over $Na_2SO_4$, evaporated at reduced pressure and purified by column chromatography (silica gel, gradient heptane/AcOEt, 100/0 to 70/30) to obtain 87 mg of N-(1-(4-(trifluoro-methoxy)-benzyl)-1H-indol-5-yl)acrylamide as an amorphous solid, yield 42.5%.

Example 8 N-(1-(3-(trifluoromethoxy)benzyl)-1H-indol-5-yl)acrylamide 1-(3-(trifluoromethoxy)benzyl)-1H-indol-5-amine (200 mg, 653 μmol) were solubilized in DCM (7 ml) with $Et_3N$ (192 μl, 1.31 mmol), cooled down to 0° C. before adding acryloyl chloride (66 μl, 784 μmol). Stirring was continued for 1 h at RT. The reaction mixture was diluted with DCM, extracted with water, dried over $Na_2SO_4$, evaporated at reduced pressure and purified by column chromatography (silica gel, gradient heptane/AcOEt, 100/0 to 70/30) to obtain 100 mg of N-(1-(3-(trifluoro-methoxy)-benzyl)-1H-indol-5-yl)acrylamide as an amorphous solid, yield 42%.

Example 9 N-(1-(3-iodobenzyl)-1H-indol-5-yl)acrylamide 1-(3-iodobenzyl)-1H-indol-5-amine (280 mg, 745 μmol) were solubilized in dichloro-methane (7 ml) with $Et_3N$ (220 μl, 1.50 mmol), cooled down to 0° C. before adding acryloyl chloride (73 μl, 900 μmol). Stirring was continued for 1 h at RT. The reaction mixture was diluted with DCM, extracted with water, dried over $Na_2SO_4$, evaporated at reduced pressure and purified by column chromatography (silica gel, gradient heptane/AcOEt 100/0 to 70/30) to obtain 90 mg of N-(1-(3-iodobenzyl)-1H-indol-5-yl)acrylamide as an amorphous solid, yield 24%.

Example 10 N-(1-(2-fluoro-5-(trifluoromethyl)benzyl)-1H-indol-5-yl)acrylamide 1-(2-fluoro-5-(trifluoromethyl)benzyl)-1H-indol-5-amine (200 mg, 645 μmol) were solubilized in DCM (5 ml) with $Et_3N$ (118 μl, 844 μmol), cooled down to 0° C. before adding acryloyl chloride (74 mg, 779 μmol). Stirring was continued for 3 h at RT. The reaction mixture was diluted with DCM, extracted with water, dried over $Na_2SO_4$, evaporated at reduced pressure and purified by column chromatography (silica gel, gradient heptane/AcOEt 100/0 to 50/50) to obtain 49 mg of N-(1-(2-fluoro (trifluoromethyl)benzyl)-1H-indol-5-yl)acrylamide as a beige solid, yield 21%.

Example 11 N-(3-methyl-1-(3-(trifluoromethynbenzyl)-1H-indol-5-yl)acrylamide 3-methyl-1-(3-(trifluoromethyl)benzyl)-1H-indol-5-amine (200 mg, 657 μmol) were solubilized in DCM (5 ml) with $Et_3N$ (110 μl, 789 μmol), cooled down to 0° C. before adding acryloyl chloride (74 mg, 789 μmol). Stirring was continued for 2 h at RT. The reaction mixture was diluted with $CH_2Cl_2$, extracted with water, dried over $Na_2SO_4$, evaporated at reduced pressure and purified by column chromatography (silica gel, gradient heptane/AcOEt 100/0 to 50/50) to obtain 28 mg of N-(1N-(3-methyl-1-(3-(trifluoromethyl)benzyl)-1H-indol-5-yl)acrylamide as a white solid after trituration in diethylether, yield 11%.

Example 12 N-(1-(3-methoxybenzyl)-1H-indol-5-yl)acrylamide 1-(3-methoxybenzyl)-1H-indol-5-amine (227 mg, 900 μmol) were solubilized in dichloro-methane (5 ml) with $Et_3N$ (190 μl, 1.08 mmol), cooled down to 0° C. before adding acryloyl chloride (80 μl, 950 μmol). Stirring was continued for 40 min at 0° C. The reaction mixture was diluted with DCM, extracted with water, dried over $Na_2SO_4$, evaporated at reduced pressure and purified by column chromatography (silica gel, gradient heptane/AcOEt 100/0 to 50/50) to obtain after trituration in AcOEt 45 mg of N-(1-(3-methoxybenzyl)-1H-indol-5-yl)acrylamide as a white solid, yield 16%.

Example 13 N-(2-methyl-1-(3-(trifluoromethynbenzyl)-1H-indol-5-yl)acrylamide 2-methyl-1-(3-(trifluoromethyl)benzyl)-1H-indol-5-amine (200 mg, 657 μmol) were solubilized in DCM (2 ml) with $Et_3N$ (138 μl, 986 μmol), cooled down to 0° C. before adding acryloyl chloride (74 mg, 789 μmol). Stirring was continued for 3 h at RT. The reaction mixture was diluted with DCM, extracted with water, dried over $Na_2SO_4$, evaporated at reduced pressure and purified by column chromatography (silica gel, gradient heptane/AcOEt 100/0 to 50/50) to obtain after trituration in diethylether 30 mg of N-(2-methyl-1-(3-(trifluoromethyl)benzyl)-1H-indol-5-yl)acrylamide as a white solid, yield 12%.

Example 14 N-(3-cyano-1-(3-(trifluoromethynbenzyl)-1H-indol-5-yl)acrylamide 5-amino-1-(3-(trifluoromethyl)benzyl)-1H-indole-3-carbonitrile (230 mg, 730 μmol) were solubilized in DCM (2 ml) with $Et_3N$ (153 μl, 1.09 mmol)), cooled down to 0° C. before adding acryloyl chloride (83 mg, 875 μmol). Stirring was continued for 1 h30 at RT. The reaction mixture was diluted with DCM, extracted with water, dried over $Na_2SO_4$, evaporated at reduced pressure and purified by column chromatography (silica gel, gradient heptane/AcOEt 100/0 to 50/50) to obtain after trituration in DCM 69 mg of N-(3-cyano-1-(3-(trifluoromethyl)benzyl)-1H-indol-5-yl)acrylamide as a beige solid, yield 25%.

Example 15 N-(1-(3-cyclopropylbenzyl)-1H-indol-5-yl)acrylamide 1-(3-cyclopropylbenzyl)-1H-indol-5-amine (170 mg, 647 μmol) were solubilized in DCM (2.5 ml) with $Et_3N$ (108 μl, 778 μmol) cooled down to 0° C. before adding acryloyl chloride (60 μl, 713 μmol). Stirring was continued for 30 min at 0° C. The reaction mixture was diluted with DCM, extracted with water, dried over $Na_2SO_4$, evaporated at reduced pressure and purified by column chromatography (silica gel, gradient heptane/AcOEt 95/5 to 60/40) to obtain after trituration in diethylether 40 mg of N-(1-(3-cyclopropylbenzyl)-1H-indol-5-yl)acrylamide as a white solid, yield 20%.

Example 16 N-(2,3-dimethyl-1-(3-(trifluoromethynbenzyl)-1H-indol-5-yl)acrylamide 2,3-dimethyl-1-(3-(trifluoromethyl)benzyl)-1H-indol-5-amine (200 mg, 628 μmol) were solubilized in DCM (2 ml) with $Et_3N$ (131 μl, 942 μmol), cooled down to 0° C. before adding acryloyl chloride (71 mg, 754 μmol). Stirring was continued for 2 h at RT. The reaction mixture was diluted with DCM, extracted with water, dried over $Na_2SO_4$, evaporated at reduced pressure and purified by column chromatography (silica gel, gradient heptane/AcOEt 100/0 to 50/50) to obtain after trituration in diethylether 33 mg of N-(2,3-dimethyl-1-(3-(trifluoromethyl)benzyl)-1H-indol-5-yl)acrylamide as a beige solid, yield 14%.

Example 17 N-(1-(3-methylbenzyl)-1H-indol-5-yl)acrylamide 1-(3-methylbenzyl)-1H-indol-5-amine (388 mg, 1.64 mmol) were solubilized in dichloro-methane (16 ml) with $Et_3N$ (344 μl, 1.97 mmol) cooled down to 0° C. before adding acryloyl chloride (160 μl, 1.97 mmol). Stirring was continued for 45 min at 0° C. The reaction mixture was diluted with DCM, extracted with water, dried over $Na_2SO_4$, evaporated at reduced pressure and purified by column chromatography (silica gel, gradient cyclo-hexane/AcOEt 100/0 to 50/50) to obtain 252 mg of N-(1-(3-methyl-benzyl)-1H-indol-5-yl)acrylamide as a pink solid, yield 53%.

Example 18 N-(1-Benzyl-1H-indol-5-yl)-acrylamide 1-benzyl-1H-indol-5-amine (30 mg, 140 μmol) were solubilized in DCM (2 ml) with $Et_3N$ (28 μl, 160 μmol) cooled down to 0° C. before adding acryloyl chloride (13 μl, 160 μmol). Stirring was continued for 45 min at 0° C. The reaction mixture was diluted with DCM, extracted with water, dried over $Na_2SO_4$, evaporated at reduced pressure and purified by column chromatography (silica gel, gradient heptane/AcOEt 100/0 to 50/50) to obtain 6 mg of N-(1-Benzyl-1H-indol-5-yl)acrylamide as a solid, yield 16%.

Example 19 N-(1-(3-(trifluoromethynbenzyl)-1H-indol-4-yl)acrylamide 1-(3-(trifluoromethyl)benzyl)-1H-indol-4-amine (150 mg, 517 μmol) were solubilized in DCM (2 ml) with $Et_3N$ (108 μl, 776 μmol), cooled down to 0° C. before adding acryloyl chloride (56 mg, 621 μmol). Stirring was continued for 3 h at RT. The reaction mixture was diluted with DCM, extracted with water, dried over $Na_2SO_4$, evaporated at reduced pressure and purified by column chromatography (silica gel, gradient heptane/AcOEt 100/0 to 50/50) to obtain after trituration in diethylether 95 mg of N-(1-(3-(trifluoromethyl)benzyl)-1H-indol-4-yl)acrylamide as a white solid, yield 51%.

Example 20 (E)-4-(dimethylamino)-N-(1-(3-(trifluoromethyl)benzyl)-1H-indol-4-yl)but-2-enamide (E)-4-dimethylaminocrotonic acid hydrochloride (176 mg, 1.03 mmol) were suspended in DCM (8 ml) with a catalytic amount of DMF (11 μl, 138 μmol), cooled down to 0° C. before adding oxalyl chloride (121 μl, 1.38 mmol). Stirring was continued for 2 h at RT. The reaction mixture was evaporated at reduced pressure. The crude (E)-4-(dimethylamino)but-2-enoyl chloride was used as that in the further step:

1-(3-(trifluoromethyl)benzyl)-1H-indol-4-amine (200 mg, 689 μmol) was solubilized in DCM (5 ml) with pyridine (223 μl, 2.76 mmol), cooled down to 0° C. before adding the previously prepared (E)-4-(dimethylamino)but-2-enoyl chloride diluted in DCM (5 ml). Stirring was continued for 3 h at RT. The reaction mixture was diluted with DCM, extracted with water, dried over $Na_2SO_4$, evaporated at reduced pressure and purified by column chromatography (silica gel, gradient $CH_2Cl_2$/MeOH 100/0 to 95/5) to obtain 76 mg of (E) (dimethylamino)-N-(1-(3-(trifluoromethyl) benzyl)-1H-indol-4-yl)but-2-enamide as a white solid, yield 27%.

Example 21 N-(1-(3-(trifluoromethynbenzyl)-1H-indol-6-yl)acrylamide 1-(3-(trifluoromethyl)benzyl)-1H-indol-6-amine (150 mg, 517 μmol) were solubilized in DCM (2 ml) with $Et_3N$ (94 μl, 672 μmol), cooled down to 0° C. before adding acryloyl chloride (59 mg, 620 μmol). Stirring was continued for 4 h at RT. The reaction mixture was diluted with DCM, extracted with water, dried over $Na_2SO_4$, evaporated at reduced pressure and purified by column chromatography (silica gel, gradient heptane/AcOEt 100/0 to 50/50) to obtain 110 mg of N-(1-(3-(trifluoromethyl)-benzyl)-1H-indol-6-yl) acrylamide as a white solid, yield 62%.

Example 22 N-(1((4,4-difluorocyclohexyl)methyl)-1H-indol-5-yl)acrylamide 1-((4,4-difluorocyclohexyl)methyl)-1H-indol-5-amine (101 mg, 382 μmol) were solubilized in DCM (4 ml) with $Et_3N$ (80 μl, 459 μmol) cooled down to 0° C. before adding acryloyl chloride (38 μl, 459 μmol). Stirring was continued for 45 min at 0° C. The reaction mixture was diluted with DCM, extracted with water, dried over $Na_2SO_4$, evaporated at reduced pressure and purified by column chromatography (silica gel, gradient cyclohexane/AcOEt 100/100 to 50/50) to obtain 61 mg of N-(1-((4,4-di-fluorocyclohexyl)methyl)-1H-indol-5-yl)acrylamide as a white solid, yield 50%.

Example 23 N-(1-((tetrahydro-2H-pyran-4-yl) methyl)-1H-indol-5-yl)acrylamide 1-((tetrahydro-2H-pyran-4-yl)methyl)-1H-indol-5-amine (138 mg, 599 μmol) were solubilized in DCM (6 ml) with $Et_3N$ (126 μl, 719 μmol) cooled down to 0° C. before adding acryloyl chloride (58 μl, 718 μmol). Stirring was continued for 45 min at 0° C. The reaction mixture was diluted with DCM, extracted with water, dried over $Na_2SO_4$, evaporated at reduced pressure and purified by column chromatography (silica gel, gradient DCM/MeOH 100/0 to 95/5) to obtain 106 mg of N-(1-((tetrahydro-2H-pyran-4-yl)methyl)-1H-indol-5-yl)acrylamide as a white solid, yield 62%.

Example 24 N-(1-((4-(trifluoromethyl)cyclohexyl) methyl)-1H-indol-5-yl)acrylamide 1-((4-(trifluoromethyl)cyclohexyl)methyl)-1H-indol-5-amine (114 mg, 384 μmol) were solubilized in DCM (4 ml) with $Et_3N$ (81 μl, 461 μmol) cooled down to 0° C. before adding acryloyl chloride (38 μl, 461 μmol). Stirring was continued for 45 min at 0° C. The reaction mixture was diluted with DCM, extracted with water, dried over $Na_2SO_4$, evaporated at reduced pressure and purified by column chromatography (silica gel, gradient cyclohexane/AcOEt 100/0 to 50/50) to obtain 70 mg of N-(1-((4-(trifluoromethyl)-cyclohexyl)methyl)-1H-indol-5-yl)acrylamide as a pink solid, yield 52%.

Example 25 N-(1-((1,1-difluorospiro[2.3]hexan-5-yl)methyl)-1H-indol-5-yl)acrylamide 1-((1,1-difluorospiro[2.3]hexan-5-yl)methyl)-1H-indol-5-amine (110 mg, 419 μmol) were solubilized in DCM (2 ml) with $Et_3N$ (70 μl, 503 μmol) cooled down to 0° C. before adding acryloyl chloride (38 μl, 461 μmol). Stirring was continued for 30 min at 0° C. The reaction mixture was diluted with $CH_2Cl_2$, extracted with water, dried over $Na_2SO_4$, evaporated at reduced pressure and purified by column chromatography (silica gel, gradient heptane/AcOEt) to obtain after trituration in diethylether 75 mg of N-(1-((1,1-difluorospiro[2.3]hexan-5-yl)methyl)-1H-indol-5-yl)acrylamide as a solid, yield 57%.

Example 26 N-(1((3-fluorocyclopentyl)methyl)-1H-indol-5-yl)acrylamide 1-((3-fluorocyclopentyl)methyl)-1H-indol-5-amine (130 mg, 560 μmol) were solubilized in DCM (2 ml) with $Et_3N$ (94 μl, 672 μmol) cooled down to 0° C. before adding acryloyl chloride (52 μl, 616 μmol). Stirring was continued for 30 min at 0° C. The reaction mixture was diluted with DCM, extracted with water, dried over $Na_2SO_4$, evaporated at reduced pressure and purified by column chromatography (silica gel, gradient heptane/AcOEt 95/5 to 60/40) to obtain after trituration in diethylether 72 mg of N-(1-((3-fluorocyclopentyl)methyl)-1H-indol-5-yl)acrylamide as a solid, yield 45%.

Example 27
N-(1-(cyclohexylmethyl)-1H-indol-5-yl)acrylamide 1-(cyclohexylmethyl)-1H-indol-5-amine (260 mg, 1.14 mmol) were solubilized in DCM (10 ml) with $Et_3N$ (218.76 μl, 1.25 mmol), cooled down to 0° C. before adding acryloyl chloride (97 μl, 1.20 mmol). Stirring was continued for 45 min at 0° C. The reaction mixture was diluted with $CH_2Cl_2$, extracted with water, dried over $Na_2SO_4$, evaporated at reduced pressure and purified by column chromatography (silica gel, gradient heptane/AcOEt 100/0 to 50/50) to obtain after trituration in AcOEt 77 mg of N-(1-(cyclohexylmethyl)-1H-indol-5-yl)acrylamide as a solid, yield 24%.

Example 28 N-(1-((3-(trifluoromethyl)cyclobutyl) methyl)-1H-indol-5-yl)acrylamide 1-((3-(trifluoromethyl)cyclobutyl)methyl)-1H-indol-5-amine (138 mg, 514 μmol) were solubilized in DCM (2 ml) with $Et_3N$ (86 μl, 617 μmol), cooled down to 0° C. before adding acryloyl chloride (48 μl, 566 μmol). Stirring was continued for 45 min at 0° C. The reaction mixture was diluted with DCM, extracted with water, dried over $Na_2SO_4$, evaporated at reduced pressure and purified by column chromatography (silica gel, gradient heptane/AcOEt 95/5 to 60/40) to obtain after trituration in diethylether 47 mg of N-(1-((3-(trifluoromethyl)cyclobutyl)methyl)-1H-indol-5-yl)acrylamide as a solid, yield 28%.

Example 29 N-(1-((3,3-difluorocyclopentynmethyl)-1H-indol-5-yl)acrylamide 1-((3,3-difluorocyclopentyl)methyl)-1H-indol-5-amine (67 mg, 268 μmol) were solubilized in DCM (2 ml) with $Et_3N$ (45 μl, 321 μmol), cooled down to 0° C. before adding acryloyl chloride (25 μl, 295 μmol). Stirring was continued for 1 h at 0° C. The reaction mixture was diluted with DCM, extracted with water, dried over $Na_2SO_4$, evaporated at reduced pressure and purified by column chromatography (silica gel, gradient heptane/AcOEt 95/5 to 60/40) to obtain 34 mg of N-(1-((3,3-difluorocyclo-pentyl)methyl)-1H-indol-5-yl)acrylamide as a solid, yield 42%.

Diaryl-derivatives were introduced either via the already described alkylation in step 1 of the general scheme (see example 30) or as a variation of the general synthetic scheme where a Suzuki coupling-step allows the synthesis of the corresponding diaryl-derivatives for non-commercially available building-blocks (see example 31) after the first step of the general scheme.

Example 30 N-(1-([1,1'-biphenyl]-4-ylmethyl)-1H-indol-5-yl)acrylamide 1-([1,1-biphenyl]-4-ylmethyl)-1H-indol-5-amine (106 mg, 355 μmol) were solubilized in DCM (5 ml) with $Et_3N$ (74 μl, 533 μmol), cooled down to 0° C. before adding acryloyl chloride (40 mg, 426 μmol). Stirring was continued for 2 h at RT. The reaction mixture was diluted with DCM, extracted with water and an aqueous saturated solution of NaCl, dried over $Na_2SO_4$, evaporated at reduced pressure and purified by column chromatography (silica gel, gradient heptane/AcOEt 100/0 to 70/30) to obtain 56 mg of N-(1-([1,1-biphenyl]ylmethyl)-1H-indol-5-yl)acrylamide as a white solid, yield 42%.

Example 31 N-(1-((3'-(trifluoromethyl)-[1,1-biphenyl]-4-yl)methyl)-1H-indol-5-yl)-acrylamide

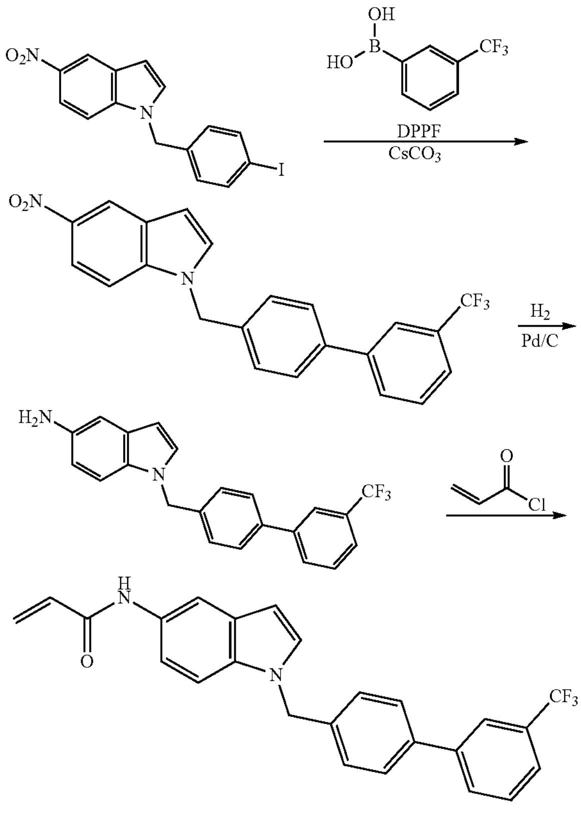

1-(4-iodobenzyl)-5-nitro-1H-indole was synthesized as described in example 1 (step 1).

5-nitro-1-[[4-[3-(trifluoromethyl)phenyl]phenyl]methyl]indole

To a suspension of 1-(4-iodobenzyl)-5-nitro-1H-indole (300 mg, 793 μmol) in 1,4-dioxane (5 ml) and water (1 ml) were added 3-(trifluoromethyl)phenylboronic acid (158 mg, 793 μmol), cesium carbonate (516 mg, 1.59 mmol), DPPF (22 mg, 40 μmol) and $PdCl_2(PPh_3)_2$ (28 mg, 40 μmol), the mixture was heated to 80° C. (all components were solubilized at this temperature), stirring was continued for 4 h at 80° C. The reaction mixture was diluted with AcOEt, extracted with water and an aqueous saturated solution of NaCl, dried over $Na_2SO_4$, evaporated at reduced pressure and purified by column chromatography (silica gel, gradient heptane/AcOEt 100/0 to 75/25) to obtain 253 mg of 5-nitro-1-[[4-[3-(trifluoromethyl)phenyl]-phenyl]methyl]indole as a yellow resin, yield 90%.

1-([1,1-biphenyl]-4-ylmethyl)-1H-indol-5-amine was synthesized and purified as described in example 1 (step 2).

N-(1-([1,1-biphenyl]-4-ylmethyl)-1H-indol-5-yl)acrylamide 1-((3'-(trifluoromethyl)-[1,1-biphenyl]-4-yl)methyl)-1H-indol-5-amine (188 mg, 513 μmol) were solubilized in DCM (5 ml) with $Et_3N$ (86 μl, 616 μmol), cooled down to 0° C. before adding acryloyl chloride (58 mg, 616 μmol). Stirring was continued for 2 h at RT. The reaction mixture was diluted with DCM, extracted with water and an aqueous saturated solution of NaCl, dried over $Na_2SO_4$, evaporated at reduced pressure and purified by column chromatography (silica gel, gradient heptane/AcOEt 100/0 to 50/50) to obtain 31 mg of N-(1-((3'-(trifluoromethyl)-[1,1'-biphenyl]-4-yl)methyl)-1H-indol-5-yl)acryl-amide (example 31) as a white solid, yield 14%.

Example 32 N-(1-((4'-(trifluoromethyl)-[1,1'-biphenyl]-4-yl)methyl)-1H-indol-5-yl)-acrylamide 1-((4'-(trifluoromethyl)-[1,1'-biphenyl]-4-yl)methyl)-1H-indol-5-amine (158 mg, 431 μmol) were solubilized in DCM (5 ml) with $Et_3N$ (72 μl, 518 μmol), cooled down to 0° C. before adding acryloyl chloride (49 mg, 518 μmol). Stirring was continued for 1 h at RT. The reaction mixture was diluted with DCM, extracted with water, dried over $Na_2SO_4$, evaporated at reduced pressure and purified by column chromatography (silica gel, gradient DCM/MeOH 100/0 to 95/5) to obtain after trituration in DCM 60 mg of N-(1-((4'-(trifluoromethyl)-[1,1-biphenyl]-4-yl)methyl)-1H-indol-5-yl)acrylamide as a white solid, yield 30%.

An alternative for step 1 in scheme 2 is represented in the following example. A Mitsunobu reaction approach was used with primary or secondary alcohols as starting materials. Step 2 and 3 were realized in the same manner as illustrated in preceding schemes.

Example 33 Trans-N-[1-[4-(trifluoromethyl)cyclohexyl]indol-5-yl]acrylamide and Example 34 Cis-N-[1-[4-(trifluoromethyl)cyclohexyl]indol-5-yl]acrylamide

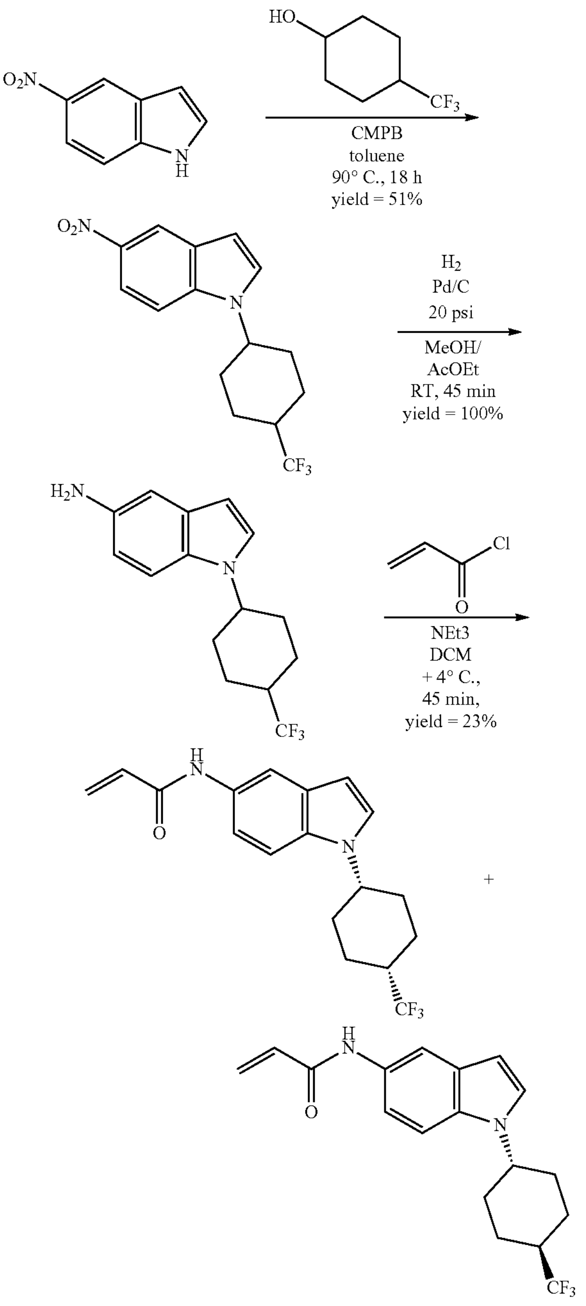

5-nitro-1-[4-(trifluoromethyl)cyclohexyl]indole 4-(trifluoromethyl)cyclohexanol (341 μl, 2.42 mmol) was introduced under nitrogen in toluene (30 ml), and 5-nitroindole (200 mg, 1.21 mmol) and CMPB (988 μl, 3.63 mmol) were added sequentially. The resulting mixture was heated at 90° C. for 18 h and was stirred at RT for the following 24 h and then diluted by AcOEt and washed two times by water and two times by an aqueous saturated solution of NaCl. The organic layer was dried over solid $Na_2SO_4$ and the solvent was removed under reduced pressure to afford after column chromatography purification (silica gel, eluant DCM/MeOH 100/0 to 99/1) 194 mg of 5-nitro-1-[4-(trifluoromethyl) cyclohexyl]indole as a solid, yield 51%.

1-(4-(trifluoromethyl)cyclohexyl)-1H-indol-5-amine 5-nitro-1-(4-(trifluoromethyl)cyclohexyl)-1H-indole (194 mg, 621 μmol) were solubilized in 5 ml of methanol and 5 ml of AcOEt, Pd/C 10% (50% wet) (66 mg) was added and the mixture was hydrogenated in a Parr apparatus at RT under 20 psi hydrogen pressure for 45 min. After filtration and evaporation at reduced pressure, 180 mg of 1-(4-(trifluoro-methyl)cyclohexyl)-1H-indol-5-aminewere obtained and used without further purification, raw yield 100%.

N-[1-[4-(trifluoromethyl)cyclohexyl]indol-5-yl]acrylamide 1-(4-(trifluoromethyl)cyclohexyl)-1H-indol-5-amine (175 mg, 620 μmol) were solubilized in DCM (2 ml) with $Et_3N$ (104 μl, 744 μmol), cooled down to 0° C. before adding acryloyl chloride (57 μl, 682 μmol). Stirring was continued for 45 min at RT. The reaction mixture was diluted with DCM, extracted with water, dried over $Na_2SO_4$, evaporated at reduced pressure and purified by column chromatography (silica gel, gradient heptane/AcOEt 95/5 to 60/40) to obtain 23 mg of cis-N-[1-[4-(trifluoromethyl)cyclohexyl]indol-5-yl]acrylamide (example 33) as a white solid (yield 7%) and after further trituration in diethylether 52 mg of trans-N-[1-[4-(trifluoromethyl)-cyclohexyl]indol-5-yl]acrylamide (example 34) as a white powder (yield 16%).

The following compounds were synthesized in a similar manner as example 33 and 34 by using the appropriate indoles and primary or secondary alcohols as starting materials known to those skilled in the art.

Example 35 N-(1-((1-(4-(trifluoromethyl)phenyl) piperidin-4-yl)methyl)-1H-indol-5-yl)-acrylamide 1-((1-(4-(trifluoromethyl)phenyl)piperidin-4-yl)methyl)-1H-indol-5-amine (280 mg, 900 μmol) were solubilized in DCM (7 ml) with $Et_3N$ (220 μl, 1.50 mmol), cooled down to 0° C. before adding acryloyl chloride (73 μl, 1.1 mmol). Stirring was continued for 1 h at RT. The reaction mixture was diluted with DCM, extracted with water, dried over $Na_2SO_4$, evaporated at reduced pressure and purified by column chromatography (silica gel, gradient heptane/AcOEt 100/0 to 70/30) to obtain 30 mg of a foam (80% purity) further purified via reversed phase column chromatography to obtain 12 mg of N-(1-((1-(4-(trifluoromethyl)phenyl) piperidin-4-yl)methyl)-1H-indol-5-yl)-acrylamide as an amorphous solid, yield 3.7%.

Example 36 N-(1-(2-(methyl(2,2,2-trifluoroethyl) amino)ethyl)-1H-indol-5-yl)acryl-amide 1-(2-(methyl(2,2,2-trifluoroethyl)amino)ethyl)-1H-indol-5-amine (150 mg, 550 μmol) were solubilized in DCM (2 ml) with $Et_3N$ (120 μl, 830 μmol), cooled down to 0° C. before adding acryloyl chloride (56 μl, 660 μmol). Stirring was continued for 2 h at RT. The reaction mixture was diluted with DCM, extracted with water, dried over $Na_2SO_4$, evaporated at reduced pressure and purified by column chromatography (silica gel, gradient heptane/AcOEt 100/0 to 50/50) to obtain after trituration in pentane86 mg of N-(1-(2-(methyl(2,2,2-trifluoroethyl)amino)ethyl)-1H-indol-5-yl)acrylamide as a pale beige solid, yield 48%.

Example 37 N-(1-(2-(2,2,2-trifluoroethoxy)ethyl)-1H-indol-5-yl)acrylamide 1-(2-(2,2,2-trifluoroethoxy)ethyl)-1H-indol-5-amine (224 mg, 0.87 mmol) were solubilized in DCM (5 ml) with $Et_3N$ (180 μl, 1.3 mmol), cooled down to 0° C. before adding acryloyl chloride (88 μl, 1.04 mmol). Stirring was continued for 4 h at RT. The reaction mixture was diluted with DCM, extracted with water, dried over $Na_2SO_4$, evaporated at reduced pressure and purified by column chromatography (silica gel, gradient heptane/AcOEt 100/0 to 50/50) to obtain after trituration in diethylether 64 mg of N-(1-(2-(2,2,2-trifluoroethoxy)ethyl)-1H-indol-5-yl)acrylamide as a white solid, yield 23%.

Example 38 N-(1-(1-(2,2,2-trifluoroethyl)piperidin-4-yl)-1H-indol-5-yl)acrylamide 1-(1-(2,2,2-trifluoroethyl)piperidin-4-yl)-1H-indol-5-amine (73 mg, 246 μmol) were solubilized in DCM (3 ml) with $Et_3N$ (72 μl, 491 μmol), cooled down to 0° C. before adding acryloyl chloride (24 μl, 295 μmol). Stirring was continued for 1 h at RT. The reaction mixture was diluted with DCM, extracted with water, dried over $Na_2SO_4$, evaporated at reduced pressure and purified by column chromatography (silica gel, gradient heptane/AcOEt 100/0 to 70/30) to obtain 20 mg of N-(1-(1-(2,2,2-trifluoro-ethyl)-piperidin-4-yl)-1H-indol-5-yl)acrylamide as an amorphous solid, yield 23%.

Example 39 N-(1-(4,4-difluorocyclohexyl)-1H-indol-5-yl)acrylamide 1-(4,4-difluorocyclohexyl)-1H-indol-5-amine (134 mg, 540 μmol) were solubilized in DCM (3 ml) with $Et_3N$ (90 μl, 640 μmol), cooled down to 0° C. before adding acryloyl chloride (88 μl, 1.04 mmol). Stirring was continued for 15 min at 0° C. The reaction mixture was diluted with DCM, extracted with water, dried over $Na_2SO_4$, evaporated at reduced pressure and purified by column chromatography (silica gel, gradient heptane/AcOEt 95/5 to 60/40) to obtain 42 mg of N-(1-(2-(2,2,2-trifluoro-ethoxy)ethyl)-1H-indol-5-yl)acrylamide as a powder, yield 68%.

Example 40 N-(1-(1-(4-(trifluoromethyl)phenyl) piperidin-4-yl)-1H-indol-5-yl)acryl-amide 1-(1-(4-(trifluoromethyl)phenyl)piperidin-4-yl)-1H-indol-5-amine (60 mg, 167 μmol) was solubilized in DCM (2 ml) with $Et_3N$ (28 μl, 200 μmol), cooled down to 0° C. before adding acryloyl chloride (16 μl, 184 μmol). Stirring was continued for 30 min at 0° C. The reaction mixture was diluted with DCM, extracted with water and an aqueous saturated solution of NaCl, dried over $Na_2SO_4$, evaporated at reduced pressure and purified by column chromatography (silica gel, gradient heptane/AcOEt 95/5 to 60/40) to obtain 32 mg of N-(1-(1-(4-(trifluoromethyl)phenyl)piperidin-4-yl)-1H-indol-5-yl)acrylamide as a white powder, yield 51%.

Another variation of the general approach is represented in the following example 41 where a halogenated alcohol is introduced in the first step via the already described Mitsunobu-reaction followed by further substitution by a secondary amine.

Example 41 N-(1-(3-(3,3-difluoropyrrolidin-1-yl)propyl)-1H-indol-5-yl)acrylamide

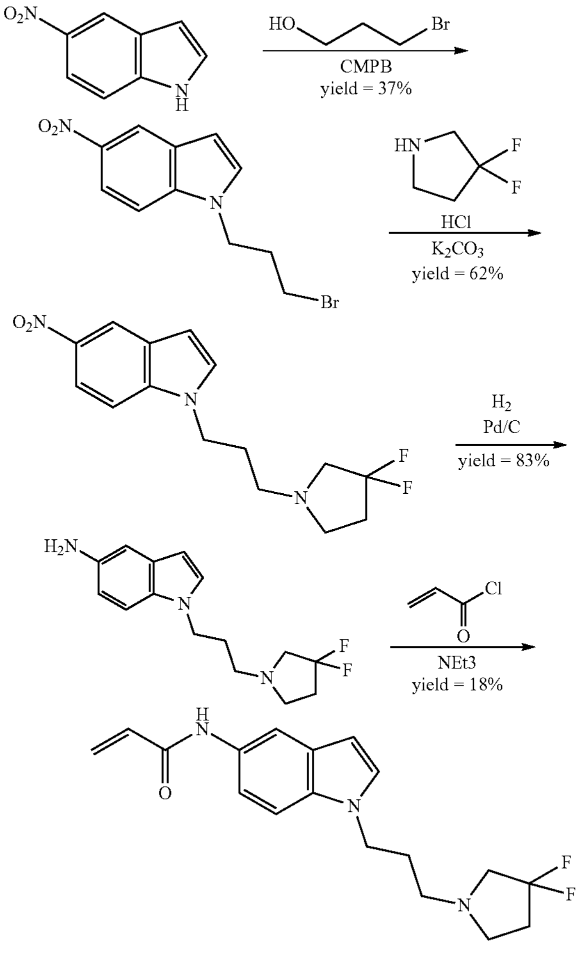

1-(3-bromopropyl)-5-nitro-1H-indole 5-nitroindole (1 g, 6.04 mmol) were solubilized in toluene (100 ml) before adding 3-bromo-1-propanol (1.77 g, 12.09 mmol) et CMPB (4.61 g, 18.13 mmol). The mixture was heated at 100° C. for 2 h, cooled to RT, diluted with AcOEt, washed with water and an aqueous saturated solution of NaCl, dried over sodium sulfate and concentrated under reduced pressure. Purification by column chromatography on silica gel (eluant heptane/AcOEt 100/0 to 50/50) provided 2.2 g of a yellow solid, yield 37%.

1-(3-(3,3-difluoropyrrolidin-1-yl)propyl)-5-nitro-1H-indole 3,3-difluoropyrrolidine hydrochloride (136 mg, 918 μmol), potassium carbonate (225 mg, 1.62 mmol) and 1-(3-bromopropyl)-5-nitro-1H-indole (200 mg, 706 μmol) were solubilized in acetonitrile (5 ml). The mixture was heated at 70° C. overnight, then cooled to RT, poured into water and extracted with AcOEt. The organic layer was dried over sodium sulfate and concentrated under reduced pressure. The residue was purified by column chromatography on silica gel (eluant heptane/AcOEt 100/0 to 50/50) to obtain 136 mg of 1-(3-(3,3-difluoropyrrolidin-1-yl)propyl)-5-nitro-1H-indole as a yellow oil, yield 62%.

1-(3-(3,3-difluoropyrrolidin-1-yl)propyl)-1H-indol-5-amine 1-(3-(3,3-difluoropyrrolidin-1-yl)propyl)-5-nitro-1H-indole (136 mg, 440 μmol) were solubilized in MeOH (10 ml). Pd/C 10% (50% wet) (47 mg, 22 μmol) was added and the mixture was hydrogenated in a Parr apparatus at RT under 20 psi hydrogen pressure for 2 h. After filtration and evaporation under reduced pressure, 100 mg of a pinky colored oil were obtained and used without further purification in the next step, yield 81%.

N-(1-(3-(3,3-difluoropyrrolidin-1-yl)propyl)-1H-indol-5-yl)acrylamide (Example 41)

1-(3-(3,3-difluoropyrrolidin-1-yl)propyl)-1H-indol-5-amine (100 mg, 358 μmol) were solubilized in DCM (2 ml) with $Et_3N$ (75 μl, 537 μmol), cooled down to 0° C. before adding acryloyl chloride (36 μl, 430 μmol). Stirring was continued for 2 h at RT. The reaction mixture was diluted with DCM, extracted with water, dried over $Na_2SO_4$, evaporated at reduced pressure and purified by column chromatography (silica gel, gradient heptane/AcOEt 100/0 to 50/50) to obtain after trituration in diethylether 22 mg of N-(1-(3-(3,3-difluoropyrrolidin-1-yl)propyl)-1H-indol-5-yl)acrylamide as a solid, yield 18%.

The following example presents an alternative for the reduction of the nitro-group (step 2 of scheme 2) in order to tolerate functional groups sensitive to catalytic hydrogenation.

Example 42 N-(1-(4-(trimethylsilynbenzyl)-1H-indol-5-yl)acrylamide

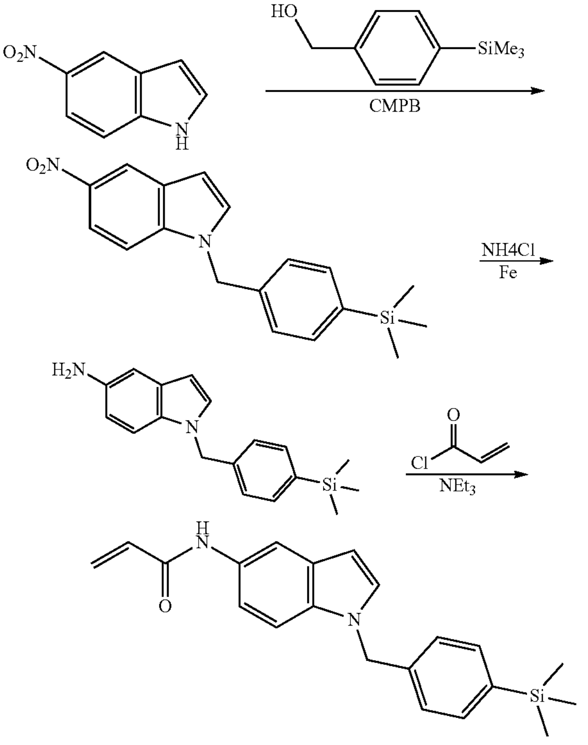

5-nitro-1-(4-(trimethylsilyl)benzyl)-1H-indole 4-(trimethylsilyl)phenyl)methanol (556 mg, 3.08 mmol) was introduced under nitrogen in toluene (15 ml). 5-nitroindole (250 mg, 1.54 mmol) and CMPB (1.3 ml, 4.63 mmol) were added sequentially. The resulting mixture was heated at 90° C. for 18 h and then diluted by AcOEt and washed two times with water and two times with an aqueous saturated solution of NaCl. The organic layer was dried over solid $Na_2SO_4$ and the solvent was removed under reduced pressure. After column chromatography purification (silica gel, eluant DCM/MeOH 100/0 to 99/1) 194 mg of 5-nitro-1-(4-(trimethylsilyl)benzyl)-1H-indole was obtained as a pale yellow solid, yield 51%.

1-(4-(trimethylsilyl)benzyl)-1H-indol-5-amine

To a solution of 5-nitro-1-(4-(trimethylsilyl)benzyl)-1H-indole (200 mg, 0.62 mmol) in 4.5 ml of ethanol and 1.5 ml of water were added ammonium chloride (87 mg, 1.54 mmol) and iron powder (87 mg, 1.54 mmol). The pale-yellow solution darkened rapidly and was heated under reflux for 2 h. After cooling down to RT 3 ml of water were added. The resulting gel was filtered through a Whatman filter-pad and rinsed with AcOEt. The aqueous layer was separated and extracted twice with AcOEt. The combined organic layers were washed with water and an aqueous saturated solution of NaCl, dried over $Na_2SO_4$ and evaporated under reduced pressure to obtain 110 mg of a gum used without further purification for the next step, raw yield 60%.

N-(1-(4-(trimethylsilyl)benzyl)-1H-indol-5-yl)acrylamide (example 42)

N-(1-(4-(trimethylsilyl)benzyl)-1H-indol-5-amine (105 mg, 36 μmol) were solubilized in DCM (6 ml) with $Et_3N$ (99 μl, 713 μmol) cooled down to 0° C. before adding acryloyl chloride (36 μl, 430 μmol). Stirring was continued for 18 h at RT. The reaction mixture was diluted with DCM, extracted with water, dried over $Na_2SO_4$, evaporated at reduced pressure and purified by column chromatography (silica gel, gradient heptane/AcOEt 100/0 to 70/30) to obtain 50 mg of N-(1-(4-(trimethylsilyl)-benzyl)-1H-indol-5-yl) acrylamide as a white solid, yield 36%.

Another sequence is illustrated in the following example where the first step of the general scheme is realized via an Ullmann-coupling by using iodo-aryl or iodo-hetero-aryl derivatives:

Example 43 N-(1-(3-(trifluoromethyl)phenyl)-1H-indol-5-yl)acrylamide

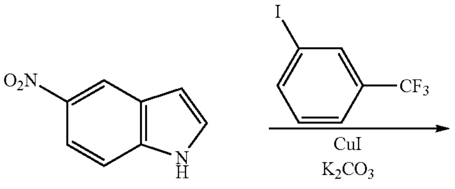

-continued

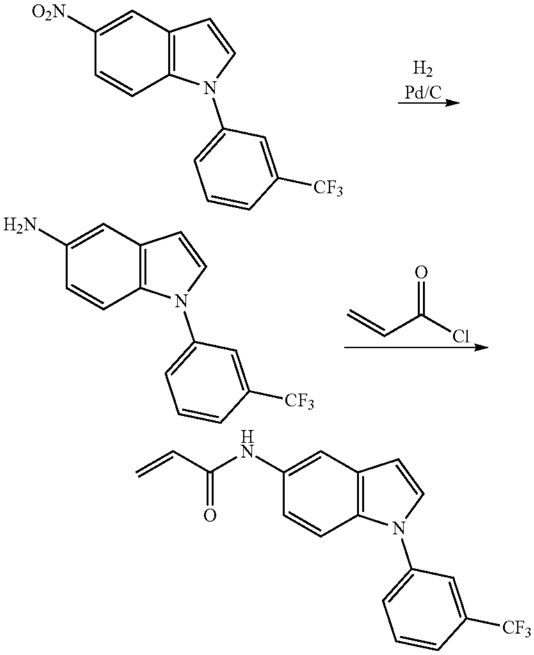

5-nitro-1-(3-(trifluoromethyl)phenyl)-1H-indole

As described in patent application US 2016/318864, 5-nitroindole (500 mg, 3.02 mmol), 1-iodo-3-(trifluoromethyl)benzene (536 μl, 3.02 mmol), DMEDA (331 μl, 3.05 mmol), copper(I) iodide (587 mg, 3.08 mmol) and potassium carbonate (852 mg, 6.16 mmol) were added in DMSO (5 ml) and heated at 140° C. for 6 h. AcOEt is added to the mixture and washed with water and with a saturated aqueous solution of NaCl. The organic layer is dried over $MgSO_4$. After filtration and evaporation of the solvent at reduced pressure, 850 mg of 5-nitro-1-(3-(trifluoromethyl)phenyl)-1H-indole were obtained and used without further purification, yield 92%.

1-(3-(trifluoromethyl)phenyl)-1H-indol-5-amine 5-nitro-1-(3-(trifluoromethyl)phenyl)-1H-indole (0.85 g, 2.78 mmol) were solubilized in 20 ml of MeOH and 5 ml of AcOEt, Pd/C 10% (50% wet) (30 mg) was added and the mixture was hydrogenated in a Parr apparatus at RT under 30 psi hydrogen pressure for 2 h. After filtration and evaporation at reduced pressure 714 mg of 1-(3-(trifluoromethyl)phenyl)-1H-indol-5-amine were obtained as a brown oil and used without further purification, yield 93%.

1-(3-(trifluoromethyl)phenyl)-1H-indol-5-amine (200 mg, 724 μmol) obtained in the step described above were solubilized in DCM (2 ml) with $Et_3N$ (121 μl, 869 μmol), cooled down to 0° C. before adding acryloyl chloride (82 mg, 869 μmol). Stirring was continued for 1 h30 at RT. The reaction mixture was diluted with DCM, extracted with water, dried over $Na_2SO_4$, evaporated at reduced pressure and purified by column chromatography (silica gel, gradient heptane/AcOEt 95/5 to 60/40) to obtain after trituration in diethylether, 102 mg of N-(1-(3-(trifluoromethyl)phenyl)-1H-indol-5-yl)acryl-amide (example 43) as a white solid, yield 42%.

The following compounds were synthesized in a similar manner as example 43 by using the appropriate indoles and iodo-aryl derivatives as starting materials known to those skilled in the art.

Example 44 N-(1-(4-(trifluoromethyl)phenyl)-1H-indol-5-yl)acrylamide 1-(4-(trifluoromethyl)phenyl)-1H-indol-5-amine (200 mg, 724 μmol) were solubilized in DCM (2 ml) with $Et_3N$ (121 μl, 869 μmol), cooled down to 0° C. before adding acryloyl chloride (82 mg, 869 μmol). Stirring was continued for 3 h at RT. The reaction mixture was diluted with DCM, extracted with water, dried over $Na_2SO_4$, evaporated at reduced pressure and purified by column chromatography (silica gel, gradient heptane/AcOEt 95/5 to 60/40) to obtain after trituration in diethylether, 105 mg of N-(1-(4-(trifluoromethyl)phenyl)-1H-indol-5-yl)acrylamide as a white solid, yield 42%.

Example 45 N-(1-(6-(trifluoromethyl)pyridin-3-yl)-1H-indol-5-yl)acrylamide 1-(6-(trifluoromethyl)pyridin-3-yl)-1H-indol-5-amine (173 mg, 603 μmol) were solubilized in DCM (5 ml) with DIEA (160 μl, 909 μmol), cooled down to 0° C. before adding acryloyl chloride (50 μl, 617 μmol). Stirring was continued overnight at RT. The reaction mixture was diluted with DCM, extracted with water, dried over $Na_2SO_4$, evaporated at reduced pressure and purified by column chromatography (silica gel, gradient cyclohexane/AcOEt 100/0 to 80/20) to obtain after trituration in diisopropylether, 67 mg of N-(1-(6-(trifluoro-methyl)-pyridin-3-yl)-1H-indol-5-yl) acrylamide as a white solid, yield 32%.

Example 46 N-(1-(5-(trifluoromethyl)pyridin-2-yl)-1H-indol-5-yl)acrylamide 1-(5-(trifluoromethyl)pyridin-2-yl)-1H-indol-5-amine (167 mg, 572 μmol) were solubilized in DCM (5 ml) with DIPA (160 μl, 909 μmol), cooled down to 0° C. before adding acryloyl chloride (50 μl, 617 μmol). Stirring was continued overnight at RT. The reaction mixture was diluted with DCM, extracted with water, dried over $Na_2SO_4$, evaporated at reduced pressure and purified by column chromatography (silica gel, gradient cyclohexane/AcOEt 100/0 to 80/20) to obtain after trituration in diisopropylether, 67 mg of N-(1-(5-(trifluoromethyl)pyridin-2-yl)-1H-indol-5-yl) acrylamide as a white solid, yield 35%.

Example 47 N-(1-(pyridin-3-yl)-1H-indol-5-yl)acrylamide 1-(pyridin-3-yl)-1H-indol-5-amine (224 mg, 867 μmol) were solubilized in dichloro-methane (5 ml) with DIPA (230 μl, 1.31 mmol), cooled down to 0° C. before adding acryloyl chloride (80 μl, 988 μmol). Stirring was continued overnight at RT. The reaction mixture was diluted with DCM, extracted with water, dried over $Na_2SO_4$, evaporated at reduced pressure and purified by column chromatography (silica gel, gradient cyclohexane/AcOEt 100/0 to 60/40) to obtain after trituration in diisopropyl-ether 136 mg of N-(1-(pyridin-3-yl)-1H-indol-5-yl)acrylamide as a white solid, yield 57%.

Example 48 N-(1-(4-fluorophenyl)-1H-indol-5-yl) acrylamide 1-(4-fluorophenyl)-1H-indol-5-amine (183 mg, 809 μmol) were solubilized in dichloro-methane (4 ml) with $Et_3N$ (169 μl, 1.21 mmol), cooled down to 0° C. before adding acryloyl chloride (92 mg, 971 μmol). Stirring was continued for 4 h at RT. The reaction mixture was diluted with DCM, extracted with water, dried over $Na_2SO_4$, evaporated at reduced pressure and purified by column chromatography (silica gel, gradient heptane/AcOEt 100/0 to 70/30) to obtain 38 mg of N-(1-(4-fluorophenyl)-1H-indol-5-yl)-acrylamide as a white solid, yield 17%.

Example 49 N-(1-(3,4-difluorophenyl)-1H-indol-5-yl)acrylamide 1-(3,4-difluorophenyl)-1H-indol-5-amine (310 mg, 1.27 mmol) were solubilized in DCM (4 ml) with $Et_3N$ (265 μl, 1.90 mmol), cooled down to 0° C. before adding acryloyl chloride (144 mg, 1.52 mmol). Stirring was continued for 4 h at RT. The reaction mixture was diluted with DCM, extracted with water, dried over $Na_2SO_4$, evaporated at reduced pressure and purified by column chromatography (silica gel, gradient heptane/AcOEt 100/0 to 70/30) to obtain 5 mg of N-(1-(3,4-difluorophenyl)-1H-indol-5-yl)acrylamide as a pale pink solid, yield 2%.

Example 50 N-(1-(3-(methylsulfonyl)phenyl)-1H-indol-5-yl)acrylamide 1-(3-(methylsulfonyl)phenyl)-1H-indol-5-amine (255 mg, 891 μmol) were solubilized in DCM (5 ml) with $Et_3N$ (186 μl, 1.34 mmol), cooled down to 0° C. before adding acryloyl chloride (101 mg, 1.07 mmol). Stirring was continued for 4 h at RT. The reaction mixture was diluted with DCM, extracted with water, dried over $Na_2SO_4$, evaporated at reduced pressure and purified by column chromatography (silica gel, gradient heptane/AcOEt 100/0 to 70/30) to obtain 115 mg of N-(1-(3-(methylsulfonyl)-phenyl)-1H-indol-5-yl) acrylamide as a white solid, yield 34%.

Example 51 N-(1-(4-cyanophenyl)-1H-indol-5-yl) acrylamide 4-(5-amino-1H-indol-1-yl)benzonitrile (32 mg, 137 μmol) were solubilized in dichloro-methane (3 ml) with $Et_3N$ (29 μl, 206 μmol), cooled down to 0° C. before adding acryloyl chloride (16 mg, 165 μmol). Stirring was continued for 2 h at RT. The reaction mixture was diluted with DCM, extracted with water, dried over $Na_2SO_4$, evaporated at reduced pressure and purified by column chromatography (silica gel, gradient heptane/AcOEt 100/0 to 60/40) to obtain 8 mg of N-(1-(4-cyanophenyl)-1H-indol-5-yl)acrylamide as a white solid, yield 20%.

The following examples were synthesized as already described in scheme 2.

Example 52 N-(1-(3,5-difluorobenzyl)-1H-indol-5-yl)acrylamide

To a solution of 1-(3,5-difluorobenzyl)-1H-indol-5-amine (297 mg, 1.09 mmol) in DCM (5 ml) under $N_2$ was added $Et_3N$ (185 μl, 1.31 mmol) and acryloyl chloride (102 μl, 1.31 mmol) at 0° C., the mixture was stirred at 25° C. overnight. The reaction mixture was diluted with DCM and washed with water, dried over $Na_2SO_4$, filtered and concentrated under reduced pressure. The residue was purified by column chromatography (silica gel, gradient cyclohexane/AcOEt, 100/0 to 80/20)) to obtain after trituration in diisopropylether 120 mg of N-(1-(3,5-difluoro-benzyl)-1H-indol-5-yl) acrylamide as a white solid, 35% yield.

Example 53 N-(1-(3,4-difluorobenzyl)-1H-indol-5-yl)acrylamide

To a solution of 1-(3,4-difluorobenzyl)-1H-indol-5-amine (255 mg, 938 mmol) in DCM (5 ml) under $N_2$ was added $Et_3N$ (159 μl, 1.13 mmol) and acryloyl chloride (88 μl, 1.13 mmol) at 0° C., the mixture was stirred at 25° C. overnight. The reaction mixture was diluted with DCM and washed with water, dried over $Na_2SO_4$, filtered and concentrated under reduced pressure. The residue was purified by column chromatography (silica gel, gradient cyclohexane/AcOEt, 100/0 to 80/20) to obtain after trituration in diisopropylether 143 mg of N-(1-(3,4-difluoro-benzyl)-1H-indol-5-yl)acrylamide as a white solid, 49% yield.

Example 54 N-(1-(3-cyanobenzyl)-1H-indol-5-yl) acrylamide

To a solution of 3-((5-amino-1H-indol-1-yl)methyl)benzonitrile (132 mg, 534 μmol) in DCM (6 ml) under $N_2$ was added $Et_3N$ (91 μl, 6.46 μmol) and acryloyl chloride (50 μl, 644 μmol) at 0° C., the mixture was stirred at 25° C. overnight. The reaction mixture was diluted with DCM and washed with water, dried over $Na_2SO_4$, filtered and concentrated under reduced pressure. The residue was purified by reverse phase chromatography (mobile phase [A: $H_2O$(0.2% FA) B: MeCN, gradient B: 20%-80%, 18 min]) to obtain after trituration in diisopropylether 70 mg of N-(1-(3-cyanobenzyl)-1H-indol-5-yl)acrylamide as a white solid, 42% yield.

The following examples represent a variation of scheme 2 with slight changes of the reaction conditions used for of the alkylation step 1 and the reduction of the nitro-group in step 2.

Example 55 N-(14(5-(trifluoromethyl)furan-2-yl) methyl)-1H-indol-5-yl)acrylamide

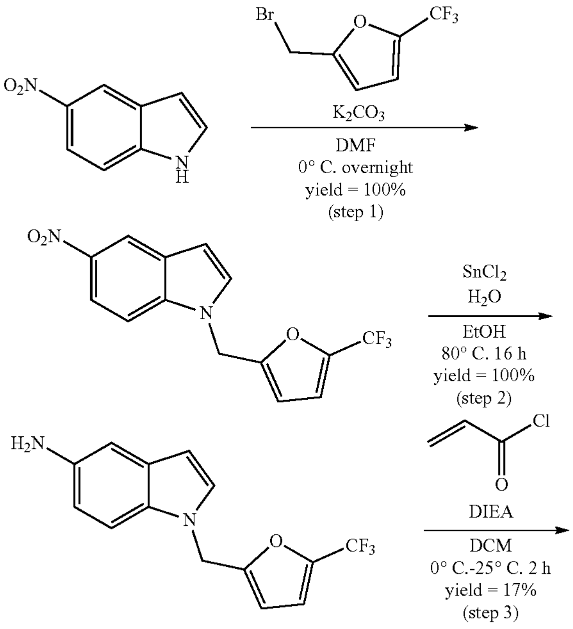

-continued

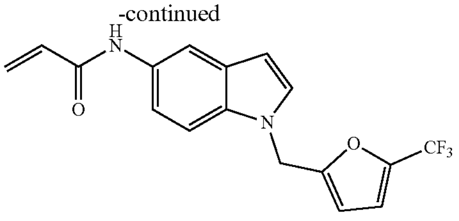

5-nitro-1-((5-(trifluoromethyl)furan-2-yl)methyl)-1H-indole (Step 1)

To a solution of 5-nitro-1H-indole (200 mg, 1.21 mmol) in DMF (15 ml) under $N_2$ was added $K_2CO_3$ (845 mg, 6.05 mmol) at 0° C., the mixture was stirred at 0° C. for 10 min before pouring 2-(bromomethyl)-5-(trifluoromethyl)furan (423 μl, 3.03 mmol). The mixture was stirred at 0° C. overnight. The reaction mixture was concentrated under reduced pressure to obtain a yellow oil, which was purified by column chromatography ($SiO_2$, Cyclohexane/AcOEt 6/4) to obtain 385 mg of 5-nitro-1-((5-(trifluoromethyl)furan-2-yl)methyl)-1H-indole as a yellow solid, 100% yield.

1-((5-(trifluoromethyl)furan-2-yl)methyl)-1H-indol-5-amine (Step 2)

To a solution of 5-nitro-1-((5-(trifluoromethyl)furan-2-yl) methyl)-1H-indole (236 mg, 753 μmol) in EtOH (14 ml) under $N_2$ was added tin(II)chloride hydrate (1.39 g, 6.04 mmol), the mixture was stirred at 80° C. for 16 h. The reaction mixture was diluted with DCM, washed with a saturated aqueous solution of $NaHCO_3$ and brine, filtered on a hydrophobic cartridge and concentrated under reduced pressure to afford 223 mg of crude 1-((5-(trifluoromethyl) furan-2-yl)methyl)-1H-indol-5-amine as a brown oil, which was used without further purification for the next step.

N-(1-((5-(trifluoromethyl)furan-2-yl)methyl)-1H-indol-5-yl)acrylamide (Step 3)

To a solution of 1-((5-(trifluoromethyl)furan-2-yl) methyl)-1H-indol-5-amine (221 mg, 749 μmol) in DCM (14 ml) under $N_2$ was added DIEA (200 μl, 1.14 mmol) and acryloyl chloride (58 μl, 716 μmol) at 0° C., the mixture was stirred at 25° C. overnight. The reaction mixture was diluted with DCM, washed with a saturated aqueous solution of $NaHCO_3$ and brine, dried over $Na_2SO_4$, filtered and concentrated under reduced pressure. The residue was purified by reverse phase chromatography (column CSH 250×50 mm 5 μm (Waters), mobile phase [A: $H_2O$(0.1% FA), B: MeCN (0.1% FA)]; gradient B 31%-51%, 20 min) to obtain after trituration in diisopropylether 42 mg of N-(1-((5-(trifluoromethyl)furan-2-yl)methyl)-1H-indol-5-yl)acrylamide as a white solid, 17% yield.

The following examples 56 and 57 are synthesized as described for example 55.

Example 56 N-(1-(thiazol-4-ylmethyl)-1H-indol-5-yl)acrylamide

To a solution of 1-(thiazol-4-ylmethyl)-1H-indol-5-amine (215 mg, 844 μmol) in DCM (10 ml) under $N_2$ was added DIEA (253 μl, 1.44 mmol) and acryloyl chloride (65 μl, 802 μmol) at 0° C., the mixture was stirred at 25° C. overnight. The reaction mixture was diluted with DCM, washed with a saturated aqueous solution of $NaHCO_3$ and brine, dried over $Na_2SO_4$, filtered and concentrated under reduced pressure. The residue was purified by column chromatography (silica gel, gradient DCM/MeOH, 100/0 to 97/3) to obtain 138 mg of crude product (90% purity LCMS) which was purified by reverse phase chromatography (Gilson GX271 column CSH 250×50 mm 5 μm (Waters), mobile phase [A: $H_2O$(0.1% FA), B: MeCN(0.1% FA)]; gradient B %: 17%-37%; 20 min) to obtain after trituration in diisopropylether 75 mg of N-(1-(thiazol-4-yl-methyl)-1H-indol-5-yl)acrylamide as a white solid 31% yield.

Example 57 N-(1-((2-(trifluoromethyl)thiazol-4-yl) methyl)-1H-indol-5-yl)acrylamide To a solution of N-1-((2-(trifluoromethyl)thiazol-4-yl) methyl)-1H-indol-5-amine (188 mg, 626 μmol) in DCM (10 ml) under $N_2$ was added DIEA (165 μl, 938 μmol) and acryloyl chloride (49 μl, 605 μmol) at 0° C., the mixture was stirred at 25° C. overnight. The reaction mixture was diluted with DCM, washed with a saturated aqueous solution of $NaHCO_3$ and brine, dried over $Na_2SO_4$, filtered and concentrated under reduced pressure. The residue was purified by reverse phase chromatography (column CSH 250*50 mm 5 μm (Waters), mobile phase [A: $H_2O$(0.1% FA), MeCN (0.1% FA)]; gradient B %: 32%-52%; 25 min) to obtain after trituration in diisopropylether 102 mg of N-(1-((2-(trifluoromethyl)thiazol-4-yl)methyl)-1H-indol-5-yl)acrylamide as a white solid, 46% yield.

The following examples 58 to 60 were synthesized as described in scheme 2 by using the appropriate indoles as starting materials.

Example 58 N-(1-(3-(trifluoromethynbenzyl)-1H-indol-7-yl)acrylamide

To a solution of 1-(3-(trifluoromethyl)benzyl)-1H-indol-7-amine (200 mg, 689 μmol) in DCM (2 ml) under $N_2$ was added $Et_3N$ (144 μl, 1.03 mmol) and acryloyl chloride (78 mg, 827 μmol) at 0° C., the mixture was stirred at 25° C. for 1 h30. The reaction mixture was diluted with DCM and washed with water, dried over $MgSO_4$, filtered and concentrated under reduced pressure. The residue was purified by column chromatography (silica gel, gradient heptane/AcOEt 100/0 to 80/20) to obtain after trituration in diethylether 77 mg of N-(1-(3-(trifluoro-methyl)benzyl)-1H-indol-7-yl) acrylamide as a cream solid, 30% yield.

Example 59 N-(1-(3-(methylsulfonynbenzyl)-1H-indol-5-yl)acrylamide

To a solution of 1-(3-(methylsulfonyl)benzyl)-1H-indol-5-amine (187 mg, 610 μmol) in DCM (5 ml) under $N_2$ was added $Et_3N$ (103 μl, 732 μmol) and acryloyl chloride (57 μl, 735 μmol) at 0° C., the mixture was stirred at 25° C. overnight. The reaction mixture was diluted with DCM and washed with a saturated aqueous solution of $NaHCO_3$ and water, dried over $MgSO_4$, filtered and concentrated under reduced pressure. The residue was purified by column chromatography (silica gel, gradient DCM/MeOH, 0/100 to 5/95) to obtain after trituration in diisopropylether 107 mg of N-(1-(3-(methylsulfonyl)benzyl)-1H-indol-5-yl)acrylamide as a light pink solid, 47% yield.

Example 60 N-(3-(methoxymethyl)-1-(3-(trifluoromethyl)benzyl)-1H-indol-5-yl)acryl-amide To a solution of 3-(methoxymethyl)-1-(3-(trifluoromethyl)benzyl)-1H-indol-5-amine (300 mg, 897 μmol) in DCM (4 ml) were added DIEA (313 μl, 1.79 mmol) at 0° C., followed by acryloyl chloride (88 μl, 1.08 mmol) at 0° C. The mixture was allowed to warm to 25° C. and stirred for 2 hours at RT. The mixture was diluted with DCM (20 ml) and washed with water (5 ml×2). The organic phase was dried over $Na_2SO_4$, filtered and concentrated under reduced pressure. The mixture was purified by preparative TLC (PE/AcOEt, 1/1) to obtain a crude product which was purified by reverse phase chromatography (column: Phenomenex Gemini-NX C18 75*30 mm 3 μm; mobile phase: [A: $H_2O$(10 mM $NH_4HCO_3$), B: MeCN]; gradient B %: 34%-64%, 8 min) to obtain 216 mg of N-(3-(methoxymethyl)-1-(3-(trifluoromethyl)-benzyl)-1H-indol-5-yl)acrylamide as an off-white solid, 62% yield.

Example 61 Methyl 5-acrylamido-1-(3-(trifluoromethynbenzyl)-1H-indole-3-carboxylate To a solution of methyl 5-amino-1-(3-(trifluoromethyl) benzyl)-1H-indole-3-carboxylate (1.35 g, 3.88 mmol) in DCM (15 ml) were added DIEA (1.35 ml, 7.75 mmol) and acryloyl chloride (368 mg, 4.07 mmol) at 0° C. The mixture was allowed to warm to 25° C. and stirred for 2 hours. The mixture was diluted with DCM (150 ml) and washed with water (40 ml×3). The organic phase was dried over $Na_2SO_4$, filtered and concentrated under reduced pressure to obtain the crude product, which was triturated with 20 ml of PE/AcOEt (20/1) to afford 1.1 g of methyl 5-acrylamido-1-(3-(trifluoromethyl)benzyl)-1H-indole carboxylate as a yellow solid, 71% yield.

The following examples 62 to 76 were synthesized as already described for example 43 except for examples 62, 64 and 65 where the reaction conditions of step 2 (reduction of the nitro-group) were the same as described in example 42 for step 2.

Example 62 N-(1-(3-(trifluoromethyl)phenyl)-1H-indol-6-yl)acrylamide

To a solution of 1-(3-(trifluoromethyl)phenyl)-1H-indol-6-amine (220 mg, 796 μmol) in DCM (4 ml) was added DIEA (309 mg, 2.39 mmol) and acryloyl chloride (79 mg, 876 μmol) at 0° C. The mixture was allowed to warm to 25° C. and stirred for 1 hour. The reaction mixture was diluted with DCM (10 ml) and washed with $H_2O$ (10 ml). The organic phase was washed with brine (10 ml×2), dried over $Na_2SO_4$, filtered and concentrated under reduced pressure to obtain a residue, which was purified by reverse phase chromatography (column: Phenomenex Gemini-NX C18 75*30 mm 3 μm; mobile phase: [A: water (0.225% FA) B: MeCN]; gradient B %: 45%-75%, 7 min) to obtain 163 mg of N-(1-(3-(trifluoromethyl)phenyl)-1H-indol-6-yl)acrylamide as a purple solid, 62% yield.

Example 63 N-(1-(4-(pentafluoro-$\lambda^6$-sulfanyl)phenyl]indol-5-yl)acrylamide To a solution of 1-(4-(pentafluoro-$\lambda^6$-sulfanyl)phenyl) indol-5-amine (210 mg, 628 μmol) in DCM (3 ml) was added DIEA (219 μl, 1.26 mmol) and acryloyl chloride (62 μl, 754 μmol) at 0° C. The mixture was allowed to warm to 25° C. and stirred for 2 hours. The mixture was diluted with DCM (20 ml) and washed with water (10 ml×3). The organic phase was dried over $Na_2SO_4$, filtered and concentrated under reduced pressure to obtain the mixture, which was triturated with 20 ml solution of PE/AcOEt 10/1 to obtain 160 mg crude product. Final purification was realized by reverse phase chromatography (column: Waters Xbridge 150*25 mm 5 µm; mobile phase [A: $H_2O$(10 mM $NH_4HCO_3$), B: MeCN]; gradient B %: 52%-82%, 10 min) to obtain 103 mg of N-(1-(4-(pentafluoro-$\lambda^6$-sulfanyl)phenyl)indol-5-yl)-acrylamide as an off-white solid, 42% yield.

Example 64 N-(1-(4-(trifluoromethyl)phenyl)-1H-indol-6-yl)acrylamide

To a solution of 1-(4-(trifluoromethyl)phenyl)-1H-indol-6-amine (240 mg, 869 µmol) in DCM (3 ml) was added DIEA (337 mg, 2.61 mmol) and acryloyl chloride (86 mg, 956 µmol) at 0° C. The mixture was allowed to warm to 25° C. and stirred for 2 hours. The reaction mixture was diluted with DCM (10 ml) and washed with $H_2O$ (10 ml). The organic phase was washed with brine (10 ml×2), dried over $Na_2SO_4$, filtered and concentrated under reduced pressure to obtain a residue, which was purified by reverse phase chromatography (column: Phenomenex Gemini-NX C18 75*30 mm 3 µm; mobile phase: [$H_2O$(0.225% FA)-MeCN]; gradient B %: 45%-75%, 7 min) to obtain 150 mg of N-(1-(4-(trifluoromethyl)phenyl)-1H-indol-6-yl)acrylamide as a yellow solid, 52% yield.

Example 65 N-(1-(2-methyl-4-(trifluoromethyl)phenyl)-1H-indol-5-yl)acrylamide

To a solution of 1-(2-methyl-4-(trifluoromethyl)phenyl)-1H-indol-5-amine (90 mg, 310 µmol) and DIEA (108 µl, 620 µmol) in DCM (4 ml) was added a solution of acryloyl chloride (30 µl, 372 µmol) in DCM (0.4 ml) at 0° C. The mixture was allowed to warm to 25° C. and stirred for 1 hours. The mixture was diluted with DCM (15 ml) and washed with water (5 ml×3), dried over $Na_2SO_4$, filtered and concentrated under reduced pressure to obtain a residue which was purified by reverse phase chromatography (column: Waters Xbridge 150*25 mm 5 µm; mobile phase: [A: $H_2O$(10 mM $NH_4HCO_3$) B: MeCN]; gradient B %: 46%-76%, 8 min) to obtain 75 mg of N-(1-(2-methyl-4-(trifluoromethyl)phenyl)-1H-indol-5-yl)acrylamide as a yellow solid, 70% yield.

Example 66 N-(1-(3,5-difluorophenyl)-1H-indol-5-yl)acrylamide

To a solution of 1-(3,5-difluorophenyl)-1H-indol-5-amine (104 mg, 426 µmol) in DCM (4 ml) under $N_2$ was added $Et_3N$ (89 µl, 639 µmol) and acryloyl chloride (48 mg, 511 µmol) at 0° C., the mixture was stirred at 25° C. for 2 h. The reaction mixture was diluted with DCM and washed with water, dried over $MgSO_4$, filtered and concentrated under reduced pressure. The residue was purified by column chromatography (silica gel, gradient heptane/AcOEt, 65/35) to obtain after trituration in diethylether 52 mg of N-(1-(3-(trifluoromethyl)benzyl)-1H-indol-7-yl)acrylamide as white solid, 41% yield.

Example 67 N-(1-(5-fluoropyridin-3-yl)-1H-indol-5-yl)acrylamide

To a solution of 1-(5-fluoropyridin-3-yl)-1H-indol-5-amine (148 mg, 645 µmol) in DCM (4 ml) under $N_2$ was added DIEA (195 µl, 1.11 mmol) and acryloyl chloride (60 µl, 741 µmol) at 0° C., the mixture was stirred at 25° C. overnight. The reaction mixture was diluted with DCM, washed with a saturated aqueous solution of $NaHCO_3$ and brine, dried over $Na_2SO_4$, filtered and concentrated under reduced pressure. The residue was purified by column chromatography (silica gel, gradient DCM/MeOH, 100/0 to 97/3) to obtain after trituration in diisopropylether 109 mg of N-(1-(5-fluoropyridin-3-yl)-1H-indol-5-yl)acrylamide as a white solid, 60% yield.

Example 68 N-(1-(2-(trifluoromethyl)pyridin-4-yl)-1H-indol-5-yl)aylamide

To a solution of 1-(2-(trifluoromethyl)pyridin-4-yl)-1H-indol-5-amine (210 mg, 636 µmol) in DCM (10 ml) under $N_2$ was added DIEA (167 µl, 950 µmol) and acryloyl chloride (55 µl, 679 µmol) at 0° C., the mixture was stirred at 25° C. and allowed to raise to RT overnight. The reaction mixture was diluted with DCM, washed with a saturated aqueous solution of $NaHCO_3$ and brine, dried over $Na_2SO_4$, filtered and concentrated under reduced pressure. The residue was purified by column chromatography (silica gel, gradient DCM/MeOH, 100/0 to 97/3) to obtain after trituration in diisopropylether 144 mg of N-(1-(2-(trifluoromethyl)pyridin-4-yl)-1H-indol-5-yl)acrylamide as a cream-colored solid, 68% yield.

Example 69 N-(3-methyl-1-(4-(trifluoromethyl)phenyl)-1H-indol-5-yl)acrylamide

To a solution of 3-methyl-1-(4-(trifluoromethyl)phenyl)-1H-indol-5-amine (150 mg, 517 µmol) in DCM (2 ml) were added DIEA (200 mg, 1.55 mmol) and acryloyl chloride (46 µl, 568 µmol) at 0° C. The mixture was stirred at 25° C. for 1 hour. The reaction mixture was diluted with DCM (10 ml) and washed with $H_2O$ (10 ml). The organic phase was washed with brine (10 ml×2), dried over $Na_2SO_4$, filtered and concentrated under reduced pressure to obtain a residue. This residue was purified by reverse phase chromatography (column: Waters Xbridge 150*25 mm 5 µm; mobile phase: [A: H2O (10 mM $NH_4HCO_3$), B: MeCN]; gradient B %: 50%-83%, 10 min) to obtain 95 mg of N-(3-methyl-1-(4-(trifluoromethyl)phenyl)-1H-indol-5-yl)acrylamide as a white solid, 54% yield.

Example 70 N-(2-methyl-1-(4-(trifluoromethyl)phenyl)-1H-indol-5-yl)acrylamide

To a mixture of 2-methyl-5-nitro-1-(4-(trifluoromethyl) phenyl)-1H-indole (500 mg, 1.72 mmol) and DIEA (668 mg, 5.17 mmol) in DCM (20 ml) was added acryloyl chloride (171 mg, 1.89 mmol) at 0° C. under $N_2$. The mixture was stirred at 20° C. for 2 hours. The residue was poured into water (15 ml). The aqueous phase was extracted with AcOEt (80 ml). The organic phase was washed with brine (20 ml), dried with $Na_2SO_4$, filtered and concentrated under reduced pressure. The residue was purified by reverse phase chromatography (column: Phenomenex Synergi C18 150*25 mm 10 µm; mobile phase: [A: $H_2O$(0.225% FA) B: MeCN]; gradient B %: 54%-84%, 10 min) to obtain 185 mg of N-(2-methyl-1-(4-(trifluoromethyl)-phenyl)-1H-indol-5-yl) acrylamide as a white solid, 31% yield.

Example 71 N-methyl-N-(2-methyl-1-(4-(trifluoromethyl)phenyl)-1H-indol-5-yl)acryl-amide To a mixture of N-(2-methyl-1-(4-(trifluoromethyl)phenyl)-1H-indol-5-yl)acrylamide (example 70, 350 mg, 1.02 mmol) in DMF (8 ml) was added NaH 60% in mineral oil (81 mg, 2.03 mmol) at 0° C. under $N_2$. The mixture was stirred at 0° C. for 30 min. Iodomethane (95 µl, 1.52 mmol)

was added dropwise and the mixture was allowed to rise to 20° C. and stirred for 1 hour. The residue was poured into water (10 ml). The aqueous phase was extracted with AcOEt (10 ml). The combined organic phase was washed with brine (10 ml), dried with $Na_2SO_4$, filtered and concentrated under reduced pressure. The residue was purified by reverse phase chromatography (column: Phenomenex Gemini-NX C18 75*30 mm 3 μm; mobile phase [A: $H_2O$(0.225% FA) B: MeCN]; gradient B %: 52%-82%, 7 min) to obtain 203 mg of N-methyl-N-(2-methyl-1-(4-(tri-fluoromethyl)phenyl)-1H-indol-5-yl)acryl-amide as a yellow solid, 55% yield.

Example 72 N-[3-(methoxymethyl)-1-[4-(trifluoromethyl)phenyl]indol-5-yl]acryl amide To a solution of 3-(methoxymethyl)-1-(4-(trifluoromethyl)phenyl)-1H-indol-5-amine (430 mg, 1.34 mmol) in DCM (6 ml) were added DIEA (468 μl, 2.68 mmol) and acryloyl chloride (131 μl, 1.61 mmol) at 0° C. Then the mixture was allowed to warm to 25° C. and the mixture was stirred for 2 hours. The mixture was diluted with DCM (15 ml) and washed with water (10 ml×2). The organic phase was dried over $Na_2SO_4$, filtered and concentrated under reduced pressure to obtain the crude product which was purified by reverse phase chromato-graphy (column: Phenomenex Gemini-NX C18 75*30 mm 3 μm; mobile phase: [A: $H_2O$(10 mM $NH_4HCO_3$) B: MeCN]; gradient B %: 38%-68%, 8 min) to obtain 348 mg of N-[3-(methoxymethyl)-1-[4-(trifluoromethyl)phenyl]indol-5-yl]acrylamide as a yellow solid, 69% yield.

Example 73 N-(6-fluoro-1-(4-(trifluoromethyl)phenyl)-1H-indol-5-yl)acrylamide

To a solution of 6-fluoro-1-(4-(trifluoromethyl)phenyl)-1H-indol-5-amine (350 mg, 1.19 mmol) in DCM (5 ml) was added DIEA (414 μl, 2.38 mmol) and acryloyl chloride (116 μl, 1.43 mmol) at 0° C. Then the mixture was allowed to warm to 25° C. and stirred for 2 hours. The mixture was diluted with DCM (100 ml) and washed with water (15 ml×3). The organic phase was dried over $Na_2SO_4$, filtered and concentrated under reduced pressure to obtain crude product which was triturated by AcOEt (15 ml) to obtain 211 mg of N-(6-fluoro-1-(4-(trifluoromethyl)phenyl)-1H-indol-5-yl)acrylamide as a white solid, 50% yield.

The following examples 74 to 76 were synthesized based on the intermediate 1-(4-(trifluoro-methyl)-phenyl)-1H-indol-5-amine already described for example 43.

Example 74 N-methyl-N-(1-(4-(trifluoromethyl)phenyl)-1H-indol-5-yl)acrylamide

To a solution of N-(1-(4-(trifluoromethyl)phenyl)-1H-indol-5-yl)acrylamide (example 44, 200 mg, 605 μmol) in THF (3 ml) was added NaH 60% in mineral oil (36.33 mg, 908 μmol) at 0° C. After stirring for 0.5 hour, methyliodide (75 μl, 1.21 mmol) was added. Then the mixture was allowed to rise to 20° C. and stirred for 1 hour. The mixture was poured into HCl solution (8 ml, 0.5 M) at 0° C. The aqueous phase was extracted with AcOEt (10 ml×2). The combined organic phase were dried over $Na_2SO_4$, filtered and concentrated under reduced pressure to obtain a residue which was purified by reverse phase chromatography (column: Phenomenex Gemini-NX C18 75*30 mm 3 μm; mobile phase: [A: H2O(10 mM $NH_4HCO_3$), B: MeCN]; gradient B %: 40%-70%, 8 min) to obtain 103 mg of N-methyl-N-(1-(4-(trifluoromethyl)phenyl)-1H-indol-5-yl) acrylamide as a white solid, 49% yield.

Example 75 (E)-N-(1-(4-(trifluoromethyl)phenyl)-1H-indol-5-yl)-but-2-enamide

To a solution of 1-(4-(trifluoromethyl)phenyl)-1H-indol-5-amine (300 mg, 1.09 mmol) in DCM (3 ml) was added $Et_3N$ (181 μl, 1.30 mmol) and (E)-but-2-enoyl chloride (125 μl, 1.30 mmol) at 0° C. Then the mixture was warmed to 20° C. and stirred for 2 hours. The mixture was diluted with DCM (20 ml) and washed with water (15 ml). The organic phase was dried over $Na_2SO_4$, filtered and concentrated under reduced pressure to obtain a mixture, which was purified by reverse phase chromatography (column: Waters Xbridge 150*25 mm 5 μm; mobile phase: [A: H2O(10 mM $NH_4HCO_3$), B: MeCN]; gradient B %: 48%-78%, 10 min) and separated from its observed isomer N-(1-(4-(trifluoromethyl)phenyl)-1H-indol-5-yl)but-3-enamide (not described in this patent) by two subsequent SFC-purifications (column 1: DAICEL CHIRALCEL OD-H (250 mm*30 mm 5 μm); mobile phase: [A: $CO_2$, B: EtOH]; gradient B %: 35%-35%, 4.0 min; 40 min., column 2: Cellucoat 50*4.6 mm 3 μm; mobile phase: [A: $CO_2$, B: EtOH(0.05% DEA); gradient B %: 5%-40%, flow rate: 3 ml/min; Detector: PDA; column temp: 35° C.; back pressure: 100 bar) to obtain 124 mg of (E)-N-(1-(4-(trifluoromethyl)phenyl)-1H-indol-5-yl)-but-2-enamide as a white solid, 33% yield.

Example 76 (E)-4-(dimethylamino)-N-(1-(4-(trifluoromethyl)phenyl)-1H-indol-5-yl)but-2-enamide

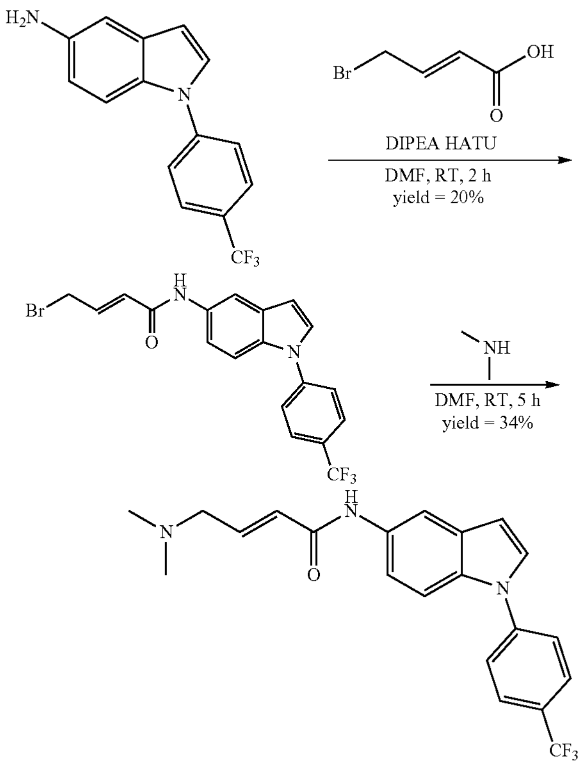

(E)-4-bromo-N-(1-(4-(trifluoromethyl)phenyl)-1H-indol-5-yl)but-2-enamide

To a solution of (E)-4-bromobut-2-enoic acid (896 mg, 5.43 mmol) in DMF (10 ml) was added 1-[4-(trifluoromethyl)phenyl]indol-5-amine (1 g, 3.62 mmol), HATU (2.06 g, 5.4 mmol) and DIEA (1.26 ml, 7.24 mmol) at 0° C. The mixture was stirred at 25° C. for 2 hours. The mixture was diluted with AcOEt (80 ml) and washed with water (30 ml×3). The organic phase was dried over $Na_2SO_4$, filtered and concentrated under reduced pressure to obtain a residue, which was purified by column chromatography ($SiO_2$, PE/AcOEt, 1/0 to 3/1) and reverse phase chromatography (column: Phenomenex Gemini-NX C18 75*30 mm 3 μm; mobile phase: [$H_2O$(0.225% FA)-MeCN]; gradient B %: 50%-80%, 7 min) to obtain 300 mg of (E)-4-bromo-N-(1-(4-(trifluoromethyl)-phenyl)-1H-indol-5-yl)but-2-enamide as a yellow solid, 20% yield.

$^1$H NMR (400 MHz, $CDCl_3$) δ=8.03 (s, 1H, Ar), 7.79 (d, J=8.4 Hz, 2H, Ar), 7.62 (d, J=8.0 Hz, 2H, Ar), 7.53 (d, J=8.8 Hz, 1H, Ar), 7.45-7.36 (m, 2H, CONH, Ar), 7.32 (d, J=8.8 Hz, 1H, Ar), 7.13-7.05 (m, 1H, Ar), 6.71 (d, J=2.4 Hz, 1H, CHCH), 6.22 (d, J=15.2 Hz, 1H, CHCH), 4.10 (d, J=6.8 Hz, 2H, $CH_2$)

(E)-4-(dimethylamino)-N-(1-(4-(trifluoromethyl)phenyl)-1H-indol-5-yl)but-2-enamide To a solution of (E)-4-bromo-N-(1-(4-(trifluoromethyl)phenyl)-1H-indol-5-yl)but-2-enamide (300 mg, 709 μmol) in DMF (3 ml) was added dimethylamine (360 μl, 7.09 mmol). The mixture was stirred at 25° C. for 5 hours. The mixture was purified by reverse phase chromatography (column: Waters Xbridge 150*25 mm 5 μm; mobile phase: [A: $H_2O$ (10 mM $NH_4HCO_3$), B: MeCN]; gradient B %: 39%-69%, 9 min) to obtain 93 mg of (E)-4-(dimethylamino)-N-(1-(4-(trifluoromethyl)phenyl)-1H-indol-5-yl)but-2-enamide as a white solid, 34% yield.

The following example illustrates a new approach for some disubstituted indoles (R11=Cl, F in scheme 1): the amino group was introduced via a Buchwald-coupling reaction using the corresponding appropriately substituted bromoindole, followed by a deprotection step.

Example 77 N-(6-chloro-1-(4-(trifluoromethyl)phenyl)-1H-indol-5-yl)acrylamide

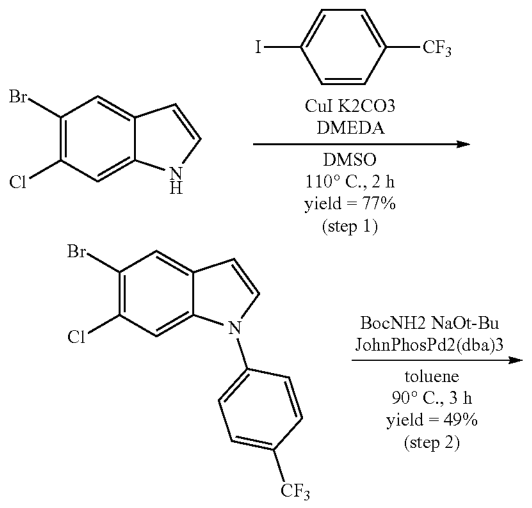

-continued

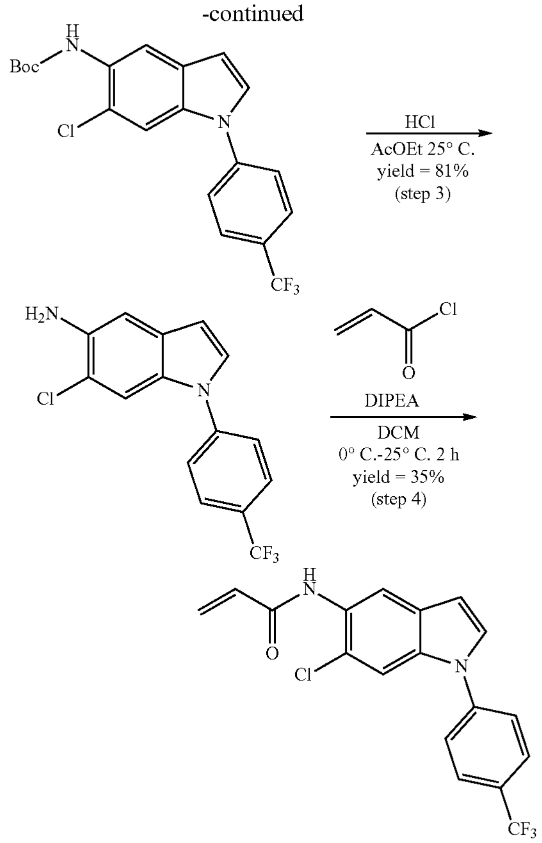

5-bromo-6-chloro-1-(4-(trifluoromethyl)phenyl)-1H-indole (Step 1)

To a solution of 1-iodo-4-(trifluoromethyl)benzene (1.42 g, 5.21 mmol) in DMSO (10 ml) was added 5-bromo-6-chloro-1H-indole (1 g, 4.34 mmol), $K_2CO_3$ (1.20 g, 8.68 mmol), DMEDA (38 mg, 433.86 μmol) and CuI (992 mg, 5.21 mmol) under $N_2$, the mixture was stirred at 110° C. for 2 h. The reaction mixture was diluted with AcOEt (20 ml), washed with water (20 ml×3). The combined organic layers were washed with brine (20 ml×2), dried over $Na_2SO_4$, filtered and concentrated under reduced pressure to obtain a residue, which was purified by column chromatography ($SiO_2$, PE/AcOEt, 1/0) to obtain 1.25 g of 5-bromo-6-chloro-1-(4-(trifluoromethyl)phenyl)-1H-indole as a white solid, 77% yield.

$^1$H NMR (400 MHz, $CDCl_3$) δ=7.93 (s, 1H), 7.82 (d, J=8.4 Hz, 2H), 7.70-7.65 (m, 1H), 7.59 (d, J=8.4 Hz, 2H), 7.35 (d, J=1.8 Hz, 1H), 6.70-6.62 (m, 1H).

tert-butyl(6-chloro-1-(4-(trifluoromethyl)phenyl)-1H-indol-5-yl)carbamate (Step 2)

To a solution of 5-bromo-6-chloro-1-(4-(trifluoromethyl)phenyl)-1H-indole (500 mg, 1.33 mmol), tert-butyl carbamate (188 mg, 1.60 mmol) in toluene (5 ml) was added t-BuONa (257 mg, 2.67 mmol), JohnPhos (40 mg, 133 μmol) and $Pd_2(dba)_3$ (122 mg, 133 μmol) under $N_2$. The mixture was stirred at 90° C. for 3 h. The residue was purified by column chromatography ($SiO_2$, PE/AcOEt, 50/1 to 20/1) to obtain 270 mg of tert-butyl-(6-chloro-1-(4-(trifluoromethyl)phenyl)-1H-indol-5-yl)carbamate as a yellow solid, 49% yield.

$^1$H NMR (400 MHz, DMSO-$d_6$) δ=8.60 (s, 1H), 7.96-7.92 (m, 2H), 7.89-7.83 (m, 2H), 7.81 (d, J=1.8 Hz, 1H), 7.75 (s, 1H), 7.72 (s, 1H), 6.79-6.76 (m, 1H), 1.46 (s, 9H)

6-Chloro-1-(4-(trifluoromethyl)phenyl)-1H-indol-5-amine (Step 3)

A solution of tert-butyl(6-chloro-1-(4-(trifluoromethyl) phenyl)-1H-indol-5-yl)-carbamate (270 mg, 657 μmol) in HCl/AcOEt (4 M, 5.09 ml) was stirred at 25° C. for 1 h. The reaction mixture was concentrated under reduced pressure to obtain 200 mg of 6-chloro-1-(4-(trifluoromethyl)phenyl)-1H-indol-5-amine (HCl salt) as a white solid which was used in the next step without further purification, 81% yield.

N-(6-chloro-1-(4-(trifluoromethyl)phenyl)-1H-indol-5-yl)acrylamide (Step 4)

To a solution of 6-chloro-1-(4-(trifluoromethyl)phenyl)-1H-indol-5-amine HCl salt (200 mg, 576 μmol) in DCM (2 ml) was added DIEA (223 mg, 1.73 mmol), acryloyl chloride (57 mg, 634 μmol) at 0° C. and the mixture was stirred at 25° C. for 2 h. The reaction mixture was diluted with DCM (10 ml) and washed with $H_2O$ (10 ml). The combined organic layers were washed with brine (10 ml×2), dried over $Na_2SO_4$, filtered and concentrated under reduced pressure to obtain a residue which was purified by reverse phase chromatography (column: Waters Xbridge 150*25 mm 5 μm; mobile phase: [A: $H_2O$ (10 mM $NH_4HCO_3$), B: —MeCN]; gradient B %: 46%-76%, 10 min) to obtain 74 mg of N-(6-chloro-1-(4-(trifluoromethyl)phenyl)-1H-indol-5-yl) acrylamide as a white solid, 35% yield.

The following examples 78 to 79 were synthesized using the same approach as described for example 77 (except for the first step) by using the appropriate indoles as starting materials.

Example 78 N-(6-chloro-1-(3-(trifluoromethynbenzyl)-1H-indol-5-yl)acrylamide 5-bromo-6-chloro-1-(3-(trifluoromethyl)benzyl)-1H-indole (Modified Step 1 of Example 77)

To a solution of 5-bromo-6-chloro-1H-indole (1 g, 4.34 mmol) in DMF (10 ml) was added NaH 60% in mineral oil (191 mg, 4.77 mmol) at 0° C. and stirred at 25° C. for 30 min, then 1-(bromomethyl)-3-(trifluoromethyl)benzene (1.04 g, 4.34 mmol) was added at 0° C. and the mixture was stirred at 25° C. for 3 h. The reaction mixture was diluted with AcOEt (20 ml), washed with water (20 ml×3). The combined organic layers were washed with brine (20 ml×2), dried over $Na_2SO_4$, filtered and concentrated under reduced pressure to obtain a residue which was purified by column chromatography ($SiO_2$, PE) to obtain 1.3 g of 5-bromo-6-chloro-1-(3-(trifluoromethyl)benzyl)-1H-indole as a white solid, 77% yield.

$^1$H NMR (400 MHz, $CDCl_3$) δ=7.89 (s, 1H), 7.55 (m, 1H), 7.45-7.38 (m, 2H), 7.35 (s, 1H), 7.19-7.12 (m, 2H), 6.54-6.49 (m, 1H), 5.31 (s, 2H).

tert-butyl(6-chloro-1-(3-(trifluoromethyl)benzyl)-1H-indol-5-yl)carbamate (Step 2 of Example 77)

To a solution of 5-bromo-6-chloro-1-(3-(trifluoromethyl) benzyl)-1H-indole (500 mg, 1.29 mmol) in toluene (5 ml) were added tert-butyl carbamate (181 mg, 1.54 mmol), t-BuONa (247 mg, 2.57 mmol), JohnPhos (39 mg, 129 μmol) and $Pd_2(dba)_3$ (118 mg, 129 μmol) under $N_2$. The mixture was stirred at 90° C. for 3 h and then concentrated under reduced pressure. The residue was purified by column chromatography ($SiO_2$, PE/AcOEt, 50/1 to 30/1) to obtain 300 mg of tert-butyl(6-chloro-1-(3-(trifluoromethyl)benzyl)-1H-indol-5-yl)-carbamate as a yellow solid, 55% yield.

6-chloro-1-(3-(trifluoromethyl)benzyl)-1H-indol-5-amine (Step 3 of Example 77)

A solution of tert-butyl(6-chloro-1-(3-(trifluoromethyl) benzyl)-1H-indol-5-yl)carbamate (300 mg, 706 μmol) in HCl/AcOEt (4 M, 5.09 ml) was stirred at 25° C. for 0.5 h. The reaction mixture was concentrated under reduced pressure to obtain 240 mg of 6-chloro-1-(3-(trifluoromethyl) benzyl)-1H-indol-5-amine, HCl salt as a white solid, 94% yield.

N-(6-chloro-1-(3-(trifluoromethyl)benzyl)-1H-indol-5-yl)acrylamide (Step 4 of Example 77)

To a solution of 6-chloro-1-(3-(trifluoromethyl)benzyl)-1H-indol-5-amine, HCl salt (190 mg, 526 μmol) in DCM (3 ml) was added DIEA (204 mg, 1.58 mmol), acryloyl chloride (43 μl, 526 μmol) at 0° C., the mixture was stirred at 25° C. for 2 h. The reaction mixture was diluted with DCM (10 ml) and washed with $H_2O$ (10 ml). The combined organic layers were washed with brine (10 ml×2), dried over $Na_2SO_4$, filtered and concentrated under reduced pressure to obtain a residue which was purified by reverse phase chromatography (column: Phenomenex Gemini-NX C18 75*30 mm 3 μm; mobile phase: [A: $H_2O$(10 mM $NH_4HCO_3$), B: MeCN]; gradient B %: 38%-68%, 8 min) to obtain 108 mg of N-(6-chloro-1-(3-(trifluoromethyl)-benzyl)-1H-indol-5-yl)acrylamide as a white solid, 54% yield.

Example 79 N-(7-chloro-1-(3-(trifluoromethynbenzyl)-1H-indol-5-yl)acrylamide

To a solution of 7-chloro-1-(3-(trifluoromethyl)benzyl)-1H-indol-5-amine (150 mg, 462 μmol) in DCM (4 ml) was added DIEA (161 μl, 924 μmol) and acryloyl chloride (41 μl, 508 μmol) at 0° C. under $N_2$. The mixture was stirred at 0° C. for 2 hours and then poured into water (10 ml). The aqueous phase was extracted with DCM (10 ml×2). The combined organic phase was washed with brine (5 ml×2), dried with $Na_2SO_4$, filtered and concentrated under reduced pressure. The residue was purified by reverse phase chromatography (column: Phenomenex Gemini-NX C18 75*30 mm 3 μm; mobile phase: [A: $H_2O$(10 mM $NH_4HCO_3$), B: MeCN]; gradient B %: 40%-70%, 8 min) to obtain 154 mg of N-(7-chloro-1-(3-(trifluoro-methyl)benzyl)-1H-indol-5-yl)acrylamide as a white solid, 88% yield.

The following example illustrates a variation for introducing the amino-group in step 2 and step 3 compared to the method used for examples 77 to 79.

Example 80 N-(6-fluoro-1-(3-(trifluoromethyl)benzyl)-1H-indol-5-yl)acrylamide

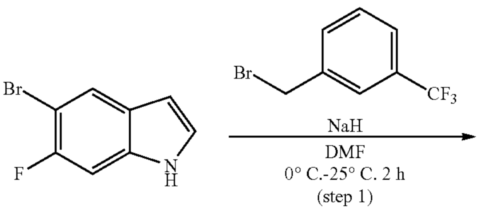

-continued

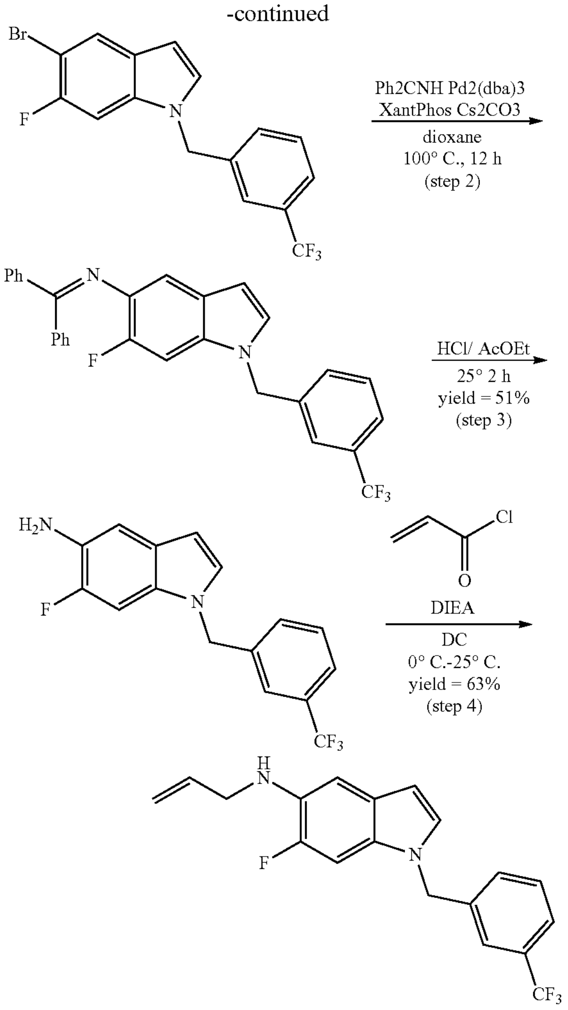

5-Bromo-6-fluoro-1-(3-(trifluoromethyl)benzyl)-1H-indole (Step 1)

To a solution of 5-bromo-6-fluoro-1H-indole (600 mg, 2.80 mmol) in DMF (6 mL) was added NaH 60% in mineral oil (135 mg, 3.36 mmol) at 0° C., followed by the dropwise addition of 1-(bromomethyl)-3-(trifluoromethyl)-benzene (491 μl, 3.22 mmol) at 0° C. during 0.5 hours. The mixture was allowed to warm to 20° C. and stirred for 2 hours. The mixture was poured into ice water (20 ml) and extracted with AcOEt (80 ml×2). The combined organic phase were dried over $Na_2SO_4$, filtered and concentrated under reduced pressure to obtain the residue, which was combined with another batch (starting from 100 mg of 5-bromo-6-fluoro-1H-indole as described) and purified by column chromatography ($SiO_2$, PE/AcOEt, 1/0) to obtain 1 g of 5-bromo-6-fluoro-1-(3-(trifluoromethyl)benzyl)-1H-indole as a white solid.

$^1$H NMR (400 MHz, DMSO-d6) δ=7.88 (d, J=6.8 Hz, 1H), 7.68-7.62 (m, 4H), 7.50 (t, J=8.0 Hz, 1H), 7.44 (d, J=7.6 Hz, 1H), 6.52 (dd, J=0.8, 3.2 Hz, 1H), 5.52 (s, 2H).

N-(diphenylmethylene)-6-fluoro-1-(3-(trifluoromethyl)benzyl)-1H-indol-5-amine (Step 2)

To a solution of 5-bromo-6-fluoro-1-(3-(trifluoromethyl)benzyl)-1H-indole (550 mg, 1.48 mmol) in dioxane (8 ml) was added diphenylmethanimine (322 μl, 1.92 mmol), $Cs_2CO_3$ (1.44 g, 4.43 mmol), XantPhos (171 mg, 295 μmol) and $Pd_2(dba)_3$ (135 mg, 148 μmol). The mixture was stirred at 100° C. under $N_2$ for 12 hours. The mixture was diluted with AcOEt (100 ml) and washed with water (30×3 ml). The organic phase was dried over $Na_2SO_4$, filtered and concentrated under reduced pressure to obtain the residue which was used directly in the next step.

6-Fluoro-1-(3-(trifluoromethyl)benzyl)-1H-indol-5-amine (Step 3)

To a solution of N-(diphenylmethylene)-6-fluoro-1-(3-(trifluoromethyl)benzyl)-1H-indol-5-amine (1.2 g, 2.54 mmol, crude) in THF (27 ml) was added HCl (2 M, 13 ml) dropwise at 0° C. Then the mixture was stirred at 25° C. for 2 hours. The mixture was adjusted to pH 9 with a saturated aqueous solution of $NaHCO_3$ and extracted with AcOEt (100 ml×2). The combined organic phases were dried over $Na_2SO_4$, filtered and concentrated under reduced pressure. The residue was purified by column chromatography ($SiO_2$, PE/AcOEt, 1/0 to 10/3) to obtain 0.4 g of 6-fluoro-1-(3-(trifluoromethyl)benzyl)-1H-indol-5-amine as a black solid, 51% yield.

$^1$H NMR (400 MHz, DMSO-d6) δ=7.60(d, J=7.6 Hz, 1H), 7.57-7.51 (m, 2H), 7.41 (d, J=7.6 Hz, 1H), 7.35 (d, J=3.2 Hz, 1H), 7.20 (d, J=12.0 Hz, 1H), 6.87 (d, J=8.8 Hz, 1H), 6.25 (dd, J=0.4, 3.2 Hz, 1H), 5.39 (s, 2H), 4.54 (s, 2H).

N-(6-fluoro-1-(3-(trifluoromethyl)benzyl)-1H-indol-5-yl)acrylamide (Step 4)

To a solution of 6-fluoro-1-(3-(trifluoromethyl)benzyl)-1H-indol-5-amine (400 mg, 1.30 mmol) in DCM (7 ml) was added $Et_3N$ (361 μl, 2.60 mmol) and acryloyl chloride (127 μl, 1.56 mmol) at 0° C. Then the mixture was allowed to warm to 25° C. and stirred for 2 hours. The mixture was diluted with DCM (20 ml) and washed with water (10 ml×2). The organic phase was dried over $Na_2SO_4$, filtered and concentrated under reduced pressure to obtain the crude product which was purified by reverse phase chromatography (column: Phenomenex luna C18 150*40 mm 15 μm; mobile phase: [A: H2O (0.225% FA) B: MeCN]; gradient B %: 50%-80%, 10 min) to obtain 300 mg of N-(6-fluoro-1-(3-(trifluoromethyl)-benzyl)-1H-indol-5-yl)acrylamide as a white solid, 63% yield.

The following example represents a new combination of already presented reaction conditions: in step 1 slightly modified Ullman-coupling conditions were used, and step 2 and 3 were identic to those illustrated in example 80.

Example 81 N-(7-chloro-1-(4-(trifluoromethyl)phenyl)-1H-indol-5-yl)acrylamide

5-Bromo-7-chloro-1-(4-(trifluoromethyl)phenyl)-1H-indole (Step 1)

To a mixture of 5-bromo-7-chloro-1H-indole (400 mg, 1.74 mmol) and 1-iodo-4-(trifluoromethyl)benzene (566 mg, 2.08 mmol) in dioxane (30 ml) were added $Cs_2CO_3$ (1.70 g, 5.21 mmol), 3,4,7,8-tetramethyl-1,10-phenanthroline (41 mg, 173 μmol) and $[Bu_4NCuI_2]_2$ (194 mg) under $N_2$. The mixture was stirred at 140° C. for 12 hours and concentrated under recuced pressure. The crude product was purified by silica gel chromatography (PE) to obtain 630 mg of 5-bromo-7-chloro-1-(4-(trifluoromethyl)phenyl)-1H-indole as yellow oil, 97% yield.

$^1$H NMR (400 MHz, $CDCl_3$) δ=7.75-7.73 (m, 3H), 7.52-7.50 (m, 2H), 7.34 (d, J=1.6 Hz, 1H), 7.19 (d, J=3.2 Hz, 1H), 6.66 (d, J=3.6 Hz, 1H)

7-Chloro-N-(diphenylmethylene)-1-(4-(trifluoromethyl)phenyl)-1H-indol-5-amine (Step 2)

To a solution of 5-bromo-7-chloro-1-(4-(trifluoromethyl)phenyl)-1H-indole (300 mg, 801 μmol) and diphenylmethanimine (160 mg, 881 μmol) in dioxane (10 ml) were added $Cs_2CO_3$ (783 mg, 2.40 mmol), XantPhos (46 mg, 80 μmol) and $Pd_2(dba)_3$ (73 mg, 80 μmol) in one portion under $N_2$. The mixture was stirred at 100° C. for 6 hours and poured into water (30 ml). The aqueous phase was extracted with AcOEt (40 ml×2). The combined organic phase was washed with brine (10 ml×2), dried with $Na_2SO_4$, filtered and concentrated under reduced pressure to obtain 760 mg crude of 7-chloro-N-(diphenyl-methylene)-1-(4-(trifluoromethyl)phenyl)-1H-indol-5-amine as a brown oil used without further purification in the next step.

7-Chloro-1-(4-(trifluoromethyl)phenyl)-1H-indol-5-amine (Step 3)

To a solution of 7-chloro-N-(diphenylmethylene)-1-(4-(trifluoromethyl)phenyl)-1H-indol-5-amine (760 mg, 1.60 mmol) in THF (15 ml) was added HCl (2 M, 6 ml) at 0° C. under $N_2$. The mixture was stirred at 20° C. for 2 hours. The mixture was quenched by a saturated aqueous solution of $NaHCO_3$ (40 ml). The aqueous phase was extracted with AcOEt (40 ml×2). The combined organic phase was washed with brine (10 ml×2), dried with $Na_2SO_4$, filtered and concentrated under reduced pressure. The residue was purified by silica gel chromatography (PE/AcOEt, gradient 30/1 to 10/1) to afford 290 mg of 7-chloro-1-(4-(trifluoromethyl)-phenyl)-1H-indol-5-amine as a brown solid, 53% yield.

$^1$H NMR (400 MHz, DMSO-d6) δ=7.83 (d, J=8.4 Hz, 2H), 7.60 (d, J=8.0 Hz, 2H), 7.38 (d, J=3.2 Hz, 1H), 6.76 (d, J=1.2 Hz, 1H), 6.63 (d, J=2.0 Hz, 1H), 6.51 (d, J=3.2 Hz, 1H), 4.96 (s, 2H)

N-(7-chloro-1-(4-(trifluoromethyl)phenyl)-1H-indol-5-yl)acrylamide (Step 4)

To a solution of 7-chloro-1-(4-(trifluoromethyl)phenyl)-1H-indol-5-amine (320 mg, 1.03 mmol) in DCM (5 ml) were added DIEA (399 mg, 3.09 mmol), acryloyl chloride (102 mg, 1.13 mmol) at 0° C. and stirred at 25° C. for 2 hours. The reaction mixture was diluted with DCM (10 ml) and $H_2O$ (10 ml) was added. The organic phase was washed with brine (10 ml×2), dried over $Na_2SO_4$, filtered and concentrated under reduced pressure to obtain a residue. The residue was purified by reverse phase chromatography (FA condition; column: Phenomenex Gemini-NX C18 75*30 mm 3 μm; mobile phase: [$H_2O$ (0.225% FA)-MeCN]; gradient B %: 50%-80%, 7 min) to obtain 198 mg of N-(7-chloro-1-(4-(trifluoromethyl)-phenyl)-1H-indol-5-yl)acrylamide as a white solid, 53% yield.

The following example illustrates the reaction sequence to introduce R7=$CH_2OH$ (scheme 1) using a common synthetic intermediate already used for example 72.

Example 82 N-(3-(hydroxymethyl)-1-(4-(trifluoromethyl)phenyl)-1H-indol-5-yl)acrylamide

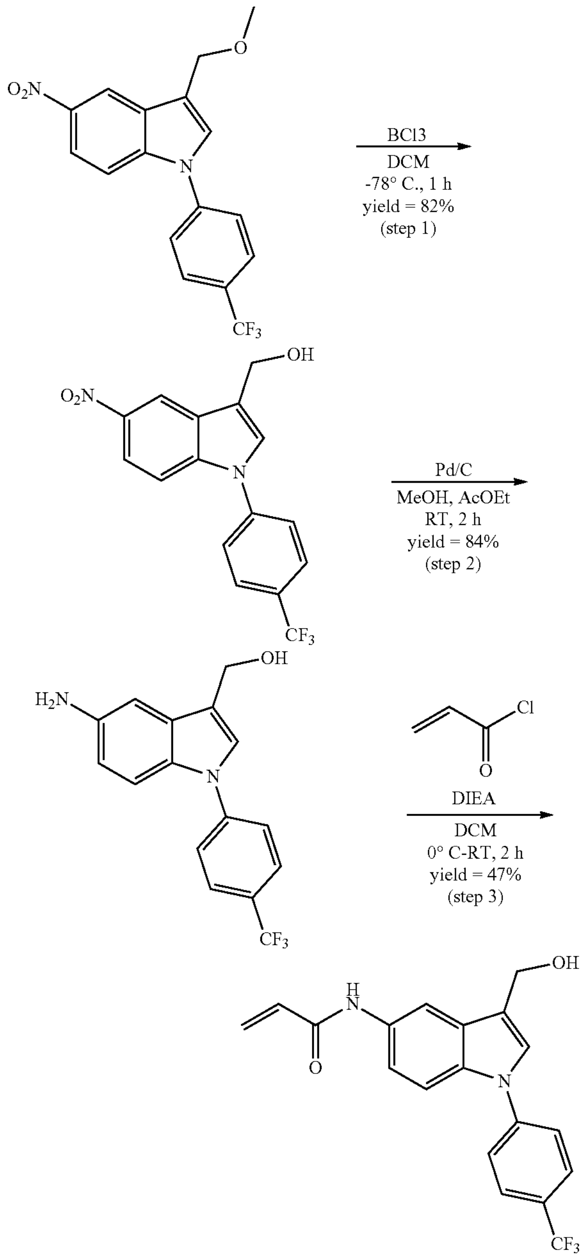

(5-Nitro-1-(4-(trifluoromethyl)phenyl)-1H-indol-3-yl)methanol (Step 1)

To a solution of 3-(methoxymethyl)-5-nitro-1-(4-(trifluoromethyl)phenyl)-1H-indole (600 mg, 1.71 mmol) in DCM (60 ml) was added $BCl_3$ (1 M, 5.14 ml) at −78° C. The mixture was stirred at −78° C. for 1 hour. The mixture was allowed to warm to 0° C. and poured into an ice-cooled saturated aqueous solution of $NaHCO_3$ (60 ml). The organic phase was dried over $Na_2SO_4$, filtered and concentrated under reduced pressure to obtain a residue which was purified by column chromatography ($SiO_2$, PE/AcOEt, 1/0 to 3/1) to obtain 470 mg of (5-nitro-1-(4-(trifluoromethyl)phenyl)-1H-indol-3-yl)methanol) as a yellow solid, 82% yield.

$^1$H NMR (400 MHz, DMSO-d6) δ=8.74 (d, J=2.4 Hz, 1H, Ar), 8.12 (dd, J=2.4, 9.2 Hz, 1H, Ar), 7.98 (d, J=8.4 Hz, 2H, Ar), 7.93 (s, 1H, Ar), 7.88 (d, J=8.4 Hz, 2H, Ar), 7.78 (d, J=9.2 Hz, 1H, Ar), 5.27 (s, 1H, OH), 4.79 (s, 2H, $CH_2$).

(5-Amino-1-(4-(trifluoromethyl)phenyl)-1H-indol-3-yl)methanol (Step 2)

To a solution of (5-nitro-1-(4-(trifluoromethyl)phenyl)-1H-indol-3-yl)methanol (470 mg, 1.40 mmol) in MeOH (10 ml) and AcOEt (2.5 ml) was added Pd/C 10% (50 mg). The mixture was stirred at 25° C. under $H_2$ (15 psi) for 2 hours. The mixture was filtered and concentrated under reduced pressure to obtain a residue, which was purified by column chromatography ($SiO_2$, PE/AcOEt, 1/0 to 1/2) to obtain 360 mg (5-amino-1-(4-(trifluoromethyl)-phenyl)-1H-indol-3-yl) methanol) as a yellow solid, 84% yield.

$^1$H NMR (400 MHz, DMSO-d6) δ=7.87 (d, J=8.4 Hz, 2H, Ar), 7.75 (d, J=8.0 Hz, 2H, Ar), 7.50 (s, 1H, Ar), 7.42 (d, J=8.8 Hz, 1H, Ar), 6.85 (d, J=2.0 Hz, 1H, Ar), 6.62 (dd, J=2.0, 8.8 Hz, 1H, Ar), 4.87 (t, J=5.2 Hz, 1H, OH), 4.79 (s, 2H, $ArNH_2$), 4.60 (d, J=5.2 Hz, 2H, $CH_2$).

N-(3-(hydroxymethyl)-1-(4-(trifluoromethyl)phenyl)-1H-indol-5-yl)acrylamide (Step 3)

To a mixture of (5-amino-1-(4-(trifluoromethyl)phenyl)-1H-indol-3-yl)methanol (360 mg, 1.18 mmol) and DIEA (409 μl, 2.35 mmol) in DCM (10 ml) was added dropwise at 0° C. a solution of acryloyl chloride (96 μl, 1.18 mmol) in DCM (0.5 ml). The mixture was allowed to warm to 25° C. and stirred for 1 hour. The mixture was diluted with DCM (80 ml) and washed with water (50 ml×2). The organic phase was dried over $Na_2SO_4$, filtered and concentrated under reduced pressure to obtain a residue, which was purified by reverse phase chromatography (column: Phenomenex Gemini-NX C18 75*30 mm 3 μm; mobile phase: [A: $H_2O$(10 mM $NH_4HCO_3$), B: MeCN]; gradient B %: 28%-58%, 8 min) to obtain 197 mg of N-(3-(hydroxymethyl)-1-(4-(trifluoromethyl)phenyl)-1H-indol-5-yl)acryl-amide as a yellow solid, 47% yield.

The following examples 83 and 84 illustrate the reaction sequence to introduce R7=CONH2 starting from methyl 5-nitro-1H-indole-3-carboxylate functionalized as already described.

Example 83 5-Acrylamido-1-(3-(trifluoromethyl)benzyl)-1H-indole-3-carboxamide

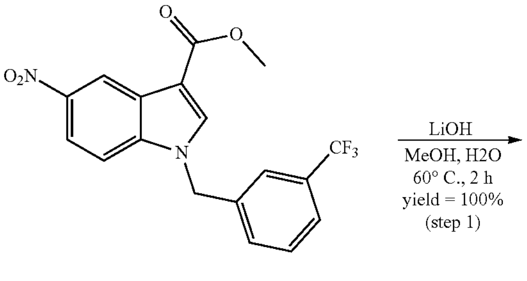

-continued

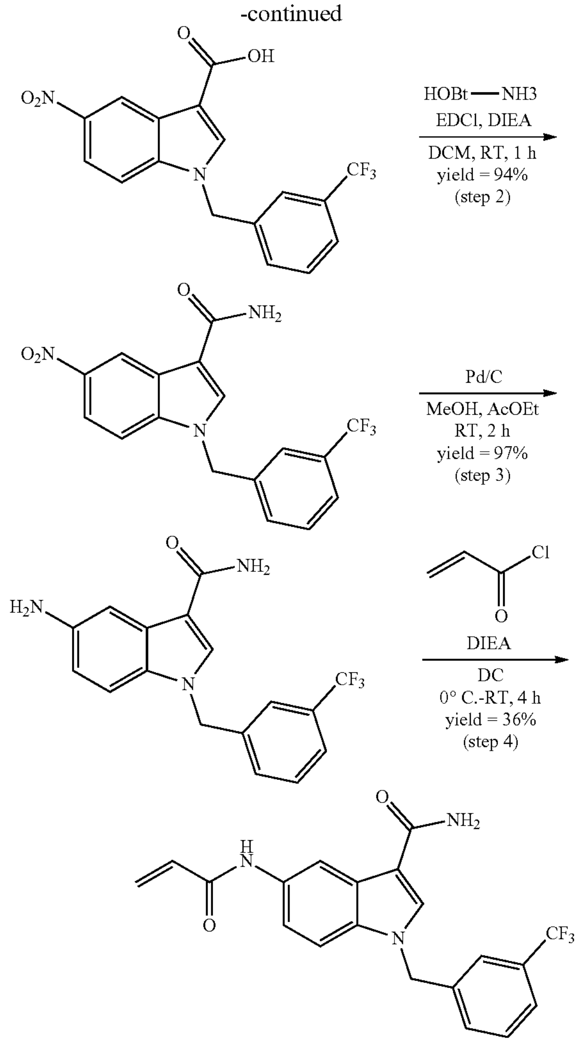

5-Nitro-1-(3-(trifluoromethyl)benzyl)-1H-indole-3-carboxylic acid (Step 1)

To a solution of methyl 5-nitro-1-(3-(trifluoromethyl)benzyl)-1H-indole-3-carboxylate (500 mg, 1.32 mmol) in $H_2O$ (5 ml) and MeOH (5 ml) was added LiOH·$H_2O$ (555 mg, 13.2 mmol). The mixture was stirred at 60° C. for 16 hours. The mixture was diluted with AcOEt (50 ml) and poured into HCl solution (15 ml 1M). The organic phase was dried over $Na_2SO_4$, filtered and concentrated under reduced pressure to obtain 480 mg of 5-nitro-1-(3-(trifluoro-methyl)benzyl)-1H-indole-3-carboxylic acid (100% purity LCMS) as a white solid, 100% yield.

$^1$H NMR (400 MHz, DMSO-d6) δ=8.90 (d, J=2.0 Hz, 1H, Ar), 8.56 (s, 1H, Ar), 8.12 (dd, J=2.4, 9.2 Hz, 1H, Ar), 7.84 (d, J=9.2 Hz, 1H, Ar), 7.79 (s, 1H, Ar), 7.68-7.66 (d, J=7.6 Hz, 1H, Ar), 7.60-7.52 (m, 2H, Ar), 5.71 (s, 2H, $CH_2$)

5-Nitro-1-(3-(trifluoromethyl)benzyl)-1H-indole-3-carboxamide (Step 2)

To a solution of 5-nitro-1-(3-(trifluoromethyl)benzyl)-1H-indole-3-carboxylic acid (480 mg, 1.32 mmol) in DMF (7 ml) were added ammonium 1-oxidobenzotriazole (221 mg, 1.45 mmol), EDCI (278 mg, 1.45 mmol) and DIEA (459

μl, 2.64 mmol). The mixture was stirred at 25° C. for 5 hours. The mixture was diluted with AcOEt (30 ml) and washed water (10 ml×3). The aqueous phase was extracted with AcOEt (10 ml×1). The combined organic phases were dried over $Na_2SO_4$, filtered and concentrated under reduced pressure to obtain a residue which was triturated with DCM (6 ml) to obtain 450 mg of 5-nitro-1-(3-(trifluoromethyl) benzyl)-1H-indole-3-carboxamide as a white solid, 94% yield.

HNMR (400 MHz, DMSO-d6) δ=9.09 (d, J=2.4 Hz, 1H, Ar), 8.37 (s, 1H, Ar), 8.10 (dd, J=2.4, 9.2 Hz, 1H, Ar), 7.83 (d, J=9.2 Hz, 1H, Ar), 7.73-7.68 (m, 3H, Ar, $NH_2$), 7.59 (t, J=7.6 Hz, 1H, Ar), 7.47 (d, J=7.6 Hz, 1H, Ar), 7.15 (s, 1H, Ar), 5.69 (s, 2H, $CH_2$).

5-Amino-1-(3-(trifluoromethyl)benzyl)-1H-indole-3-carboxamide (Step 3)

To a solution of 5-nitro-1-(3-(trifluoromethyl)benzyl)-1H-indole-3-carboxamide (450 mg, 1.24 mmol) in MeOH (12 ml) and AcOEt (3 ml) was added Pd/C 10% (45 mg) under $N_2$. The mixture was stirred at 25° C. for 2 hours under $H_2$ atmosphere (15 psi). The mixture was filtered and concentrated under reduced pressure to obtain 400 mg of 5-amino-1-(3-(trifluoro-methyl)benzyl)-1H-indole-3-carboxamide as a white solid, 97% yield.

$^1$HNMR (400 MHz, DMSO-d6) δ=7.94 (s, 1H, Ar), 7.65-7.54 (m, 3H, Ar), 7.43 (d, J=7.6 Hz, 1H, Ar), 7.36 (d, J=2.0 Hz, 1H, Ar), 7.16 (d, J=8.8 Hz, 1H, Ar), 6.52 (dd, J=2.0, 8.8 Hz, 1H, Ar), 5.43 (s, 2H, $CH_2$), 4.69 (s, 2H, $ArNH_2$).

5-Acrylamido-1-(3-(trifluoromethyl)benzyl)-1H-indole-3-carboxamide (Step 4)

To a solution of 5-amino-1-(3-(trifluoromethyl)benzyl)-1H-indole-3-carboxamide (400 mg, 1.20 mmol) and DIEA (627 μl, 3.60 mmol) in DCM (5 ml) was added a solution of acryloyl chloride (108 μl, 1.32 mmol) in DCM (0.3 ml) at 0° C. The mixture was allowed to warm to 25° C. and stirred for 4 hours. The mixture was diluted with DCM (30 ml) and washed with water (10 ml×3). The organic phase was dried over $Na_2SO_4$, filtered and concentrated under reduced pressure to obtain a residue which was purified by reverse phase chromatography (column: Waters Xbridge 150*25 mm 5 μm; mobile phase: [A: $H_2O$(10 mM $NH_4HCO_3$), B: MeCN]; gradient B %: 30%-60%, 8 min) to obtain 170 mg of 5-acrylamido-1-(3-(trifluoro-methyl)benzyl)-1H-indole-3-carboxamide as a white solid, 36% yield.

The following example was synthesized using the same reaction sequence as described for example 83.

Example 84 5-Acrylamido-1-(4-(trifluoromethyl)phenyl)-1H-indole-3-carboxamide To a solution of 5-amino-1-(4-(trifluoromethyl)phenyl)-1H-indole-3-carboxamide (430 mg, 1.35 mmol) in DCM (2 ml) were added DIEA (522 mg, 4.04 mmol), acryloyl chloride (134 mg, 1.48 mmol) at 0° C. The mixture was stirred at 25° C. for 2 hours. The reaction mixture was diluted with DCM (10 ml) and washed with $H_2O$ (10 ml). The organic phase was washed with brine (10 ml×2), dried over $Na_2SO_4$, filtered and concentrated under reduced pressure to obtain a residue, which was purified by reverse phase chromatography (column: Phenomenex Gemini-NX C18 75*30 mm 3 μm; mobile phase: [A: $H_2O$(0.225% FA) B: MeCN]; gradient B %: 30%-60%, 7 min) to obtain 173 mg of 5-acrylamido-1-(4-(trifluoromethyl)-phenyl)-1H-indole-3-carboxamide as an off-white solid, 34% yield.

The table herein below illustrates the chemical structures and physical properties of a number of compounds of formula (I).

In the table:

- the proton magnetic resonance spectra ($^1$H NMR), as described below, are recorded at 400 MHz, 500 MHz or 600 MHz in DMSO-$d_6$, using the DMSO-$d_6$ peak as reference. The chemical shifts δ are expressed in parts per million (ppm). The signals observed are expressed as follows: s=singlet; d=doublet; t=triplet; m=multiplet or br s=broad singlet; br m=broad multiplet
- the LCMS characteristics, as described below, successively indicated the high-performance liquid chromatography analytical method used and detailed below (A and B), the $[M+H]^+$ peak identified by mass spectrometry and the retention time (Tr) of the compound, expressed in minutes
- the observed ion type was always $[M+H]^+$, except otherwise indicated for examples 60, 72 and 82

Method A

Column: Acquity UPLC/SQD CORTECS C18+ 2.1×50 mm 1.6 μm (Waters), mobile phase [A: $H_2O$ (+0.1% FA), B: MeCN (+0.1% FA)], gradient B from 2 to 100% in 3 min, 1 ml/min Method A'

Column: Acquity UPLC/SQD CORTECS C18+ 2.1×50 mm 1.6 μm (Waters), mobile phase [A: $H_2O$ (+0.1% FA), B: MeCN (+0.1%. FA)], gradient B from 2 to 100% in 10 min, 1 ml/min Method B Column: Acquity UPLC/SDS BEH C18 2.1×50 mm 1.7 μm (Waters), mobile phase [A: $H_2O$ (+0.05% FA), B: MeCN (+0.035% FA), gradient B from 5% to 95% in 3 min, 0.9 ml/min Method C Column: Kinetex EVO C18 2.1×30 mm, 5 μm, mobile phase [A: $H_2O$ (+0.0375% TFA), B: MeCN(+0.01875% TFA)] gradient B from 5% to 95% in 0.8 min, 95% 0.4 min, 1.5 ml/min, column Temp: 50° C., detector: PDA (220 & 254 nm), ionization source: ESI Method D Column: Kinetex EVO C18 2.1×30 mm, 5 μm, mobile phase [A: $H_2O$(+0.025% $NH_3$), B: MeCN], gradient B: from 5% to 95% in 0.8 min, 95% 0.4 min, 1.5 ml/min, column temp: 40° C., detector: PDA (220 & 254 nm), ionization source: ESI

| ex No | IUPAC name | NMR Description | $[M + H]^+$ | Tr (min) | Analytical method |
|---|---|---|---|---|---|
| 1 | N-[1-[[3-(trifluoro-methyl)phenyl] methyl]-indol-5-yl]acryl-amide | 1H NMR (400 MHz, DMSO-d6) δ ppm 5.51 (s, 2 H) 5.70 (dd, J = 10.04, 2.13 Hz, 1 H) 6.22 (dd, J = 16.94, 2.13 Hz, 1 H) 6.38-6.54 (m, 2 H) 7.28 (dd, J = 8.78, 2.01 Hz, 1 H) 7.37-7.46 (m, 2 H) 7.49-7.58 (m, 3 H) 7.59-7.64 (m, 1 H) 8.00 (d, J = 1.76 Hz, 1 H) 9.96 (s, 1 H) | 345 | 1.23 | A |

-continued

| ex No | IUPAC name | NMR Description | $[M + H]^+$ | Tr (min) | Analytical method |
|---|---|---|---|---|---|
| 2 | N-methyl-N-(1-(3-(trifluoro-methyl)benzyl)-1H-indol-5-yl)acrylamide | 1H NMR (400 MHz, DMSO-d6) δ ppm 3.24 (s, 3 H) 5.46 (dd, J = 10.16, 2.38 Hz, 1 H) 5.56 (s, 2 H) 5.97 (dd, J = 17.06, 10.16 Hz, 1 H) 6.10 (dd, J = 17.06, 2.38 Hz, 1 H) 6.54 (d, J = 3.01 Hz, 1 H) 7.00 (dd, J = 8.53, 2.01 Hz, 1 H) 7.45 (d, J = 2.01 Hz, 1 H) 7.49 (d, J = 7.62 Hz, 1 H) 7.54-7.60 (m, 2 H) 7.62-7.71 (m, 3 H) | 359 | 1.43 | A |
| 3 | N-(1-(5,5,5-trifluoropentyl)-1H-indol-5-yl)acrylamide | 1H NMR (400 MHz, DMSO-d6) δ ppm 1.37-1.48 (m, 2 H) 1.81 (quin, J = 7.34 Hz, 2 H) 2.18-2.35 (m, 2 H) 4.18 (t, J = 6.90 Hz, 2 H) 5.70 (dd, J = 10.12, 2.01 Hz, 1 H) 6.22 (dd, J = 17.07, 2.01 Hz, 1 H) 6.39 (d, J = 2.76 Hz, 1 H) 6.45 (dd, J = 17.07, 10.12 Hz, 1 H) 7.31 (dd, J = 8.78, 2.01 Hz, 1 H) 7.35 (d, J = 2.76 Hz, 1 H) 7.44 (d, J = 8.78 Hz, 1 H) 7.97 (d, J = 2.01 Hz, 1 H) 9.98 (s, 1 H) | 311 | 1.25 | A |
| 4 | N-(1-(1-(3-(trifluoro-methyl)phenyl) ethyl)-1H-indol-5-yl)-acrylamide | 1H NMR (400 MHz, DMSO-d6) δ ppm 1.90 (d, J = 7.03 Hz, 3 H) 5.69 (dd, J = 10.04, 2.01 Hz, 1 H) 5.92 (q, J = 7.03 Hz, 1 H) 6.21 (dd, J = 16.94, 2.01 Hz, 1 H) 6.43 (dd, J = 16.94, 10.04 Hz, 1 H) 6.52 (d, J = 3.26 Hz, 1 H) 7.24 (dd, J = 8.91, 1.88 Hz, 1 H) 7.36 (d, J = 8.91 Hz, 1 H) 7.46-7.65 (m, 4 H) 7.71 (d, J = 3.26 Hz, 1 H) 7.99 (d, J = 1.88 Hz, 1 H) 9.94 (s, 1 H) | 359 | 1.38 | A |
| 5 | N-(1-(3-(penta-fluoro-λ6-sulfanyl)-benzyl)-1H-indol-5-yl)-acrylamide | 1H NMR (400 MHz, DMSO-d6) δ ppm 5.53 (s, 2 H) 5.69 (dd, J = 10.26, 2.28 Hz, 1 H) 6.22 (dd, J = 17.07, 2.28 Hz, 1 H) 6.38-6.56 (m, 2 H) 7.28 (dd, J = 8.78, 1.76 Hz, 1 H) 7.37 (d, J = 7.53 Hz, 1 H) 7.42 (d, J = 8.78 Hz, 1 H) 7.51-7.62 (m, 2 H) 7.74-7.81 (m, 2 H) 8.00 (d, J = 1.76 Hz, 1 H) 9.96 (s, 1 H) | 403 | 1.37 | A |
| 6 | N-(1-(4-(pentafluoro-λ6-sulfanyl)-benzyl)-1H-indol-5-yl)-acrylamide | 1H NMR (400 MHz, DMSO-d6) δ ppm 5.52 (s, 2 H) 5.70 (dd, J = 10.16, 2.13 Hz, 1 H) 6.22 (dd, J = 17.07, 2.13 Hz, 1 H) 6.38-6.55 (m, 2 H) 7.23-7.39 (m, 4 H) 7.50 (d, J = 3.01 Hz, 1 H) 7.84 (d, J = 8.87 Hz, 2 H) 8.01 (d, J = 1.76 Hz, 1 H) 9.96 (s, 1 H) | 403 | 1.36 | A |
| 7 | N-(1-(4-(trifluoro-methoxy)-benzyl)-1H-indol-5-yl)-acrylamide | 1H NMR (400 MHz, DMSO-d6) δ ppm 5.44 (s, 2 H) 5.70 (dd, J = 10.16, 2.13 Hz, 1 H) 6.22 (dd, J = 17.07, 2.13 Hz, 1 H) 6.39-6.51 (m, 2 H) 7.25-7.33 (m, 5 H) 7.38 (d, J = 8.78 Hz, 1 H) 7.49 (d, J = 3.26 Hz, 1 H) 8.00 (d, J = 1.76 Hz, 1 H) 9.95 (s, 1 H) | 361 | 1.32 | A |
| 8 | N-(1-(3-(trifluoro-methoxy)-benzyl)-1H-indol-5-yl)-acrylamide | 1H NMR (400 MHz, DMSO-d6) δ ppm 5.46 (s, 2 H) 5.70 (dd, J = 10.28, 2.23 Hz, 1 H) 6.22 (dd, J = 16.94, 2.23 Hz, 1 H) 6.40-6.51 (m, 2 H) 7.14-7.19 (m, 2 H) 7.21-7.31 (m, 2 H) 7.36-7.47 (m, 2 H) 7.51 (d, J = 3.26 Hz, 1 H) 8.00 (d, J = 1.76 Hz, 1 H) 9.95 (s, 1 H) | 361 | 1.30 | A |
| 9 | N-(1-(3-iodo-benzyl)-1H-indol-5-yl)-acrylamide | 1H NMR (400 MHz, DMSO-d6) δ ppm 5.37 (s, 2 H) 5.70 (dd, J = 10.16, 2.13 Hz, 1 H) 6.22 (dd, J = 16.94, 2.13 Hz, 1 H) 6.40-6.52 (m, 2 H) 7.10 (t, J = 7.71 Hz, 1 H) 7.17 (d, J = 8.03, 1 H) 7.28 (dd, J = 8.78, 2.01 Hz, 1 H) 7.38 (d, J = 8.78 Hz, 1 H) 7.48 (d, J = 3.01 Hz, 1 H) 7.54-7.67 (m, 2 H) 8.00 (d, J = 2.01 Hz, 1 H) 9.95 (s, 1 H) | 403 | 1.36 | A |
| 10 | N-(1-(2-fluoro-5-(trifluoro-methyl)-benzyl)-1H-indol-5-yl)-acrylamide | 1H NMR (400 MHz, DMSO-d6) δ ppm 5.54 (s, 2 H) 5.70 (dd, J = 10.16, 2.13 Hz, 1 H) 6.23 (dd, J = 16.94, 2.13 Hz, 1 H) 6.40-6.52 (m, 2 H) 7.31 (dd, J = 8.78, 2.01 Hz, 1 H) 7.38-7.54 (m, 4 H) 7.70-7.80 (m, 1 H) 8.00 (d, J = 2.01 Hz, 1 H) 9.97 (s, 1 H) | 363 | 4.23 | A |
| 11 | N-(3-methyl-1-(3-(trifluoro-methyl)-benzyl)-1H-indol-5-yl)-acrylamide | 1H NMR (500 MHz, DMSO-d6) δ ppm 2.23 (d, J = 0.73 Hz, 3 H) 5.43 (s, 2 H) 5.70 (dd, J = 10.03, 1.96 Hz, 1 H) 6.22 (dd, J = 16.99, 1.96 Hz, 1 H) 6.44 (dd, J = 16.99, 10.03 Hz, 1 H) 7.25-7.32 (m, 2 H) 7.34-7.43 (m, 2 H) 7.53 (t, J = 7.70 Hz, 1 H) 7.58-7.63 (m, 2 H) 7.94 (d, J = 1.71 Hz, 1 H) 9.97 (s, 1 H) | 359 | 1.39 | A |

-continued

| ex No | IUPAC name | NMR Description | $[M + H]^+$ | Tr (min) | Analytical method |
|---|---|---|---|---|---|
| 12 | N-(1-(3-methoxy-benzyl)-1H-indol-5-yl)-acrylamide | 1H NMR (400 MHz, DMSO-d6) δ ppm 3.69 (s, 3 H) 5.35 (s, 2 H) 5.69 (dd, J = 10.28, 2.13 Hz, 1 H) 6.22 (dd, J = 16.94, 2.13 Hz, 1 H) 6.40-6.50 (m, 2 H) 6.69-6.85 (m, 3 H) 7.20 (t, J = 7.91 Hz, 1 H) 7.27 (dd, J = 8.78, 2.01 Hz, 1 H) 7.37 (d, J = 8.78 Hz, 1 H) 7.47 (d, J = 3.01 Hz, 1 H) 7.99 (d, J = 2.01 Hz, 1 H) 9.94 (s, 1 H) | 307 | 1.24 | A |
| 13 | N-(2-methyl-1-(3-(trifluoro-methyl)-benzyl)-1H-indol-5-yl)-acrylamide | 1H NMR (400 MHz, DMSO-d6) δ ppm 2.33 (s, 3 H) 5.50 (s, 2 H) 5.69 (dd, J = 10.16, 2.13 Hz, 1 H) 6.22 (dd, J = 16.94, 2.13 Hz, 1 H) 6.29 (s, 1 H) 6.44 (dd, J = 16.94, 10.16 Hz, 1 H) 7.14 (d, J = 7.53 Hz, 1 H) 7.21 (dd, J = 8.78, 1.76 Hz, 1 H) 7.30 (d, J = 8.72 Hz, 1 H) 7.38 (s, 1 H) 7.52 (t, J = 8.72 Hz, 1 H) 7.60 (d, J = 8.72 Hz, 1 H) 7.91 (d, J = 1.76 Hz, 1 H) 9.92 (s, 1 H) | 359 | 1.41 | A |
| 14 | N-(3-cyano-1-(3-(trifluoro-methyl)benzyl)-1H-indol-5-yl)-acrylamide | 1H NMR (400 MHz, DMSO-d6) δ ppm 5.60 (s, 2 H) 5.76 (dd, J = 10.16, 2.010, 1 H) 6.26 (dd, J = 17.07, 2.01 Hz, 1 H) 6.44 (dd, J = 17.07, 10.16 Hz, 1 H) 7.38-7.82 (m, 6 H) 8.20 (d, J = 1.51 Hz, 1 H) 8.47 (s, 1 H) 10.20 (s, 1 H) | 370 | 1.32 | A |
| 15 | N-(1-(3-cyclopropyl-benzyl)-1H-indol-5-yl)-acrylamide | 1H NMR (400 MHz, DMSO-d6) δ ppm 0.55-0.63 (m, 2 H) 0.86-0.95 (m, 2 H) 1.79-1.88 (m, 1 H) 5.32 (s, 2 H) 5.69 (dd, J = 10.04, 2.13 Hz, 1 H) 6.22 (dd, J = 16.94, 2.13 Hz, 1 H) 6.40-6.50 (m, 2 H) 6.86-6.94 (m, 2 H) 6.96 (s, 1 H) 7.15 (t, J = 7.69 Hz, 1 H) 7.27 (dd, J = 8.78, 1.76 Hz, 1 H) 7.38 (d, J = 8.78 Hz, 1 H) 7.46 (d, J = 3.01 Hz, 1 H) 7.98 (d, J = 1.76 Hz, 1 H) 9.94 (s, 1 H) | 317 | 1.43 | A |
| 16 | N-(2,3-dimethyl-1-(3-(trifluoro-methyl)-benzyl)-1H-indol-5-yl)-acrylamide | 1H NMR (400 MHz, DMSO-d6) δ ppm 2.19 (s, 3 H) 2.26 (s, 3 H) 5.47 (s, 2 H) 5.69 (dd, J = 10.16, 2.13 Hz, 1 H) 6.22 (dd, J = 16.94, 2.13 Hz, 1 H) 6.45 (dd, J = 16.94, 10.16 Hz, 1 H) 7.11 (d, J = 7.78 Hz, 1 H) 7.23 (dd, J = 8.76, 1.72 Hz, 1 H) 7.21 (d, J = 8.76 Hz, 1 H) 7.42 (s, 1 H) 7.50 (t, J = 7.78 Hz, 1 H) 7.59 (t, J = 7.78 Hz, 1 H) 7.88 (d, J = 1.72 Hz, 1 H) 9.94 (s, 1 H) | 373 | 1.57 | A |
| 17 | N-(1-(3-methyl-benzyl)-1H-indol-5-yl)-acrylamide | 1H NMR (500 MHz, DMSO-d6) δ ppm 2.24 (s, 3 H) 5.34 (s, 2 H) 5.69 (dd, J = 10.15, 2.08 Hz, 1 H) 6.22 (dd, J = 16.87, 2.08 Hz, 1 H) 6.40-6.50 (m, 2 H) 6.96 (d, J = 7.58 Hz, 1 H) 7.01-7.07 (m, 2 H) 7.18 (t, J = 7.58 Hz, 1 H) 7.26 (dd, J = 8.80, 1.96 Hz, 1 H) 7.37 (d, J = 8.80 Hz, 1 H) 7.45 (d, J = 2.93 Hz, 1 H) 7.98 (d, J = 1.96 Hz, 1 H) 9.94 (s, 1 H) | 291 | 1.48 | A |
| 18 | N-(1-Benzyl-1H-indol-5-yl)-acrylamide | 1H NMR (600 MHz, DMSO-d6) δ ppm 5.35 (s, 2 H) 5.70 (dd, J = 10.04, 2.13 Hz, 1 H) 6.22 (dd, J = 16.94, 2.13 Hz, 1 H) 6.38-6.54 (m, 2 H) 7.15-7.20 (m, 1 H) 7.21-7.31 (m, 5 H) 7.32-7.40 (m, 1 H) 7.45-7.55 (m, 1 H) 8.00 (s, 1 H) 10.00 (s, 1 H ) | 276 | 1.66 | B |
| 19 | N-(1-(3-(trifluoro-methyl)benzyl)-1H-indol-4-yl)-acrylamide | 1H NMR (400 MHz, DMSO-d6) δ ppm 5.53 (s, 2 H) 5.75 (dd, J = 10.04, 2.01 Hz, 1 H) 6.28 (dd, J = 16.81, 2.01 Hz, 1 H) 6.71 (dd, J = 16.81, 10.04 Hz, 1 H) 6.82 (d, J = 3.01 Hz, 1 H) 7.07 (t, J = 8.10 Hz, 1 H) 7.24 (d, J = 8.28 Hz, 1 H) 7.42 (d, J = 7.78 Hz, 1 H) 7.49-7.68 (m, 4 H) 7.75 (br d, J = 7.53 Hz, 1 H) 9.78 (s, 1 H) | 345 | 1.35 | A |
| 20 | (E)-4-(dimethyl-amino)-N-(1-(3-(trifluoro-methyl)benzyl)-1H-indol-4-yl)-but-2-enamide | 1H NMR (400 MHz, DMSO-d6) δ ppm 2.61 (br s, 6 H) 3.58-3.75 (m, 2 H) 5.54 (s, 2 H) 6.63-6.91 (m, 3 H) 7.07 (t, J = 7.91 Hz, 1 H) 7.25 (d, J = 8.28 Hz, 1 H) 7.43 (br d, J = 7.78 Hz, 1 H) 7.50-7.66 (m, 4 H) 7.75 (br d, J = 7.53 Hz, 1 H) 9.91 (s, 1 H) | 402 | 0.84 | A |
| 21 | N-(1-(3-(trifluoro-methyl)benzyl)-1H-indol-6-yl)-acrylamide | 1H NMR (400 MHz, DMSO-d6) δ ppm 5.49 (s, 2 H) 5.70 (dd, J = 10.04, 2.01 Hz, 1 H) 6.21 (dd, J = 16.94, 2.01 Hz, 1 H) 6.38-6.52 (m, 2 H) 7.18 (dd, J = 8.53, 1.76 Hz, 1 H) 7.36 (d, J = 7.53 Hz, 1 H) 7.46-7.68 (m, 5 H) 7.96 (s, 1 H) 10.05 (s, 1 H) | 345 | 1.39 | A |

-continued

| ex No | IUPAC name | NMR Description | [M + H]+ | Tr (min) | Analytical method |
|---|---|---|---|---|---|
| 22 | N-(1-((4,4-difluorocyclo-hexyl)methyl)-1H-indol-5-yl)-acrylamide | 1H NMR (400 MHz, DMSO-d6) δ ppm 1.20-1.35 (m, 2 H) 1.51-1.83 (m, 4 H) 1.89-2.08 (m, 3 H) 4.07 (d, J = 7.28 Hz, 2 H) 5.70 (dd, J = 10.16, 2.13 Hz, 1 H) 6.23 (dd, J = 16.94, 2.13 Hz, 1 H) 6.39 (d, J = 3.01 Hz, 1 H) 6.45 (dd, J = 16.94, 10.16 Hz, 1 H) 7.25-7.36 (m, 2 H) 7.45 (d, J = 8.78 Hz, 1 H) 7.95 (d, J = 3.01 Hz, 1 H) 9.94 (s, 1 H) | 319 | 1.25 | A |
| 23 | N-(1-((tetrahydro-2H-pyran-4-yl)methyl)-1H-indol-5-yl)-acrylamide | 1H NMR (400 MHz, DMSO-d6) δ ppm 1.19-1.43 (m, 4 H) 1.94-2.11 (m, 1 H) 3.20 (td, J = 11.54, 2.26 Hz, 2 H) 3.81 (br dd, J = 11.29, 2.51 Hz, 2 H) 4.04 (d, J = 7.28 Hz, 2 H) 5.70 (dd, J = 10.04, 2.01 Hz, 1 H) 6.22 (dd, J = 16.94, 2.01 Hz, 1 H) 6.38 (d, J = 3.01 Hz, 1 H) 6.45 (dd, J = 16.94, 10.04 Hz, 1 H) 7.22-7.36 (m, 2 H) 7.45 (d, J = 8.78 Hz, 1 H) 7.95 (d, J = 1.76 Hz, 1 H) 9.94 (s, 1 H) | 285 | 1.00 | A |
| 24 | N-(1-((4-(trifluoro-methyl)-cyclohexyl)-methyl)-1H-indol-5-yl)-acrylamide | 1H NMR (400 MHz, DMSO-d6) mixture of isomers 60/40 δ ppm 0.91-1.93 (m, 9 H) 2.09-2.24 (m, 1 H) 4.00 (d, J = 7.28 Hz, 1.2 H) 4.14 (d, J = 7.78 Hz, 0.8 H) 5.70 (dd, J = 10.04, 2.01 Hz, 1 H) 6.23 (dd, J = 16.94, 2.01 Hz, 1 H) 6.38 (d, J = 3.01 Hz, 1 H) 6.45 (dd, J = 17.07, 10.04 Hz, 1 H) 7.22-7.37 (m, 2 H) 7.41 (d, J = 8.78 Hz, 1 H) 7.91-8.01 (m, 1 H) 9.94 (s, 1 H) | 351 | 1.46 | A |
| 25 | N-(1-((1,1-difluoro-spiro[2.3]hexan-5-yl)-methyl)-1H-indol-5-yl)-acrylamide | 1H NMR (400 MHz, DMSO-d6)) mixture of isomers 65/35 δ ppm 1.32-1.43 (m, 2 H) 1.94-2.25 (m, 4 H) 2.78-3.02 (m, 1 H) 4.22 (d, J = 7.53 Hz, 0.70 H) 4.27 (d, J = 7.28 Hz, 1.3 H) 5.70 (dd, J = 10.04, 2.01 Hz, 1 H) 6.23 (dd, J = 16.94, 2.01 Hz, 1 H) 6.39 (d, J = 3.01 Hz, 1 H) 6.45 (dd, J = 16.94, 10.04 Hz, 1 H) 7.28-7.50 (m, 3 H) 7.96 (d, J = 1.51 Hz, 1 H) 9.94 (s, 1 H) | 317 | 1.36 | A |
| 26 | N-(1-((3-fluoro-cyclopentyl)-methyl)-1H-indol-5-yl)-acrylamide | 1H NMR (400 MHz, DMSO-d6) δ ppm 1.27-2.12 (m, 6 H) 2.57-2.65 (m, 1 H) 4.11 (d, J = 7.28 Hz, 2 H) 5.15 (dt, J = 54.89, 5.16 Hz, 1 H) 5.70 (dd, J = 10.16, 2.13 Hz, 1 H) 6.23 (dd, J = 16.94, 2.13 Hz, 1 H) 6.39 (d, J = 3.01 Hz, 1 H) 6.45 (dd, J = 16.94, 10.16 Hz, 1 H) 7.31 (dd, J = 8.91, 1.88 Hz, 1 H) 7.36 (d, J = 3.01 Hz, 1 H) 7.45 (d, J = 8.91 Hz, 1 H) 7.96 (d, J = 1.88 Hz, 1 H) 9.94 (s, 1 H) | 287 | 3.92 | A' |
| 27 | N-(1-(cyclohexyl-methyl)-1H-indol-5-yl)-acrylamide | 1H NMR (400 MHz, DMSO-d6) δ ppm 0.88-1.22 (m, 5 H) 1.49 (br d, J = 12.55 Hz, 2 H) 1.55-1.70 (m, 3 H) 1.72-1.87 (m, 1 H) 3.97 (d, J = 7.28 Hz, 2 H) 5.69 (dd, J = 10.16, 2.13 Hz, 1 H) 6.22 (dd, J = 16.94, 2.13 Hz, 1 H) 6.37 (d, J = 3.01 Hz, 1 H) 6.45 (dd, J = 16.94, 10.16 Hz, 1 H) 7.27-7.33 (m, 2 H) 7.40 (d, J = 8.78 Hz, 1 H) 7.95 (d, J = 1.51 Hz, 1 H) 9.93 (s, 1 H) | 283 | 1.47 | A |
| 28 | N-(1-((3-(trifluoro-methyl)cyclo-butyl)methyl)-1H-indol-5-yl)-acrylamide | 1H NMR (400 MHz, DMSO-d6)) mixture of isomers 70/30 δ ppm 1.81-1.93 (m, 1 H) 1.97-2.20 (m, 2 H) 2.64-2.88 (m, 1 H) 3.92-3.13 (m, 1 H) 3.19-3.27 (m, 1 H) 4.15 (d, J = 6.78 Hz, 0.6 H) 4.27 (d, J = 7.53 Hz, 1.4 H) 5.69 (dd, J = 10.04, 2.01 Hz, 1 H) 6.23 (dd, J = 17.07, 2.01 Hz, 1 H) 6.38 (d, J = 3.26 Hz, 1 H) 6.45 (dd, J = 17.07, 10.04 Hz, 1 H) 7.27-7.43 (m, 2 H) 7.48 (d, J = 8.78 Hz, 1 H) 7.96 (d, J = 1.25 Hz, 1 H) 9.94 (s, 1 H) | 323 | 1.39 | A |
| 29 | N-(1-((3,3-difluorocyclo-pentyl)methyl)-1H-indol-5-yl)-acrylamide | 1H NMR (400 MHz, DMSO-d6) δ ppm 1,42-1.62 (m, 1 H) 1.69-2.28 (m, 5 H) 2.57-2.65 (m, 1 H) 4.01-4.25 (m, 2 H) 5.70 (dd, J = 10.04, 2.01 Hz, 1 H) 6.23 (dd, J = 16.94, 2.01 Hz, 1 H) 6.40 (d, J = 2.51 Hz, 1 H) 6.45 (dd, J = 16.94, 10.04 Hz, 1 H) 7.31 (dd, J = 8.78, 2.01 Hz, 1 H) 7.37 (d, J = 2.51 Hz, 1 H) 7.46 (d, J = 8.78 Hz, 1 H) 7.97 (d, J = 2.01 Hz, 1 H) 9.95 (s, 1 H) | 305 | 1.38 | A |

-continued

| ex No | IUPAC name | NMR Description | [M + H]+ | Tr (min) | Analytical method |
|---|---|---|---|---|---|
| 30 | N-(1-([1,1'-biphenyl]-4-yl-methyl)-1H-indol-5-yl)-acrylamide | 1H NMR (400 MHz, DMSO-d6) δ ppm 5.44 (s, 2 H) 5.70 (dd, J = 10.16, 2.13 Hz, 1 H) 6.22 (dd, J = 16.94, 2.13 Hz, 1 H) 6.38-6.54 (m, 2 H) 7.23-7.37 (m, 4 H) 7.38-7.47 (m, 3 H) 7.51 (d, J = 3.01 Hz, 1 H) 7.55-7.65 (m, 4 H) 8.00 (d, J = 1.66 Hz, 1 H) 9.95 (s, 1 H) | 353 | 1.46 | A |
| 31 | N-(1-((3'-(trifluoro-methyl)-[1,1'-biphenyl]-4-yl)-methyl)-1H-indol-5-yl)-acrylamide | 1H NMR (400 MHz, DMSO-d6) δ ppm 5.46 (s, 2 H) 5.70 (dd, J = 10.04, 2.01 Hz, 1 H) 6.22 (dd, J = 17.07, 2.01 Hz, 1 H) 6.40-6.54 (m, 2 H) 7.25-7.34 (m, 3 H) 7.41 (d, J = 8.78 Hz, 1 H) 7.52 (d, J = 3.26 Hz, 1 H) 7.64-7.73 (m, 4 H) 7.89-7.96 (m, 2 H) 8.00 (d, J = 1.76 Hz, 1 H) 9.95 (s, 1 H) | 421 | 1.53 | A |
| 32 | N-(1-((4'-(trifluoro-methyl)-[1,1'-biphenyl]-4-yl)methyl)-1H-indol-5-yl)-acrylamide | 1H NMR (400 MHz, DMSO-d6) δ ppm 5.46 (s, 2 H) 5.69 (dd, J = 10.24, 2.11 Hz, 1 H) 6.22 (dd, J = 16.94, 2.11 Hz, 1 H) 6.40-6.53 (m, 2 H) 7.25-7.34 (m, 3 H) 7.42 (d, J = 8.78 Hz, 1 H) 7.52 (d, J = 3.01 Hz, 1 H) 7.67 (d, J = 8.30, 2 H) 7.78 (d, J = 8.53 Hz, 2 H) 7.84 (d, J = 8.53 Hz, 2 H) 8.00 (d, J = 1.76 Hz, 1 H) 9.95 (s, 1 H) | 421 | 1.54 | A |
| 33 | N-(1-((trans)-4-(trifluoro-methyl)-cyclohexyl)-1H-indol-5-yl)-acrylamide | 1H NMR (400 MHz, DMSO-d6) δ ppm 1.52-1.73 (m, 2 H) 1.81-1.97 (m, 2 H) 1.98-2.11 (m, 4 H) 2.38-2.48 (m, 1 H) 4.30-4.50 (m, 1 H) 5.70 (dd, J = 2.13, 10.06 Hz, 1 H) 6.23 (dd, J = 16.94, 2.13 Hz, 1 H) 6.39-6.53 (m, 2 H) 7.31 (dd, J = 8.78, 2.01 Hz, 1 H) 7.40 (d, J = 3.26 Hz, 1 H) 7.52 (d, J = 8.78 Hz, 1 H) 7.96 (d, J = 2.01 Hz, 1 H) 9.94 (s, 1 H) | 337 | 1.46 | A |
| 34 | N-(1-((cis)-4-(trifluoro-methyl)-cyclohexyl)-1H-indol-5-yl)-acrylamide | 1H NMR (400 MHz, DMSO-d6) δ ppm 1.82-2.11 (m, 8 H) 2.55-2.65 (m, 1 H) 4.40-4.58 (m, 1 H) 5.70 (dd, J = 10.04, 2.01 Hz, 1 H) 6.23 (dd, J = 16.94, 2.01 Hz, 1 H) 6.37-6.52 (m, 2 H) 7.32 (dd, J = 8.91, 1.88 Hz, 1 H) 7.40-7.51 (m, 2 H) 7.97 (d, J = 1.88 Hz, 1 H) 9.95 (s, 1 H) | 337 | 1.44 | A |
| 35 | N-(1-((1-(4-(trifluoro-methyl)phenyl)-piperidin-4-yl)-methyl)-1H-indol-5-yl)-acrylamide | 1H NMR (400 MHz, DMSO-d6) δ ppm 1.21-1.39 (m, 2 H) 1.52 (br d, J = 10.79 Hz, 2 H) 1.99-2.14 (m, 1 H) 2.69-2.83 (m, 2 H) 3.86 (br d, J = 12.80 Hz, 2 H) 4.07 (d, J = 7.28 Hz, 2 H) 5.70 (dd, J = 10.04, 2.01 Hz, 1 H) 6.23 (dd, J = 16.94, 2.01 Hz, 1 H) 6.39 (d, J = 1.76 Hz, 1 H) 6.46 (dd, J = 16.94, 10.04 Hz, 1 H) 7.02 (d, J = 8.78 Hz, 2 H) 7.26-7.37 (m, 2 H) 7.41-7.53 (m, 3 H) 7.96 (d, J = 1.76 Hz, 1 H) 9.94 (s, 1 H) | 428 | 1.58 | A |
| 36 | N-(1-(2-(methyl(2,2,2-trifluoroethyl)-amino)ethyl)-1H-indol-5-yl)-acrylamide | 1H NMR (400 MHz, DMSO-d6) δ ppm 2.40 (s, 3 H) 2.92 (t, J = 6.78 Hz, 2 H) 3.16-3.28 (m, 2 H) 4.23 (t, J = 6.78 Hz, 2 H) 5.70 (dd, J = 10.04, 2.01 Hz, 1 H) 6.23 (dd, J = 16.94, 2.01 Hz, 1 H) 6.38 (d, J = 2.76 Hz, 1 H) 6.45 (dd, J = 16.94, 10.04 Hz, 1 H) 7.31 (dd, J = 8.78, 1.76 Hz, 1 H) 7.35 (d, J = 2.76 Hz, 1 H) 7.43 (d, J = 8.78 Hz, 1 H) 7.96 (d, J = 1.76 Hz, 1 H) 9.94 (s, 1 H) | 326 | 1.24 | A |
| 37 | N-(1-(2-(2,2,2-trifluoroethoxy)-ethyl)-1H-indol-5-yl)-acrylamide | 1H NMR (400 MHz, DMSO-d6) δ ppm 3.90 (t, J = 5.40 Hz, 2 H) 3.95-4.08 (m, 2 H) 4.35 (t, J = 5.40 Hz, 2 H) 5.70 (dd, J = 10.16, 2.01 Hz, 1 H) 6.23 (dd, J = 17.07, 2.01 Hz, 1 H) 6.39 (d, J = 3.01 Hz, 1 H) 6.45 (dd, J = 17.07, 10.16 Hz, 1 H) 7.26-7.36 (m, 2 H) 7.44 (d, J = 8.78 Hz, 1 H) 7.96 (d, J = 1.76 Hz, 1 H) 9.94 (s, 1 H) | 313 | 1.17 | A |
| 38 | N-(1-(1-(2,2,2-trifluoroethyl)-piperidin-4-yl)-1H-indol-5-yl)-acrylamide | 1H NMR (400 MHz, DMSO-d6) δ ppm 1.84-2.07 (m, 4 H) 2.58-2.71 (m, 2 H) 3.06 (br d, J = 11.80 Hz, 2 H) 3.19-3.29 (m, 2 H) 4.27-4.40 (m, 1 H) 5.69 (dd, J = 10.07-2.13, 1 H) 6.23 (dd, J = 16.94, 2.13 Hz, 1 H) 6.38-6.53 (m, 2 H) 7.31 (dd, J = 8.91, 1.88 Hz, 1 H) 7.44-7.54 (m, 2 H) 7.96 (d, J = 1.76 Hz, 1 H) 9.94 (s, 1 H) | 352 | 1.12 | A |
| 39 | N-(1-(4,4-difluorocyclo-hexyl)-1H-indol-5-yl)-acrylamide | 1H NMR (400 MHz, DMSO-d6) δ ppm 1.91-2.29 (m, 8 H) 4.51-4.65 (m, 1 H) 5.70 (dd, J = 10.04, 2.01 Hz, 1 H) 6.23 (dd, J = 16.94, 2.01 Hz, 1 H) 6.40-6.52 (m, 2 H) 7.33 (dd, J = 8.91, 1.88 Hz, 1 H) 7.44-7.54 (m, 2 H) 7.97 (d, J = 1.88 Hz, 1 H) 9.95 (s, 1 H) | 305 | 1.38 | A |

-continued

| ex No | IUPAC name | NMR Description | [M + H]+ | Tr (min) | Analytical method |
|---|---|---|---|---|---|
| 40 | N-(1-(1-(4-(trifluoro-methyl)phenyl)-piperidin-4-yl)-1H-indol-5-yl)-acrylamide | 1H NMR (400 MHz, DMSO-d6) δ ppm 1.94-2.14 (m, 4 H) 3.02-3.15 (m, 2 H) 4.06 (br d, J = 12.80 Hz, 2 H) 4.53-4.68 (m, 1 H) 5.70 (dd, J = 10.07, 2.13 Hz, 1 H) 6.23 (dd, J = 16.94, 2.13 Hz, 1 H) 6.38-6.51 (m, 2 H) 7.14 (d, J = 8.78 Hz, 2 H) 7.33 (dd, J = 8.78, 1.76 Hz, 1 H) 7.47 (d, J = 3.26 Hz, 1 H) 7.49-7.57 (m, 3 H) 7.97 (d, J = 1.76 Hz, 1 H) 9.95 (s, 1 H) | 414 | 1.53 | A |
| 41 | N-(1-(3-(3,3-difluoro-pyrrolidin-1-yl)-propyl)-1H-indol-5-yl)-acrylamide | 1H NMR (400 MHz, DMSO-d6) δ ppm 1.89 (quin, J = 6.84 Hz, 2 H) 2.17-2.36 (m, 4 H) 2.64 (t, J = 7.03 Hz, 2 H) 2.83 (t, J = 13.43 Hz, 2 H) 4.18 (t, J = 6.78 Hz, 2 H) 5.69 (dd, J = 10.08, 2.13 Hz, 1 H) 6.23 (dd, J = 16.94, 2.13 Hz, 1 H) 6.39 (d, J = 2.76 Hz, 1 H) 6.45 (dd, J = 16.94, 10.08 Hz, 1 H) 7.27-7.36 (m, 2 H) 7.41 (d, J = 8.69 Hz, 1 H) 7.97 (d, J = 1.76 Hz, 1 H) 9.94 (s, 1 H) | 334 | 1.05 | A |
| 42 | N-(1-(4-(trimethylsilyl)-benzyl)-1H-indol-5-yl)-acrylamide | 1H NMR (400 MHz, DMSO-d6) δ ppm 0.14-0.24 (m, 9 H) 5.37 (s, 2 H) 5.69 (dd, J = 10.16, 2.13 Hz, 1 H) 6.22 (dd, J = 17.07, 2.13 Hz, 1 H) 6.38-6.50 (m, 2 H) 7.16 (d, J = 8.03 Hz, 2 H) 7.26 (dd, J = 8.78, 2.01 Hz, 1 H) 7.37 (d, J = 8.78 Hz, 1 H) 7.41-7.50 (m, 3 H) 7.98 (d, J = 2.01 Hz, 1 H) 9.94 (s, 1 H) | 349 | 1.55 | A |
| 43 | N-(1-(3-(trifluoro-methyl)phenyl)-1H-indol-5-yl)-acrylamide | 1H NMR (400 MHz, DMSO-d6) δ ppm 5.73 (dd, J = 10.15, 1.94 Hz, 1 H) 6.25 (dd, J = 16.94, 1.94 Hz, 1 H) 6.47 (dd, J = 16.94 10.15 Hz, 1 H) 6.73 (d, J = 3.26 Hz, 1 H) 7.40 (dd, J = 8.78, 2.01 Hz, 1 H) 7.55 (d, J = 8.78 Hz, 1 H) 7.70-7.86 (m, 3 H) 7.89-8.02 (m, 2 H) 8.15 (d, J = 2.01 Hz, 1 H) 10.13 (s, 1 H) | 331 | 1.37 | A |
| 44 | N-(1-(4-(trifluoro-methyl)phenyl)-1H-indol-5-yl)-acrylamide | 1H NMR (400 MHz, DMSO-d6) δ ppm 5.73 (dd, J = 10.13, 2.01 Hz, 1 H) 6.26 (dd, J = 17.07, 2.01 Hz, 1 H) 6.4- (dd, J = 17.07, 10.13 Hz, 1 H) 6.76 (d, J = 2.76 Hz, 1 H) 7.42 (dd, J = 8.78, 2.01 Hz, 1 H) 7.65 (d, J = 8.78 Hz, 1 H) 7.77 (d, J = 2.76 Hz, 1 H) 7.85 (d, J = 8.36 Hz, 2 H) 7.93 (d, J = 8.36 Hz, 2 H) 8.14 (d, J = 2.01 Hz, 1 H) 10.14 (s, 1 H) | 331 | 1.39 | A |
| 45 | N-(1-(6-(trifluoro-methyl)pyridin-3-yl)-1H-indol-5-yl)-acrylamide | 1H NMR (400 MHz, DMSO-d6) δ ppm 5.74 (dd, J = 10.13, 2.01 Hz, 1 H) 6.26 (dd, J = 17.07, 2.01 Hz, 1 H) 6.47 (dd, J = 17.07, 10.13 Hz, 1 H) 6.81 (d, J = 3.51 Hz, 1 H) 7.45 (dd, J = 8.91, 1.88 Hz, 1 H) 7.70 (d, J = 8.91 Hz, 1 H) 7.85 (d, J = 3.51 Hz, 1 H) 8.09 (d, J = 8.28 Hz, 1 H) 8.15 (d, J = 1.88 Hz, 1 H) 8.36 (dd, J = 8.28, 2.26 Hz, 1 H) 9.09 (d, J = 2.26 Hz, 1 H) 10.12 (s, 1 H) | 332 | 1.19 | A |
| 46 | N-(1-(5-(trifluoro-methyl)pyridin-2-yl)-1H-indol-5-yl)-acrylamide | 1H NMR (400 MHz, DMSO-d6) δ ppm 5.74 (dd, J = 10.04, 2.01 Hz, 1 H) 6.27 (dd, J = 16.81, 2.01 Hz, 1 H) 6.48 (dd, J = 16.81, 10.04 Hz, 1 H) 6.83 (d, J = 3.51 Hz, 1 H) 7.46 (dd, J = 9.03, 2.01 Hz, 1 H) 7.99 (d, J = 8.78 Hz, 1 H) 8.12-8.20 (m, 2 H) 8.32 (dd, J = 8.78, 2.38 Hz, 1 H) 8.52 (d, J = 9.03 Hz, 1 H) 8.93 (d, J = 2.38 Hz, 1 H) 10.15 (s, 1 H) | 332 | 1.31 | A |
| 47 | N-(1-(pyridin-3-yl)-1H-indol-5-yl)-acrylamide | 1H NMR (400 MHz, DMSO-d6) δ ppm 5.73 (dd, J = 10.16, 1.88 Hz, 1 H) 6.26 (dd, J = 16.81, 1.88 Hz, 1 H) 6.47 (dd, J = 16.81, 10.16 Hz, 1 H) 6.74 (d, J = 3.01 Hz, 1 H) 7.41 (dd, J = 8.91, 1.88 Hz, 1 H) 7.55 (d, J = 8.91 Hz, 1 H) 7.58-7.64 (m, 1 H) 7.73 (d, J = 3.01 Hz, 1 H) 8.04-8.10 (m, 1 H) 8.13 (d, J = 1.88 Hz, 1 H) 8.59 (dd, J = 4.77, 1.25 Hz, 1 H) 8.86 (d, J = 1.25 Hz, 1 H) 10.08 (s, 1 H) | 264 | 0.79 | A |
| 48 | N-(1-(4-fluoro-phenyl)-1H-indol-5-yl)-acrylamide | 1H NMR (400 MHz, DMSO-d6) δ ppm 5.72 (dd, J = 10.16, 2.13 Hz, 1 H) 6.25 (dd, J = 17.07, 2.13 Hz, 1 H) 6.47 (dd, J = 17.07, 10.16 Hz, 1 H) 6.67 (d, J = 3.26 Hz, 1 H) 7.32-7.50 (m, 4 H) 7.57-7.67 (m, 3 H) 8.11 (d, J = 1.76 Hz, 1 H) 10.06 (s, 1 H) | 281 | 1.22 | A |
| 49 | N-(1-(3,4-difluorophenyl)-1H-indol-5-yl)-acrylamide | 1H NMR (400 MHz, DMSO-d6) δ ppm 5.73 (dd, J = 10.04, 2.01 Hz, 1 H) 6.25 (dd, J = 17.07, 2.01 Hz, 1 H) 6.46 (dd, J = 17.07, 10.04 Hz, 1 H) 6.69 (d, J = 3.26 Hz, 1 H) 7.40 (dd, J = 8.91, | 299 | 1.26 | A |

-continued

| ex No | IUPAC name | NMR Description | [M + H]+ | Tr (min) | Analytical method |
|---|---|---|---|---|---|
| | | 1.88 Hz, 1 H) 7.44-7.50 (m, 1 H) 7.54 (d, J = 8.91 Hz, 1 H) 7.59-7.70 (m, 2 H) 7.71-7.81 (m, 1 H) 8.12 (d, J = 1.88 Hz, 1 H) 10.08 (s, 1 H) | | | |
| 50 | N-(1-(3-(methyl-sulfonyl)-phenyl)-1H-indol-5-yl)-acrylamide | 1H NMR (400 MHz, DMSO-d6) δ ppm 3.34 (s, 3 H) 5.73 (dd, J = 10.04, 2.01 Hz, 1 H) 6.26 (dd, J = 16.94, 2.02 Hz, 1 H) 6.47 (dd, J = 16.94, 10.04 Hz, 1 H) 6.76 (d, J = 3.26 Hz, 1 H) 7.42 (dd, J = 8.91, 1.88 Hz, 1 H) 7.59 (d, J = 8.91 Hz, 1 H) 7.78 (d, J = 3.26 Hz, 1 H) 7.82-7.88 (m, 1 H) 7.89-7.95 (m, 1 H) 7.97-8.03 (m, 1 H) 8.05-8.09 (m, 1 H) 8.15 (d, J = 1.88 Hz, 1 H) 10.11 (s, 1 H) | 341 | 0.97 | A |
| 51 | N-(1-(4-cyano-phenyl)-1H-indol-5-yl)-acrylamide | 1H NMR (400 MHz, DMSO-d6) δ ppm 5.74 (dd, J = 9.79, 2.26 Hz, 1 H) 6.26 (dd, J = 16.81, 2.26 Hz, 1 H) 6.46 (dd, J = 16.81, 9.79 Hz, 1 H) 6.77 (d, J = 3.26 Hz, 1 H) 7.43 (dd, J = 9.03, 2.01 Hz, 1 H) 7.66 (d, J = 9.03 Hz, 1 H) 7.77 (d, J = 3.26 Hz, 1 H) 7.83 (d, J = 8.53 Hz, 2 H) 8.02 (d, J = 8.53 Hz, 2 H) 8.13 (d, J = 2.01 Hz, 1 H) 10.12 (s, 1 H) | 288 | 1.07 | A |
| 52 | N-(1-(3,5-difluorobenzyl)-1H-indol-5-yl)acrylamide | 1H NMR (400 MHz, DMSO-d6) δ ppm 5.43 (s, 2 H) 5.70 (dd, J = 10.04, 2.01 Hz, 1 H) 6.22 (dd, J = 16.94, 2.13 Hz, 1 H) 6.39-6.54 (m, 2 H) 6.86 (br d, J = 6.27 Hz, 2 H) 7.11 (tt, J = 9.38, 2.29 Hz, 1 H) 7.29 (dd, J = 8.78, 1.76 Hz, 1 H) 7.40 (d, J = 8.78 Hz, 1 H) 7.51 (d, J = 3.01 Hz, 1 H) 8.01 (d, J = 1.51 Hz, 1 H) 9.96 (s, 1 H) | 313 | 1.22 | A |
| 53 | N-(1-(3,4-difluorobenzyl)-1H-indol-5-yl)-acrylamide | 1H NMR (400 MHz, DMSO-d6) δ ppm 5.38 (s, 2 H) 5.70 (dd, J = 10.04, 2.01 Hz, 1 H) 6.22 (dd, J = 17.07, 2.01 Hz, 1 H) 6.37-6.54 (m, 2 H) 7.01 (ddd, J = 6.21, 4.08, 2.26 Hz, 1 H) 7.23-7.46 (m, 4 H) 7.50 (d, J = 3.01 Hz, 1 H) 7.99 (d, J = 1.76 Hz, 1 H) 9.95 (s, 1 H) | 313 | 1.22 | A |
| 54 | N-(1-(3-cyanobenzyl)-1H-indol-5-yl)-acrylamide | 1H NMR (400 MHz, DMSO-d6) δ ppm 5.46 (s, 2 H) 5.70 (dd, J = 10.04, 2.01 Hz, 1 H) 6.22 (dd, J = 16.94, 2.13 Hz, 1 H) 6.36-6.55 (m, 2 H) 7.28 (dd, J = 8.91, 1.88 Hz, 1 H) 7.36-7.57 (m, 4 H) 7.62-7.77 (m, 2 H) 8.00 (d, J = 1.76 Hz, 1 H) 9.95 (s, 1 H) | 302 | 1.08 | A |
| 55 | N-(1-((5-(trifluoro-methyl)furan-2-yl)-methyl)-1H-indol-5-yl)-acrylamide | 1H NMR (400 MHz, DMSO-d6) δ ppm 5.50 (s, 2 H) 5.70 (dd, J = 10.04, 2.13 Hz, 1 H) 6.23 (dd, J = 16.94, 2.13 Hz, 1 H) 6.38-6.51 (m, 2 H) 6.59 (d, J = 3.01 Hz, 1 H) 7.14 (d, J = 3.01, 1 H) 7.33 (dd, J = 8.91, 1.88 Hz, 1 H) 7.42 (d, J = 3.01 Hz, 1 H) 7.51 (d, J = 8.91 Hz, 1 H) 7.98 (d, J = 1.8 Hz, 1 H) 9.97 (s, 1 H) | 335 | 1.26 | A |
| 56 | N-(1-(thiazol-4-ylmethyl)-1H-indol-5-yl)acrylamide | 1H NMR (400 MHz, DMSO-d6) δ ppm 5.50 (s, 2 H), 5.69 (dd, J = 10.16, 2.13 Hz, 1 H), 6.22 (dd, J = 16.94, 2.13 Hz, 1 H), 6.36-6.53 (m, 2 H), 7.29 (dd, J = 8.78, 1.76 Hz, 1 H), 7.38-7.58 (m, 3 H), 7.97 (d, J = 1.76 Hz, 1 H), 9.04 (d, J = 1.76 Hz, 1 H), 9.94 (s, 1 H) | 284 | 0.87 | A |
| 57 | N-(1-((2-(trifluoro-methyl)thiazol-4-yl)methyl)-1H-indol-5-yl)-acrylamide | 1H NMR (400 MHz, DMSO-d6) δ ppm 5.59 (s, 2 H), 5.70 (dd, J = 10.04, 2.01 Hz, 1 H), 6.23 (dd, J = 16.94, 2,01 Hz, 1 H), 6.39-6.57 (m, 2 H), 7.31 (dd, J = 8.78, 1.76 Hz, 1 H), 7.43-7.57 (m, 2 H), 7.81 (s, 1 H), 7.99 (d, J = 1.51 Hz, 1 H), 9.96 (s, 1 H) | 352 | 1.18 | A |
| 58 | N-(1-(3-(trifluoro-methyl)benzyl)-1H-indol-7-yl)-acrylamide | 1H NMR (400 MHz, DMSO-d6) δ ppm 5.55 (s, 2 H), 5.68 (dd, J = 10.16, 2.01 Hz, 1 H), 6.12 (dd, J = 17.07, 2.01 Hz, 1 H), 6.33 (dd, J = 17.07, 10.16 Hz, 1 H), 6.59 (d, J = 3.26 Hz, 1 H), 6.88 (d, J = 7.03 Hz, 1 H), 6.95-7.13 (m, 2 H), 7.23 (s, 1 H), 7.37-7.68 (m, 4 H), 9.79 (s, 1 H) | 345 | 1.44 | A |
| 59 | N-(1-(3-(methyl-sulfonyl)-benzyl)-1H-indol-5-yl)-acrylamide | 1H NMR (400 MHz, DMSO-d6) δ ppm 3.18 (s, 3 H), 5.53 (s, 2 H), 5.70 (dd, J = 10.29, 2.13 Hz, 1 H), 6.22 (dd, J = 16.94, 2.13 Hz, 1 H), 6.41-6.53 (m, 2 H), 7.29 (dd, J = 8.78, 2.01 Hz, 1 H), 7.37-7.47 (m, 2 H), 7.52 (d, J = 3.26 Hz, 1 H), 7.58 (t, J = 8.03 Hz, 1 H), 7.74-7.89 (m, 2 H), 8.00 (d, J = 1.76 Hz, 1 H), 9.95 (s, 1 H) | 355 | 0.95 | A |
| 60 | N-(3-methoxy-methyl)-1-(3- | 1H NMR (400 MHz, DMSO-d6) δ = 10.02 (s, 1H), 7.99 (d, J = 1.2 Hz, 1H), 7.63-7.52 (m, | 357 [M + H − | 0.97 | D |

-continued

| ex No | IUPAC name | NMR Description | [M + H]+ | Tr (min) | Analytical method |
|---|---|---|---|---|---|
| | (trifluoro-methyl)benzyl)-1H-indol-5-yl)-acrylamide | 4H), 7.44-7.35 (m, 3H), 6.45-6.41 (m, 1H), 6.22 (dd, J = 2.0, 16.8 Hz, 1H), 5.70 (dd, J = 2.0, 10.0 Hz, 1H), 5.49 (s, 2H), 4.53 (s, 2H), 3.24 (s, 3H) | CH3OH]+ | | |
| 61 | methyl 5-acrylamido-1-(3-(trifluoro-methyl)-benzyl)-1H-indole-3-carboxylate | 1H NMR (400 MHz, DMSO-d6) δ = 10.15 (s, 1H), 8.37-8.35 (m, 2H), 7.73 (s, 1H), 7.65 (d, J = 7.6 Hz, 1H), 7.60-7.51 (m, 4H), 6.50-6.43 (m, 1H), 6.25 (dd, J = 2.4, 17.2 Hz, 1H), 5.73 (dd, J = 2.0, 10.0 Hz, 1H), 5.60 (s, 2H), 3.82 (s, 3H). | 403 | 0.97 | D |
| 62 | N-(1-(3-(trifluoro-methyl)phenyl)-1H-indol-6-yl)-acrylamide | 1H NMR (400 MHz, DMSO-d6) δ = 10.18 (s, 1H), 8.25 (s, 1H), 7.93-7.89 (m, 2H), 7.85 (t, J = 6.8 Hz, 1H), 7.80-7.76 (m, 1H), 7.70 (d, J = 3.2 Hz, 1H), 7.60 (d, J = 8.4 Hz, 1H), 7.33 (dd, J = 1.6, 8.4 Hz, 1H), 6.70 (dd, J = 0.8, 3.6 Hz, 1H), 6.43-6.41 (m, 1H), 6.25 (dd, J = 2.2, 16.8 Hz, 1H), 5.74-5.71 (m, 1H). | 331 | 0.80 | C |
| 63 | N-(1-(4-(pentafluoro-l6-sulfanyl)-phenyl)-1H-indol-5-yl)-acrylamide | 1H NMR (400 MHz, DMSO-d6) δ = 10.13 (s, 1H), 8.14 (d, J = 1.6 Hz, 1H), 8.08 (d, J = 9.2 Hz, 2H), 7.85 (d, J = 8.8 Hz, 2H), 7.78 (d, J = 3.2 Hz, 1H), 7.68 (d, J = 8.8 Hz, 1H), 7.44 (dd, J = 1.6, 8.8 Hz, 1H), 6.77 (d, J = 3.6 Hz, 1H), 6.50-6.43 (m, 1H), 6.26 (dd, J = 2.0, 17.2 Hz, 1H), 5.74 (dd, J = 2.0, 14.0 Hz, 1H) | 389 | 0.95 | C |
| 64 | N-(1-(4-(trifluoro-methyl)phenyl)-1H-indol-6-yl)acrylamide | 1H NMR (400 MHz, DMSO-d6) δ = 10.21 (s, 1H), 8.35 (s, 1H), 7.98 (d, J = 8.4 Hz, 2H), 7.83 (d, J = 8.4 Hz, 2H), 7.69 (d, J = 3.2 Hz, 1H), 7.61 (d, J = 8.6 Hz, 1H), 7.32 (dd, J = 1.6, 8.4 Hz, 1H), 6.72 (d, J = 3.2 Hz, 1H), 6.51-6.40 (m, 1H), 6.24 (dd, J = 2.0, 10.0 Hz, 1H), 5.74 (dd, J = 2.0, 10.0 Hz, 1H) | 331 | 1.00 | C |
| 65 | N-(1-(2-methyl-4-(trifluoro-methyl)phenyl)-1H-indol-5-yl)-acrylamide | 1H NMR (400 MHz, CDCl3-d) δ = 8.03 (s, 1H, Ar), 7.67 (s, 1H, Ar), 7.61 (d, J = 8.4 Hz, 1H, Ar), 7.44 (d, J = 8.0 Hz, 1H, Ar), 7.30 (s, 1H, Ar), 7.17 (d, J = 3.2 Hz, 1H, Ar), 6.99 (d, J = 8.8 Hz, 1H, Ar), 6.69 (d, J = 3.2 Hz, 1H, Ar), 6.44 (d, J = 16.0 Hz, 1H, CHCH2), 6.32 (dd, J = 10.4, 16.0 Hz,1H, CHCH2), 5.78 (d, J = 10.4 Hz, 1H, CHCH2), 2.16 (s, 3H, CH3) | 345 | 1.06 | C |
| 66 | N-(1-(3,5-di-fluorophenyl)-1H-indol-5-yl)acrylamide | 1H NMR (400 MHz, DMSO-d6) δ ppm 5.74 (dd, J = 10.04, 2.13 Hz, 1 H), 6.26 (dd, J = 16.94, 2.13 Hz, 1 H), 6.47 (dd, J = 17.07, 10.04 Hz, 1 H), 6.73 (d, J = 4.02 Hz, 1 H), 7.26 (tt, J = 9.41, 2.26 Hz, 1 H), 7.38-7.48 (m, 3 H), 7.67 (d, J = 8.78 Hz, 1 H), 7.73 (d, J = 3.51 Hz, 1 H), 8.14 (d, J = 1.76 Hz, 1 H), 10.11 (s, 1 H) | 299 | 1.26 | A |
| 67 | N-(1-(5-fluoro-pyridin-3-yl)-1H-indol-5-yl)-acrylamide | 1H NMR (400 MHz, DMSO-d6) δ ppm 5.74 (dd, J = 10.04, 2.01 Hz, 1 H), 6.26 (dd, J = 17.07, 2.01 Hz, 1 H), 6.47 (dd, J = 17.07, 10.04 Hz, 1 H), 6.77 (d, J = 2.76 Hz, 1 H), 7.43 (dd, J = 8.91, 1.88 Hz, 1 H), 7.64 (d, J = 8.91 Hz, 1 H), 7.77 (d, J = 3.26 Hz, 1 H), 8.06-8.21 (m, 2 H), 8.61 (d, J = 2.51 Hz, 1 H), 8.80 (t, J = 1.51 Hz, 1 H), 10.10 (s, 1 H) | 282 | 0.97 | A |
| 68 | N-(1-(2-(trifluoro-methyl)pyridin-4-yl)-1H-indol-5-yl)-acryl-amide | 1H NMR (400 MHz, DMSO-d6) δ ppm 5.75 (dd, J = 10.15, 2.01 Hz, 1 H) 6.27 (dd, J = 17.07, 2.01 Hz, 1 H) 6.47 (dd, J = 17.07, 10.15 Hz, 1 H) 6.84 (d, J = 3.26 Hz, 1 H) 7.48 (dd, J = 9.03, 2.01 Hz, 1 H) 7.83 (d, J = 9.03 Hz, 1 H) 7.98 (d, J = 3.26 Hz, 1 H) 8.04 (dd, J = 5.52, 2.01 Hz, 1 H) 8.12 (d, J = 2.01 Hz, 2 H) 8.17 (d, J = 2.01 Hz, 1H ) 8.85 (d, J = 5.52 Hz, 1 H) 10.16 (s, 1 H) | 332 | 1.15 | A |
| 69 | N-[3-methyl-1-[4-(trifluoro-methyl)phe-nyl]indol-5-yl] acrylamide | 1H NMR (400 MHz, DMSO-d6) δ = 10.15 (s, 1H, CONH), 8.08 (d, J = 2.0 Hz, 1H, ArH), 7.91-7.88 (m, 2H, ArH), 7.80-7.66 (m, 2H, ArH), 7.64 (d, J = 8.8 Hz, 1H, ArH), 7.58 (d, J = 1.2 Hz, 1H, ArH), 7.43 (dd, J = 2.0, 8.8 Hz, 1H, ArH), 6.48-6.44 (m, 1H, CHCH2), 6.26 (dd, J = 2.0, 17.2 Hz, 1H CHCH2), 5.74 (dd, J = 2.4, 10.0 Hz, 1H CHCH2), 2.30 (d, J = 1.6 Hz, 3H, CH3). | 345 | 1.02 | C |
| 70 | N-[2-methyl-1-[4-(trifluoro-methyl)phe- | 1H NMR (400 MHz, DMSO-d6) δ = 10.03 (s, 1H, CONH), 8.00-7.95 (m, 3H, ArH), 7.71 (d, J = 8.4 Hz, 2H, ArH), 7.25 (dd, J = 2.0, | 345 | 0.92 | C |

-continued

| ex No | IUPAC name | NMR Description | [M + H]+ | Tr (min) | Analytical method |
|---|---|---|---|---|---|
| | nyl]indol-5-yl]-acrylamide | 8.8 Hz, 1H, ArH), 7.09 (d, J = 8.8 Hz, 1H, ArH), 6.46-6.44 (m, 2H, ArH, CHCH2), 6.25-6.21 (m, 1H, CHCH2), 5.73-5.70 (m, 1H, CHCH2), 2.31 (s, 3H, CH3). | | | |
| 71 | N-methyl-N-[2-methyl-1-[4-(trifluoro-methyl)phe-nyl]indol-5-yl]-acrylamide | 1H NMR (400 MHz, DMSO-d6) δ = 7.98 (d, J = 8.4 Hz, 2H, ArH), 7.75 (d, J = 8.4 Hz, 2H, ArH), 7.43 (d, J = 1.6 Hz, 1H, ArH), 7.15 (d, J = 8.4 Hz, 1H, ArH), 6.95 (dd, J = 2.0, 8.4 Hz, 1H, ArH), 6.52 (s, 1H, ArH), 6.11 (d, J = 2.8 Hz, 1H, CHCH2), 6.05 (d, J = 10.0 Hz, 1H, CHCH2), 5.49 (dd, J = 2.4, 10.0 Hz, 1H, CHCH2), 3.26 (s, 3H, CH3), 2.33 (s, 3H, CH3). | 359 | 0.96 | C |
| 72 | N-(3-(methoxy-methyl)-1-(4-(trifluoro-methyl)-phenyl)-1H-indol-5-yl)-acrylamide | 1H NMR (400 MHz, DMSO-d6) δ = 10.17 (s, 1H), 8.12 (d, J = 1.6 Hz, 1H), 7.92 (d, J = 8.8 Hz, 2H), 7.85 (d, J = 8.8 Hz, 2H), 7.79 (s, 1H), 7.65 (d, J = 8.8 Hz, 1H), 7.53 (dd, J = 2.0, 8.8 Hz, 1H), 6.46 (dd, J = 10.0, 16.8 Hz, 1H), 6.26 (dd, J = 2.0, 17.2 Hz, 1H), 5.74 (dd, J = 2.0, 10.0 Hz, 1H), 4.60 (s, 2H), 3.31 (s, 3H); | 343 [M + H − CH3OH]+ | 0.99 | D |
| 73 | N-(6-fluoro-1-(4-(trifluoro-methyl)-phenyl)-1H-indol-5-yl)-acrylamide | 1H NMR (400 MHz, DMSO-d6) δ = 9.87 (s, 1H), 8.19 (d, J = 7.6 Hz, 1H), 7.93 (d, J = 8.4 Hz, 2H), 7.87 (d, J = 8.4 Hz, 2H), 7.79 (d, J = 3.2 Hz, 1H), 7.59 (d, J = 11.6 Hz, 1H), 6.79 (d, J = 2.8 Hz, 1H), 6.60-6.59 (m, 1H), 6.28 (dd, J = 2.0, 17.2 Hz, 1H), 5.76 (dd, J = 2.0, 10.0 Hz, 1H) | 349 | 0.96 | C |
| 74 | N-methyl-N-(1-(4-(trifluoro-methyl)phenyl)-1H-indol-5-yl)acrylamide | 1H NMR (400 MHz, DMSO-d6) δ = 7.96-7.94 (m, 2H), 7.89-7.86 (m, 3H), 7.72 (d, J = 8.8 Hz, 1H), 7.59 (d, J = 2.0 Hz, 1H), 7.14 (dd, J = 2.0, 8.4 Hz, 1H), 6.81 (d, J = 3.2 Hz, 1H), 6.17-6.12 (m, 1H), 6.08-6.06 (m, 1H), 5.53-5.50 (m, 1H), 3.29 (s, 3H) | 345 | 0.83 | C |
| 75 | (E)-N-(1-(4-(trifluoromethyl) phenyl)-1H-indol-5-yl)but-2-enamide | 1H NMR (400 MHz, DMSO-d6) δ = 9.92 (s, 1H), 8.11 (d, J = 1.6 Hz, 1H), 7.92 (d, J = 8.8 Hz, 2H), 7.84 (d, J = 8.8 Hz, 2H), 7.75 (d, J = 3.6 Hz, 1H), 7.63 (d, J = 8.8 Hz, 1H), 7.40 (dd, J = 8.8, 1.6 Hz, 1H), 6.82-6.74 (m, 2H), 6.15 (dd, J = 15.2, 1.6 Hz, 1H), 1.87 (dd, J = 6.8, 1.6 Hz, 3H); | 345 | 0.82 | C |
| 76 | (E)-4-(dimethyl-amino)-N-(1-(4-(tri-fluoro-methyl)phenyl)-1H-indol-5-yl)but-2-en-amide | 1H NMR (400 MHz, CDCL3-d) δ = 8.04 (s, 1H, CONH), 7.79 (d, J = 8.4 Hz, 2H, Ar), 7.62 (d, J = 8.4 Hz, 2H, Ar), 7.53 (d, J = 8.8 Hz, 1H, Ar), 7.38-7.31 (m, 3H, Ar), 6.99 (m, 1H, Ar), 6.70 (d, J = 2.8 Hz, 1H, CHCH), 6.15 (d, J = 15.2 Hz, 1H, CHCH), 3.14 (d, J = 5.6 Hz, 2H, CH2), 2.30 (s, 6H, N(CH3)2) | 388 | 1.03 | D |
| 77 | N-(6-chloro-1-(4-(trifluoro-methyl)phenyl)-1H-indol-5-yl)acrylamide | 1H NMR (400 MHz, DMSO-d6) δ = 9.73 (s, 1H), 7.96 (m, 3H), 7.91-7.87 (m, 2H), 7.85 (d, J = 3.4 Hz, 1H), 7.78 (s, 1H), 6.81 (d, J = 3.2 Hz, 1H), 6.61 (m, 1H), 6.28 (dd, J = 8, 1.8 Hz, 1H), 5.81-5.76 (m, 1H); | 365 | 0.93 | C |
| 78 | N-(6-chloro-1-(3-(trifluoro-methyl)benzyl)-1H-indol-5-yl)acrylamide | 1H NMR (400 MHz, DMSO-d6) δ = 9.63 (s, 1H), 7.82-7.69 (m, 2H), 7.63 (s, 3H), 7.59-7.53 (m, 1H), 7.44 (d, J =3.4 Hz, 1H), 6.64-6.48 (m, 2H), 6.24 (d, J = 8.4 Hz, 1H), 5.75 (d, J = 9.8 Hz, 1H), 5.56 (s, 2H) | 379 | 0.81 | C |
| 79 | N-(7-chloro-1-(3-(trifluoro-methyl)benzyl)-1H-indol-5-yl)acrylamide | 1H NMR (400 MHz, DMSO-d6) δ = 10.12 (s, 1H), 7.92 (d, J = 1.7 Hz, 1H), 7.61 (d, J = 5.0 Hz, 2H), 7.53 (t, J = 7.8 Hz, 1H), 7.46 (d, J = 1.7 Hz, 1H), 7.36 (s, 1H), 7.19 (d, J = 7.6 Hz, 1H), 6.63 (d, J = 3.2 Hz, 1H), 6.45-6.37 (m, 1H), 6.28-6.22 (m, 1H), 5.82 (s, 2H), 5.77-5.72 (m, 1H); | 379 | 0.95 | C |
| 80 | N-(6-fluoro-1-(3-(trifluoro-methyl)benzyl)-1H-indol-5-yl)acrylamide | 1H NMR (400 MHz, DMSO-d6) δ = 9.73 (s, 1H), 7.98 (d, J = 7.6 Hz, 1H), 7.64-7.62 (m, 2H), 7.57-7.44 (m, 4H), 6.61-6.55 (m, 1H), 6.52-5.51 (m, 1H), 6.24 (dd, J = 2.0, 17.2 Hz, 1H), 5.73 (dd, J = 2.0, 10.4 Hz, 1H), 5.50 (s, 2H). | 363 | 0.94 | C |

-continued

| ex No | IUPAC name | NMR Description | $[M + H]^+$ | Tr (min) | Analytical method |
|---|---|---|---|---|---|
| 81 | N-(7-chloro-1-(4-(trifluoro-methyl)phenyl)-1H-indol-5-yl)acrylamide | 1H NMR (400 MHz, DMSO-d6) δ = 10.21 (s, 1H), 8.02 (d, J = 1.6 Hz, 1H), 7.87 (d, J = 8.4 Hz, 2H), 7.68 (d, J = 8.4 Hz, 2H), 7.57 (d, J = 3.6 Hz, 2H), 6.79 (d, J = 3.2 Hz, 1H), 6.48-6.39 (m, 1H), 6.26 (dd, J = 2.0 Hz, 16.8 Hz, 1H), 5.77-5.74 (m, 1H); | 365 | 1.01 | C |
| 82 | N-(3-(hydroxy-methyl)-1-(4-(tri-fluoro-methyl)-phenyl)-1H-indol-5-yl)-acrylamide | 1H NMR (400 MHz, DMSO-d6) δ = 10.15 (s, 1H, CONH), 8.14 (d, J = 2.0 Hz, 1H, Ar), 7.91 (d, J = 8.4 Hz, 2H, Ar), 7.82 (d, J = 8.4 Hz, 2H, Ar), 7.67-7.63 (m, 2H, Ar), 7.50 (dd, J = 1.6, 8.8 Hz, 1H, Ar), 6.47 (dd, J = 10.0, 16.8 Hz, 1H, CHCH2), 6.26 (dd, J = 2.0, 16.8 Hz, 1H, CHCH2), 5.73 (dd, J = 2.0, 10.0 Hz, 1H, CHCH2), 4.99 (s, 1H, OH), 4.69 (s, 2H, CH2); | 343 $[M + H - H2O]^+$ | 0.93 | D |
| 83 | 5-acrylamido-1-(3-(trifluoro-methyl)benzyl)-1H-indole-3-carboxamide | 1H NMR (400 MHz, DMSO-d6) δ = 10.10 (s, 1H, NH), 8.39 (d, J = 1.6 Hz, 1H, Ar), 8.13 (s, 1H, Ar), 7.67-7.63 (m, 3H, Ar), 7.58 (t, J = 7.6 Hz, 1H, Ar), 7.49-7.44 (m, 3H, Ar, NH2), 6.80 (brs, 1H, NH2), 6.46 (dd, J = 10.4, 17.2 Hz, 1H, CHCH2), 6.23 (dd, J = 2.4, 17.2 Hz, 1H, CHCH2), 5.70 (dd, J = 2.0, 10.0 Hz, 1H, CHCH2), 5.55 (s, 2H, CH2) | 388 | 0.68 | C |
| 84 | 5-acrylamido-1-(4-(trifluoro-methyl)phenyl)-1H-indole-3-carboxamide | 1H NMR (400 MHz, DMSO-d6) δ = 10.22 (s, 1H, ArNH), 8.52 (d, J = 1.6 Hz, 1H, Ar), 8.41 (s, 1H, Ar), 8.00 (d, J = 8.6 Hz, 2H, Ar), 7.88 (d, J = 8.4 Hz, 2H, Ar), 7.77 (dd, J = 2.0, 8.8 Hz, 1H, Ar), 7.68-7.47 (m, 2H, Ar, CONH2), 7.16-6.96 (m, 1H, CONH2), 6.51-6.44 (m, 1H, CHCH2), 6.26 (dd, J = 2.0, 16.8 Hz, 1H, CHCH2), 5.78-5.68 (dd, J = 2.0, 2.4 Hz, 1H, CHCH2). | 374 | 0.78 | C |

Compounds of formula (I) underwent biochemical studies in order to determine their capacity to inhibit YAP1/TAZ-TEAD or TEAD-dependent gene transcription.

TEAD-Luciferase Reporter Assay

Luciferase-based gene reporter assays were used, employing the TEAD responsive promoter element that are stably integrated to different human tumor cell lines in order to monitor YAP1-TEAD and TAZ-TEAD activity and to study YAP1/TAZ-TEAD activity modulation by small molecule compounds. Luciferase-based gene reporter assays employing the GAPDH promoter element and stably integrated to different human tumor cell lines are used as counter screen control cell lines.

Tumor cell lines with stable integration of the 8XGTIIC-Luciferase construct (Dupont et al., Nature 2011) or the GAPDH-Luciferase control plasmid, are seeded in culture medium in 96-well plates at a density of 8000 cells/well. Following an overnight incubation in a 37° C., 5% $CO_2$ growth chamber, cells are treated with compounds described above at 10 doses ranging between 1 and 10000 nM for 48 hrs. After compound incubation, cells are lysed with Bright-Glo Luciferase Assay System (Promega E2620) and luciferase activity is measured using a luminescent plate reader.

The inhibitory activity of the compounds with respect to luciferase activity is given by the concentration which inhibits 50% of activity of non-treated cells. IC50s are determined with a nonlinear regression model on XLfit software analysis (IDBS, UK).

The IC50 values for the compounds of the invention were generally less than 1 μM, more particularly between 1 and 550 nM and even more particularly between 1 and 100 nM, as indicated in the table below:

| example No | TEAD IC50 (nM) |
|---|---|
| 1 | 24 |
| 2 | 1087 |
| 3 | 25 |
| 4 | 558 |
| 5 | 61 |
| 6 | 4044 |
| 7 | 10000 |
| 8 | 296 |
| 9 | 143 |
| 10 | 7224 |
| 11 | 30 |
| 12 | 241 |
| 13 | 63 |
| 14 | 236 |
| 15 | 496 |
| 16 | 31 |
| 17 | 54 |
| 18 | 963 |
| 19 | 195 |
| 20 | 7755 |
| 21 | 35 |
| 22 | 1404 |
| 23 | 369 |
| 24 | 1000 |
| 25 | 1000 |
| 26 | 357 |
| 27 | 10000 |
| 28 | 10000 |
| 29 | 43 |
| 30 | 10000 |
| 31 | 20 |
| 32 | 7842 |
| 33 | 41 |
| 34 | 10000 |
| 35 | 2331 |
| 36 | 4559 |
| 37 | >10000 |

-continued

| example No | TEAD IC50 (nM) |
|---|---|
| 38 | 1500 |
| 39 | 84 |
| 40 | 10000 |
| 41 | 10000 |
| 42 | 211 |
| 43 | 36 |
| 44 | 8 |
| 45 | 106 |
| 46 | >10000 |
| 47 | >10000 |
| 48 | >10000 |
| 49 | >10000 |
| 50 | 4679 |
| 51 | 313 |
| 52 | 41 |
| 53 | 33 |
| 54 | 388 |
| 55 | 185 |
| 56 | 10000 |
| 57 | 191 |
| 58 | 2006 |
| 59 | 2872 |
| 60 | 88 |
| 61 | 41 |
| 62 | 64 |
| 63 | 29 |
| 64 | 108 |
| 65 | 59 |
| 66 | 1852 |
| 67 | 8535 |
| 68 | 1088 |
| 69 | 9 |
| 70 | 12 |
| 71 | 24 |
| 72 | 15 |
| 73 | 244 |
| 74 | 106 |
| 75 | 458 |
| 76 | 3829 |
| 77 | 534 |
| 78 | 141 |
| 79 | 85 |
| 80 | 18 |
| 81 | 68 |
| 82 | 158 |
| 83 | 1794 |
| 84 | 620 |

It is therefore apparent that the compounds of formula (I) have an inhibitory activity of YAP1/TAZ-TEAD or TEAD-dependent gene transcription.

The compounds of formula (I) may thus be used as inhibitors of YAP1/TAZ-TEAD or TEAD-dependent gene transcription.

The compounds of formula (I) may thus be used as medicaments, especially medicaments which are inhibitors of YAP1/TAZ-TEAD or TEAD-dependent gene transcription.

Thus, according to another of its aspects, a subject of the invention is medicaments that comprise a compound of formula (I), or an addition salt thereof with a pharmaceutically acceptable acid.

These medicaments are employed therapeutically in the treatment of cancer, in particular in the treatment of breast, ovarian, uterine, prostate, lung, gastric, colorectal, bladder, pancreatic and liver cancers, sarcomas, esophageal, head and neck cancers, uveal melanoma, or glioma.

According to another of its aspects, the present invention relates to pharmaceutical compositions comprising as active principle, a compound of formula (I). These pharmaceutical compositions contain an effective dose of at least one compound of formula (I), or a pharmaceutically acceptable salt of the said compound.

These pharmaceutical compositions may also contain at least one pharmaceutically acceptable excipient.

The said excipients are chosen, according to the pharmaceutical form and the desired mode of administration, from the usual excipients known to those skilled in the art.

The compounds of formula (I) may be used in the treatment of pathologies involving YAP1/TAZ-TEAD or TEAD-dependent gene transcription inhibitors.

In particular, the compounds of formula (I) may be used as an anticancer agent, in particular for use in the treatment of breast, ovarian, uterine, prostate, lung, gastric, colorectal, bladder, pancreatic and liver cancers, sarcomas, esophageal, head and neck cancers, uveal melanoma, or glioma.

The compounds of formula (I) may also be used in the treatment of a patient who has exhibited resistance to prior anti-cancer therapy.

The present invention, according to another of its aspects, also provides a method of treating the pathologies indicated above.

Thus, described is also a method of treating cancer, in particular breast, ovarian, uterine, prostate, lung, gastric, colorectal, bladder, pancreatic and liver cancers, sarcomas, esophageal, head and neck cancers, uveal melanoma, or glioma, including administering to a subject in need thereof a therapeutically effective amount of at least one compound of formula (I) or a pharmaceutically acceptable salt thereof.

The compounds of formula (I) may also be used in a method if treating cancer in a patient who has exhibited resistance to prior anti-cancer therapy.

These compounds may be used in monotherapy or combination with radiotherapy or chemotherapy.

The invention claimed is:

1. A compound of the following formula:

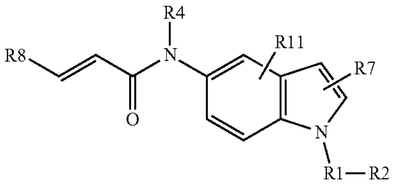

wherein

R1 is a single bond or an (C1-C4) alkylene group;

R2 is selected from the group consisting of:

an (C1-C4) alkyl group substituted with one or more fluorine atoms;

an (C1-C3) alkoxy group substituted with one or more fluorine atoms;

a phenyl group unsubstituted or substituted with one or more R3 groups;

a (C4-C8) cycloalkyl group unsubstituted or substituted with one or more R5 groups;

a (C4-C8) heterocyclyl group unsubstituted or substituted with one or more R6 groups; and a NR9R10 group;

R3 is selected from the group consisting of:

an (C1-C4) alkyl group unsubstituted or substituted with one or more fluorine atoms;

a cyclopropyl group;

a halogen atom;

an (C1-C3) alkoxy group unsubstituted or substituted with one or more fluorine atoms;

a pentafluorosulfanyl group;

a nitrile group;

a (C1-C3) trialkylsilyl group;

an (C1-C3) alkylsulfonyl group; and a phenyl group unsubstituted or substituted with a trifluoromethyl group;

R4 is a hydrogen atom or an (C1-C4) alkyl group;

R5 is a fluorine atom or a trifluoromethyl group;

R6 is selected from the group consisting of:

a phenyl group unsubstituted or substituted with one or more fluorine atoms or one or more $CF_3$ groups;

an (C1-C4) alkyl group substituted with one or more fluorine atoms; and a fluorine atom;

R7 is selected from the group consisting of:

a hydrogen atom;

a nitrile group;

an (C1-C4) alkyl group unsubstituted or substituted with an (C1-C3) alkoxy group or a hydroxy group;

a COO(C1-C4) alkyl group; and a CONH2 group;

R8 is a hydrogen atom or an (C1-C4) alkyl group unsubstituted or substituted with a di(C1-C4) alkylamino group;

R9 and R10 are identical or different and are selected from the group consisting of an (C1-C3) alkyl group unsubstituted and an (C1-C3) alkyl group substituted with one or more fluorine atoms; and R11 is selected from the group consisting of a hydrogen atom, a fluorine atom, and a chlorine atom;

or a pharmaceutically acceptable salt thereof.

2. The compound according to claim 1, wherein R4 is a hydrogen atom, or a pharmaceutically acceptable salt thereof.

3. The compound according to claim 1, wherein R7 is a hydrogen atom, or a pharmaceutically acceptable salt thereof.

4. The compound according to claim 1, wherein R8 is a hydrogen atom, or a pharmaceutically acceptable salt thereof.

5. The compound according to claim 1, wherein R11 is a hydrogen atom, or a pharmaceutically acceptable salt thereof.

6. A compound of formula (I):

(I)

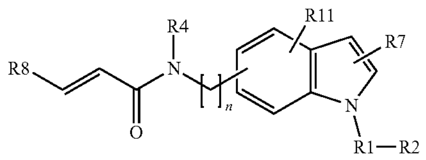

wherein n is 0;

R1 is a single bond;

R2 is selected from the group consisting of:

a phenyl group unsubstituted or substituted with one or more R3 groups;

a (C4-C8) cycloalkyl group unsubstituted or substituted with one or more R5 groups; and a (C4-C8) heterocyclyl group unsubstituted or substituted with one or more R6 groups;

R3 is selected from the group consisting of:

an (C1-C4) alkyl group unsubstituted or substituted with one or more fluorine atoms;

a cyclopropyl group;

a halogen atom;

an (C1-C3) alkoxy group unsubstituted or substituted with one or more fluorine atoms;

a pentafluorosulfanyl group;

a nitrile group;

a (C1-C3) trialkylsilyl group;

an (C1-C3) alkylsulfonyl group; and a phenyl group unsubstituted or substituted with a trifluoromethyl group;

R4 is a hydrogen atom or an (C1-C4) alkyl group;

R5 is a fluorine atom or a trifluoromethyl group;

R6 is selected from the group consisting of:

a phenyl group unsubstituted or substituted with one or more fluorine atoms or one or more $CF_3$ groups;

an (C1-C4) alkyl group substituted with one or more fluorine atoms; and a fluorine atom;

R7 is selected from the group consisting of:

a hydrogen atom;

a nitrile group;

an (C1-C4) alkyl group unsubstituted or substituted with an (C1-C3) alkoxy group or a hydroxy group;

a COO(C1-C4) alkyl group; and a CONH2 group;

R8 is a hydrogen atom or an (C1-C4) alkyl group unsubstituted or substituted with a di(C1-C4) alkylamino group; and R11 is selected from the group consisting of a hydrogen atom, a fluorine atom, and a chlorine atom;

or a pharmaceutically acceptable salt thereof.

7. The compound according to claim 6, wherein R2 is a phenyl group substituted with one or more R3 groups, or a pharmaceutically acceptable salt thereof.

8. The compound according to claim 6, wherein R3 is an (C1-C4) alkyl group substituted with one or more fluorine atoms, or a pharmaceutically acceptable salt thereof.

9. A compound selected from:

N-[1-[3-(trifluoromethyl)phenyl]methyl]indol-5-yl]acrylamide;

N-methyl-N-(1-(3-(trifluoromethyl)benzyl)-1H-indol-5-yl)acrylamide;

N-(1-(5,5,5-trifluoropentyl)-1H-indol-5-yl)acrylamide;

N-(1-(1-(3-(trifluoromethyl)phenyl)ethyl)-1H-indol-5-yl)acrylamide;

N-(1-(3-(pentafluoro-16-sulfanyl)benzyl)-1H-indol-5-yl)acrylamide;

N-(1-(4-(pentafluoro-16-sulfanyl)benzyl)-1H-indol-5-yl)acrylamide;

N-(1-(4-(trifluoromethoxy)benzyl)-1H-indol-5-yl)acrylamide;

N-(1-(3-(trifluoromethoxy)benzyl)-1H-indol-5-yl)acrylamide;

N-(1-(3-iodobenzyl)-1H-indol-5-yl)acrylamide;

N-(1-(2-fluoro-5-(trifluoromethyl)benzyl)-1H-indol-5-yl)acrylamide;

N-(3-methyl-1-(3-(trifluoromethyl)benzyl)-1H-indol-5-yl)acrylamide;

N-(1-(3-methoxybenzyl)-1H-indol-5-yl)acrylamide;

N-(2-methyl-1-(3-(trifluoromethyl)benzyl)-1H-indol-5-yl)acrylamide;

N-(3-cyano-1-(3-(trifluoromethyl)benzyl)-1H-indol-5-yl)acrylamide;

N-(1-(3-cyclopropylbenzyl)-1H-indol-5-yl)acrylamide;

N-(2,3-dimethyl-1-(3-(trifluoromethyl)benzyl)-1H-indol-5-yl)acrylamide;

N-(1-(3-methylbenzyl)-1H-indol-5-yl)acrylamide;

N-(1-Benzyl-1H-indol-5-yl)-acrylamide;

N-(1-(3-(trifluoromethyl)benzyl)-1H-indol-4-yl)acrylamide;

(E)-4-(dimethylamino)-N-(1-(3-(trifluoromethyl)benzyl)-1H-indol-4-yl) but-2-enamide;

N-(1-(3-(trifluoromethyl)benzyl)-1H-indol-6-yl)acrylamide;

N-(1-((4,4-difluorocyclohexyl)methyl)-1H-indol-5-yl) acrylamide;

N-(1-((tetrahydro-2H-pyran-4-yl)methyl)-1H-indol-5-yl) acrylamide;

N-(1-((4-(trifluoromethyl)cyclohexyl)methyl)-1H-indol-5-yl)acrylamide;

N-(1-((1,1-difluorospiro[2.3]hexan-5-yl)methyl)-1H-indol-5-yl)acrylamide;

N-(1-((3-fluorocyclopentyl)methyl)-1H-indol-5-yl)acrylamide;

N-(1-(cyclohexylmethyl)-1H-indol-5-yl)acrylamide;

N-(1-((3-(trifluoromethyl)cyclobutyl)methyl)-1H-indol-5-yl)acrylamide;

N-(1-((3,3-difluorocyclopentyl)methyl)-1H-indol-5-yl) acrylamide;

N-(1-([1,1'-biphenyl]-4-ylmethyl)-1H-indol-5-yl)acrylamide;

N-(1-((3'-(trifluoromethyl)-[1,1'-biphenyl]-4-yl)methyl)-1H-indol-5-yl)acrylamide;

N-(1-((4'-(trifluoromethyl)-[1,1'-biphenyl]-4-yl)methyl)-1H-indol-5-yl)acrylamide;

N-(1-((trans)-4-(trifluoromethyl)cyclohexyl)-1H-indol-5-yl)acrylamide;

N-(1-((cis)-4-(trifluoromethyl)cyclohexyl)-1H-indol-5-yl)acrylamide;

N-(1-((1-(4-(trifluoromethyl)phenyl)piperidin-4-yl) methyl)-1H-indol-5-yl)acrylamide;

N-(1-(2-(methyl (2,2,2-trifluoroethyl)amino)ethyl)-1H-indol-5-yl)acrylamide;

N-(1-(2-(2,2,2-trifluoroethoxy)ethyl)-1H-indol-5-yl) acrylamide;

N-(1-(1-(2,2,2-trifluoroethyl)piperidin-4-yl)-1H-indol-5-yl)acrylamide;

N-(1-(4,4-difluorocyclohexyl)-1H-indol-5-yl)acrylamide;

N-(1-(1-(4-(trifluoromethyl)phenyl)piperidin-4-yl)-1H-indol-5-yl)acrylamide;

N-(1-(3-(3,3-difluoropyrrolidin-1-yl)propyl)-1H-indol-5-yl)acrylamide;

N-(1-(4-(trimethylsilyl)benzyl)-1H-indol-5-yl)acrylamide;

N-(1-(3-(trifluoromethyl)phenyl)-1H-indol-5-yl)acrylamide;

N-(1-(4-(trifluoromethyl)phenyl)-1H-indol-5-yl)acrylamide;

N-(1-(6-(trifluoromethyl)pyridin-3-yl)-1H-indol-5-yl) acrylamide;

N-(1-(5-(trifluoromethyl)pyridin-2-yl)-1H-indol-5-yl) acrylamide;

N-(1-(pyridin-3-yl)-1H-indol-5-yl)acrylamide;

N-(1-(4-fluorophenyl)-1H-indol-5-yl)acrylamide;

N-(1-(3,4-difluorophenyl)-1H-indol-5-yl)acrylamide;

N-(1-(3-(methylsulfonyl)phenyl)-1H-indol-5-yl)acrylamide;

N-(1-(4-cyanophenyl)-1H-indol-5-yl)acrylamide;

N-(1-(3,5-difluorobenzyl)-1H-indol-5-yl)acrylamide;

N-(1-(3,4-difluorobenzyl)-1H-indol-5-yl)acrylamide;

N-(1-(3-cyanobenzyl)-1H-indol-5-yl)acrylamide;

N-(1-((5-(trifluoromethyl)furan-2-yl)methyl)-1H-indol-5-yl)acrylamide;

N-(1-(thiazol-4-ylmethyl)-1H-indol-5-yl)acrylamide;

N-(1-((2-(trifluoromethyl) thiazol-4-yl)methyl)-1H-indol-5-yl)acrylamide;

N-(1-(3-(trifluoromethyl)benzyl)-1H-indol-7-yl)acrylamide;

N-(1-(3-(methylsulfonyl)benzyl)-1H-indol-5-yl)acrylamide;

N-(3-(methoxymethyl)-1-(3-(trifluoromethyl)benzyl)-1H-indol-5-yl)acrylamide;

methyl 5-acrylamido-1-(3-(trifluoromethyl)benzyl)-1H-indole-3-carboxylate;

N-(1-(3-(trifluoromethyl)phenyl)-1H-indol-6-yl)acrylamide;

N-(1-(4-(pentafluoro-16-sulfanyl)phenyl)-1H-indol-5-yl) acrylamide;

N-(1-(4-(trifluoromethyl)phenyl)-1H-indol-6-yl)acrylamide;

N-(1-(2-methyl-4-(trifluoromethyl)phenyl)-1H-indol-5-yl)acrylamide;

N-(1-(3,5-difluorophenyl)-1H-indol-5-yl)acrylamide;

N-(1-(5-fluoropyridin-3-yl)-1H-indol-5-yl)acrylamide;

N-(1-(2-(trifluoromethyl)pyridin-4-yl)-1H-indol-5-yl) acrylamide;

N-[3-methyl-1-[4-(trifluoromethyl)phenyl]indol-5-yl] acrylamide;

N-[2-methyl-1-[4-(trifluoromethyl)phenyl]indol-5-yl] acrylamide;

N-methyl-N-[2-methyl-1-[4-(trifluoromethyl)phenyl]indol-5-yl]acrylamide;

N-(3-(methoxymethyl)-1-(4-(trifluoromethyl)phenyl)-1H-indol-5-yl)acrylamide;

N-(6-fluoro-1-(4-(trifluoromethyl)phenyl)-1H-indol-5-yl)acrylamide;

N-methyl-N-(1-(4-(trifluoromethyl)phenyl)-1H-indol-5-yl)acrylamide;

(E)-N-(1-(4-(trifluoromethyl)phenyl)-1H-indol-5-yl) but-2-enamide;

(E)-4-(dimethylamino)-N-(1-(4-(trifluoromethyl)phenyl)-1H-indol-5-yl) but-2-enamide;

N-(6-chloro-1-(4-(trifluoromethyl)phenyl)-1H-indol-5-yl)acrylamide;

N-(6-chloro-1-(3-(trifluoromethyl)benzyl)-1H-indol-5-yl)acrylamide;

N-(7-chloro-1-(3-(trifluoromethyl)benzyl)-1H-indol-5-yl)acrylamide;

N-(6-fluoro-1-(3-(trifluoromethyl)benzyl)-1H-indol-5-yl) acrylamide;

N-(7-chloro-1-(4-(trifluoromethyl)phenyl)-1H-indol-5-yl)acrylamide;

N-(3-(hydroxymethyl)-1-(4-(trifluoromethyl)phenyl)-1H-indol-5-yl)acrylamide;

5-acrylamido-1-(3-(trifluoromethyl)benzyl)-1H-indole-3-carboxamide; and 5-acrylamido-1-(4-(trifluoromethyl)phenyl)-1H-indole-3-carboxamide;

and a pharmaceutically acceptable salt thereof.

* * * * *